(12) United States Patent
Dellinger et al.

(10) Patent No.: US 10,196,418 B2
(45) Date of Patent: Feb. 5, 2019

(54) PHOSPHOROUS PROTECTING GROUPS AND METHODS OF PREPARATION AND USE THEREOF

(71) Applicant: Agilent Technologies, Inc., Loveland, CA (US)

(72) Inventors: Douglas J. Dellinger, Boulder, CO (US); Luca Monfregola, Boulder, CO (US); Marvin Caruthers, Boulder, CO (US); Mithun Roy, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 691 days.

(21) Appl. No.: 14/701,288

(22) Filed: Apr. 30, 2015

(65) Prior Publication Data

US 2015/0315227 A1 Nov. 5, 2015

Related U.S. Application Data

(60) Provisional application No. 61/986,594, filed on Apr. 30, 2014.

(51) Int. Cl.
| | |
|---|---|
| *C07H 19/10* | (2006.01) |
| *C07H 21/04* | (2006.01) |
| *C07H 19/23* | (2006.01) |
| *C07H 19/073* | (2006.01) |
| *C07H 19/173* | (2006.01) |

(52) U.S. Cl.
CPC .......... *C07H 19/10* (2013.01); *C07H 19/073* (2013.01); *C07H 19/173* (2013.01); *C07H 19/23* (2013.01); *C07H 21/04* (2013.01); *Y02P 20/55* (2015.11)

(58) Field of Classification Search
CPC ....................................... C07H 19/10
USPC ....................................... 536/4.1
See application file for complete search history.

(56) References Cited

U.S. PATENT DOCUMENTS

| | | | |
|---|---|---|---|
| 4,415,732 A | 11/1983 | Caruthers et al. | |
| 5,955,591 A * | 9/1999 | Imbach | C07F 9/65616 536/23.1 |
| 6,020,475 A * | 2/2000 | Capaldi | C07H 21/00 536/23.1 |
| 6,222,030 B1 | 4/2001 | Dellinger et al. | |
| 6,274,725 B1 | 8/2001 | Sanghvi et al. | |
| 2002/0058802 A1 | 5/2002 | Dellinger et al. | |
| 2006/0178507 A1 | 8/2006 | Berry et al. | |
| 2013/0052690 A1 | 2/2013 | Chi et al. | |

FOREIGN PATENT DOCUMENTS

| | | | | |
|---|---|---|---|---|
| WO | WO9940101 A1 | | 8/1999 | |
| WO | WO-2014031575 A1 | * | 2/2014 | ............ C07H 21/00 |

OTHER PUBLICATIONS

Feng, et al. "Synthesis and Antibacterial Activities of Erythromycin Derivatives", Chem. Res., Chinese U., 2005, 21 ( 2 ) , 177-182.
Froehler, et al. "Dialkylformamidines: depurnation resstant N6-protecting group for deoxyadenosine", Nucliec Acid Research, vol. 11, No. 22, 1983, 8031-8036.
Froehler, et al. "Synthesis of DNA via deoxynucleoside H-phosphonate intennediates", Nucliec Acid Research, vol. 14, No. 13, 1986, 5399-5407.
Leproust, et al. "Synthesis of high-quality libraries of long (150mer) oligonucleotides by a novel depurination controlled process", Nucleic Acids Research, 2010, vol. 38, No. 8, 2522-2540.
Septak, "Kinetic studies on depurination and detritylation of CPG-bound intermediates during oligonucleotide synthesis", Nucleic Acids Research, 1996, vol. 24, No. 15 3053-3058.
PubChem. Substance Record for SID 23213079, 2007, https:l/pubchem.ncbi.nlm.nih.gov/substance/23213079.
PubChem. Substance Record for SID 23300532, 2007, https:l/pubc!Jem.ncbi.nlm.nih.gov/substance/23300532.
Eleuteri, et al., "Efficient Synthesis of Deoxyribonucleoside Phosphoramidites by Eliminating the Use of Additional Activator", Nucleosides & Nucleotides, Aug. 1, 1999, pp. 1879-1882, vol. 18, No. 8.
Iyer et al., "Bioreversible Oligonucleotide Conjugates by Site-Specific Derivatization", Bioorganic & Medicinal Chemistry Letters, Apr. 8, 1997, pp. 871-876, vol. 7, No. 7.
Abbas, et al., "An improved procedure for the synthesis of vinylphosphonate-linked nucleic acids", Tetrahedron Letters, Jun. 1, 2000, pp. 4513-4517, vol. 41, No. 22.
Abramova et al., "Synthesis and Properties of Photolabile (Caged) Phosphotriester Derivatives of Dinucleoside Phosphates", Russian Journal of Bioorganic Chemistry, 2000, pp. 174-182, vol. 26, No. 3.
European Communication dated Oct. 16, 2017 for European Application No. 15786514.8.
Marugg J. et al., "A New and Versatile Approach to the Preparation of Valuable Deoxynucleoside 3-Phosphite Intermediates", Tetrahedron Letters, Elsevier, Amsterdam, Jan. 1, 1986, pp. 2271-2274, vol. 27, No. 20.
Smith E. et al., "A Novel Structural Class of Photoswitchable Oligonucleotide", Tetrahedron Letters, Elsevier, Aug. 16, 2007, pp. 6569-6572, vol. 48, No. 37.

(Continued)

Primary Examiner — Jezia Riley

(57) ABSTRACT

Aspects of the present disclosure include compositions that make use of phosphorus and/or nucleobase protecting groups which find use in the synthesis of long polynucleotides. Phosphorus protecting groups are provided that help increase the stepwise coupling yield and/or phosphorous protecting groups that can be removed during the oxidation step. Amidine nucleobase protecting groups are provided that find use in the subject compositions and methods which provides for e.g., increased resistance to depurination during polynucleotide synthesis. In some instances, the methods and compositions disclosed herein utilize a combination of the phosphorus and amidine nucleobase protecting groups in the synthesis of polynucleotides having a sequence of 200 or more monomeric units in length. Also provided are methods for synthesizing a polynucleotide (e.g., a DNA) using one or more compounds disclosed herein.

20 Claims, 29 Drawing Sheets

(56) References Cited

OTHER PUBLICATIONS

Theisen P. et al., "N-6-Dialkylformamidine-2'-deoxyadenosine Phosphoramidites in Oligodeoxynucleotide Synthesis, Rapid Deprotection of Oligodeoxynucleotides", Nucleosides & Nucleotides, Dec. 1, 1993, pp. 1033-1046, vol. 12, No. 10.
McBride L. et al., "Amidine Protecting Groups for Oligonucleotide Synthesis", Journal of American Chemical Society, Apr. 1, 1986, pp. 2040-2048, vol. 108.
Wu Li et al., "Synthesis of Site-Specifically Phosphate-Caged SiRNAs and Evaluation of Their RNAi Activity and Stability", Chemistry, A European Journal, Sep. 15, 2014, pp. 12114-12122, vol. 20, No. 38.

* cited by examiner

Comparison of DAD chromatograms of dT$_{20}$ using 6-Bromo-2-naphtalenemethanol as phosphorus protecting group without and with a 2-carbamoyl-2-cyanoethylene-1,1-dithiolate treatment

| Column | C18, 1.7 μm, 2.1 X 100m |
|---|---|
| Eluent system | 2 |
| Gradient | 1 |
| Cleavage | Ammonia 2 hours RT |

TIC, DAD chromatograms and mass analysis of $dT_{20}$ using 3-cyanobenzyl alcohol as phosphorus protecting group with a 2-carbamoyl-2-cyanoethylene-1,1-dithiolate treatment

| Column | C18, 1.7 µm, 2.1 X 100nm |
|---|---|
| Eluent system | 2 |
| Gradient | 1 |
| Cleavage | Ammonia 2 hours RT |

EIC chromatograms of the failure sequences and side products in a dT$_{20}$ synthesis using Acetyl-L-threoninemethylester as phosphorus protecting group DAD chromatogram and Mass analysis of dT$_{20}$ using S-ethylbenzothioate as phosphorus protecting group

| Column | C18, 1.7 µm, 2.1 X 100nm |
| --- | --- |
| Eluent system | 2 |
| Gradient | 1 |
| Cleavage | Ammonia overnight 55°C |

TIC, DAD chromatograms and mass analysis of dT$_{60}$ using 4-cyanobenzyl alcohol as phosphorus protecting group with a 2-carbamoyl-2-cyanoethylene-1,1-dithiolate treatment

| Column | C4, 1.7 µm, 2.1 X 150nm |
|---|---|
| Eluent system | 2 |
| Gradient | 2 |
| Cleavage | Ammonia overnight 55°C |

EIC chromatogram of the failure sequences in a dT$_{60}$ synthesis using 4-cyanobenzyl alcohol as phosphorus protecting group.

EIC chromatogram of the failure sequences in a $dT_{60}$ synthesis using Acetyl-L-threoninemethylester protecting group.

TIC, DAD chromatograms and Mass analysis of dT$_{20}$ using S-ethylbenzothioate as phosphorus protecting group

| Column | C4, 1.7 μm, 2.1 X 150nm |
|---|---|
| Eluent system | 2 |
| Gradient | 3 |
| Cleavage | Ammonia overnight 55°C |

EIC chromatogram of the failure sequences in a dT$_{60}$ synthesis using S-ethylbenzothioate protecting group (22)

(23)

(24)

(25)

(26)

(27)

(28)

(29)

(30)

(31)

PHOSPHOROUS PROTECTING GROUPS AND METHODS OF PREPARATION AND USE THEREOF

CROSS REFERENCE TO RELATED APPLICATIONS

Pursuant to 35 U.S.C. § 119(e), this application claims priority to the filing date of U.S. provisional application Ser. No. 61/986,594, filed Apr. 30, 2014, the disclosure of which is herein incorporated by reference.

FIELD OF THE INVENTION

The invention generally relates to synthesis of nucleic acids. More particularly, the invention relates to novel phosphorous protecting groups and novel nucleobase protecting groups and related compounds useful in synthesis of DNAs, and compositions and methods thereof.

INTRODUCTION

Chemical synthesis of oligonucleotides, synthetic strands of DNA and RNA, is the chemical synthesis of relatively short fragments of nucleic acids with defined chemical structure and sequence. The technique is extremely important and useful owing to the wide variety of applications in current laboratory practice. Oligonucleotide synthesis provides a rapid and inexpensive access to custom-made oligonucleotides of the desired sequence. Oligonucleotides find a variety of applications in molecular biology and medicine, e.g., antisense oligonucleotides, small interfering RNA, primers for DNA sequencing and amplification, molecular probes, etc.

Chemical synthesis of oligonucleotide is typically carried out in 3' to 5' direction as solid-phase synthesis using phosphoramidite method and phosphoramidite building blocks derived from protected 2'-deoxynucleosides (dA, dC, dG, and T), ribonucleosides (A, C, G, and U), or chemically modified nucleosides, e.g., 2-O-methyl, 2'-F, LNA, etc. To synthesize oligonucleotide, the building blocks are sequentially coupled to the growing oligonucleotide chain in the desired order. Once the chain assembly is complete, the product is deprotected, released from the solid phase to solution, and collected. (U.S. Pat. No. 4,415,732; McBride, et al. 1983 *Tetrahedron Letters* 24:245-248; Sinha, et al. 1984 *Nuc. Acids Res.* 12:4539-4557.)

DNA synthesis with cyanoethyl phosphoramidites has been powerful at enabling synthesis of oligonucleotides of 200 mers or shorter on solid support and on arrays synthesis. However, the currently available chemistry has encountered difficulties with the synthesis of longer oligonucleotides, which has been found to contain single base deletions (SBD) in their sequences and large deletions (deletions of longer segments of oligos). Single base deletions may occur due to insufficient stepwise coupling yields, whereas large deletions of oligonucleotide segments can be due to the instability of the phosphotriester linkages exposed to the repeated treatments of harsh chemicals during the oligonucleotide synthesis.

Thus, for existing synthetic methodologies, the undesired side reactions have set practical limits for the length of synthetic oligonucleotides (up to about 200 nucleotide residues) because the number of errors accumulates with the length of the oligonucleotide being synthesized. (Beaucage, et al. 1992 "Advances in the Synthesis of Oligonucleotides by the Phosphoramidite Approach" *Tetrahedron* 48 (12): 2223; see also, Caruthers, et al. 1987 "Synthesis of oligonucleotides using the phosphoramidite method" *Biophosphates and their Analogues Synthesis, Structure, Metabolism and Activity*, eds. K. S. Bruzik, W. J. Stec, Elsevier Sci. Publ., 3-21.) Since errors in the desired sequence are more likely as the sequence length increases, sequences of more than 80 bases (in particular, more than 200 bases) often need to be isolated by high-performance liquid chromatography (HPLC) to increase purity. Moreover, the stepwise yield or coupling efficiency greatly limits the length of the oligonucleotide that can be synthesized. The overall yield for the synthesis of an oligonucleotide is expressed as $OY=y^{(n-1)}$; with OY being the Overall Yield, y the stepwise coupling yield and n the length of the oligonucleotide or the number of nucleotides in the oligonucleotide; thus a 200 mers oligonucleotide synthesized with a 99.7% coupling yield will have a $OY=y^{199}$, which equals to $OY=0.997^{199}=0.54996$ or 54.99% whereas a 200 mers synthesized with a 99.8% coupling efficiency will have a $OY=0.671394$ or 67.14%. The stepwise coupling yield affects drastically the Overall Yield for such long oligonucleotides, as demonstrated in this example where a 0.1% difference in the stepwise coupling yield results in a 12% change in OY. As a result, any improvements on the stepwise coupling efficiency will greatly increase the OY of the full length oligonucleotide and is desired.

A significant challenge remains in chemical synthesis of oligonucleotide. In particular, new phosphorus protecting groups are needed that increase the stepwise coupling yield and/or phosphorous protecting groups that can be removed during the oxidation step so as to avoid the instability of the phosphotriester linkage during the oligonucleotide synthesis as discussed previously. This is a key unmet need for novel approaches of reliable synthesis of nucleic acid molecules of greater length than those produced by conventional techniques, while achieving acceptable purity and yield.

SUMMARY

The present disclosure is based in part on the novel approaches to synthesize nucleic acid molecules of greater length than those produced by conventional techniques, while achieving acceptable purity and yield. Aspects of the present disclosure are methods and compositions that make use of phosphorus and/or nucleobase protecting groups that provide for the synthesis of long polynucleotides (e.g., DNA) having a sequence of 200 or more monomeric units in length.

Phosphorus protecting groups are provided that help increase the stepwise coupling yield and/or phosphorous protecting groups that can be removed during the oxidation step. Amidine nucleobase protecting groups are provided that find use in the subject compositions and methods which provides for increased resistance to depurination during polynucleotide synthesis, reduced nucleobase deprotection times, e.g., during polynucleotide cleavage in ammonia, and increased purity of crude oligonucleotides with less byproducts, e.g., nucleobase adducts. In some instances, the methods and compositions disclosed herein may utilize a combination of the phosphorus and nucleobase protecting groups in the synthesis of polynucleotides having a sequence of 200 or more monomeric units in length.

In one aspect, the present disclosure generally relates to a compound having the structural formula (I):

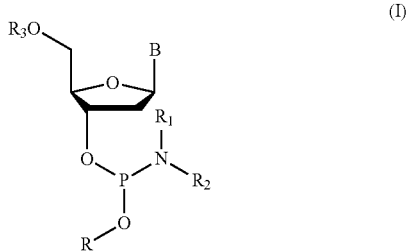

(I)

wherein B is a nucleobase or an analogue thereof; each of $R_1$ and $R_2$ is independently a linear, branched or cyclic, substituted or un-substituted alkyl, or $R_1$ and $R_2$ together form a 5-, 6-, 7- or 8-membered non-aromatic ring; $R_3$ is an acid-labile protecting group; and R is a group selected from the group consisting of benzyl alcohol derivatives, alpha-methyl aryl alcohols derivatives, naphthalene alcohol derivatives, bi-cyclic aliphatic alcohol derivatives or fused rings), S-ethylthioate derivatives and amino acid derivatives, with the proviso that R is not o-methyl benzyl.

In another aspect, the present disclosure generally relates to a method for synthesizing a polynucleotide (e.g., a DNA) using one or more compounds disclosed herein, wherein the synthesized DNA is of a length of at least about 200 nucleotides.

DEFINITIONS

Figure 1:
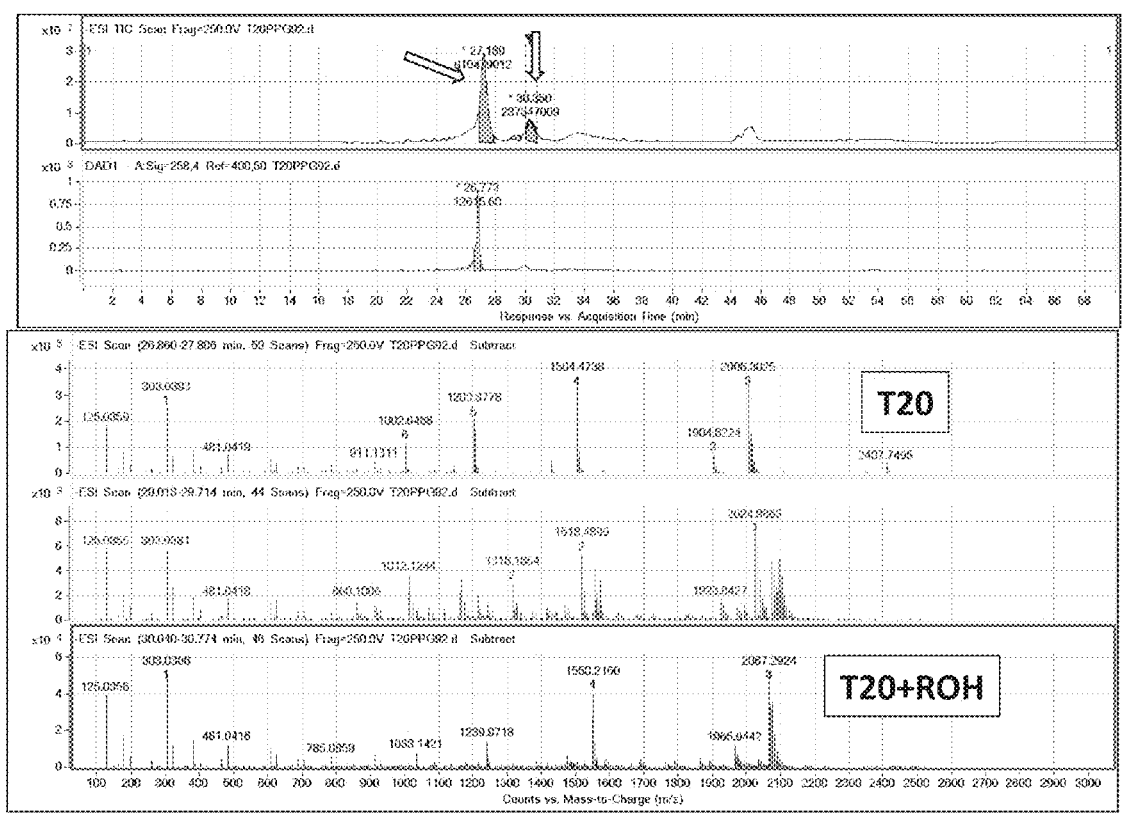
FIG. 1 shows TIC and HPLC chromatograms and Mass analysis of the synthesis of $dT_{20}$ using 1-(4-Bromophenyl) ethanol as phosphorus protecting group.

Definitions of specific functional groups and chemical terms are described in more detail below. General principles of organic chemistry, as well as specific functional moieties and reactivity, are described in "Organic Chemistry", Thomas Sorrell, University Science Books, Sausalito: 1999.

Certain compounds of the present disclosure may exist in particular geometric or stereoisomeric forms. The present disclosure contemplates all such compounds, including cis- and trans-isomers, R- and S-enantiomers, diastereomers, (D)-isomers, (L)-isomers, the racemic mixtures thereof, and other mixtures thereof, as falling within the scope of the present disclosure. Additional asymmetric carbon atoms may be present in a substituent such as an alkyl group. All such isomers, as well as mixtures thereof, are intended to be included in this present disclosure.

Isomeric mixtures containing any of a variety of isomer ratios may be utilized in accordance with the present disclosure. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present disclosure. Those of ordinary skill in the art will readily appreciate that analogous ratios are contemplated for more complex isomer mixtures.

If, for instance, a particular enantiomer of a compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in Protective Groups in Organic Synthesis, Third Ed. Greene, T. W. and Wuts, P. G., Eds., John Wiley & Sons, New York: 1999.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Sambrook et al., Molecular Cloning: A Laboratory Manual, 2nd Edition (Cold Spring Harbor Laboratory, 1989); and the like. Still, certain terms are defined below for the sake of clarity and ease of reference.

It will be appreciated that the compounds, as described herein, may be substituted with any number of substituents or functional moieties.

The terms "nucleotide" or "nucleotide moiety", as used herein, refer to a sub-unit of a nucleic acid (whether DNA or RNA or analogue thereof), which includes a phosphate group, a sugar group and a heterocyclic base, as well as analogs of such sub-units. Other groups (e.g., protecting groups) can be attached to any component(s) of a nucleotide.

The terms "nucleoside" or "nucleoside moiety", as used herein, refer a nucleic acid subunit including a sugar group and a heterocyclic base, as well as analogs of such sub-units. Other groups (e.g., protecting groups) can be attached to any component(s) of a nucleoside.

The terms "nucleoside" and "nucleotide" are intended to include those moieties that contain not only the known purine and pyrimidine bases, e.g. adenine (A), thymine (T), cytosine (C), guanine (G), or uracil (U), but also other heterocyclic bases that have been modified. Such modifications include methylated purines or pyrimidines, alkylated purines or pyrimidines, acylated purines or pyrimidines, halogenated purines or pyrimidines, deazapurines, alkylated riboses or other heterocycles. Such modifications include, e.g., diaminopurine and its derivatives, inosine and its derivatives, alkylated purines or pyrimidines, acylated purines or pyrimidines, thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, and substituted phenoxyacetyl, dimethylformamidine, dibutylformamidine, pyrrolodinoamidine, morpholinoamidine, and other amidine derivatives, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 7-deazaadenine, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl) uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

A "nucleobase" references the heterocyclic base of a nucleoside or nucleotide.

In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups including locked nucleic acids known as LNA and UNA unlocked nucleic acids, 2'-fluoro, 2'-O-alkyl, 2'-O-ethoxymethoxy, or are functionalized as ethers, amines, or the like.

The term "analogues", as used herein, refer to molecules having structural features that are recognized in the literature as being mimetics, derivatives, having analogous structures, or other like terms, and include, for example, polynucleotides incorporating non-natural (not usually occurring in nature) nucleotides, unnatural nucleotide mimetics such as 2'-modified nucleosides, peptide nucleic acids, oligomeric nucleoside phosphonates, and any polynucleotide that has added substituent groups, such as protecting groups or linking groups.

The term "nucleic acid", as used herein, refers to a polymer of any length, e.g., greater than about 2 bases, greater than about 10 bases, greater than about 100 bases, greater than about 500 bases, greater than 1,000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleotides, e.g., can participate in Watson-Crick base pairing interactions. Naturally-occurring nucleotides include guanosine and 2'-deoxyguanosine, cytidine and 2'-deoxycytidine, adenosine and 2'-deoxyadenosine, thymidine and uridine (G, dG, C, dC, A, dA and T, U respectively).

A nucleic acid may exist in a single stranded or a double-stranded form. A double stranded nucleic acid has two complementary strands of nucleic acid may be referred to herein as the "first" and "second" strands or some other arbitrary designation. The first and second strands are distinct molecules, and the assignment of a strand as being a first or second strand is arbitrary and does not imply any particular orientation, function or structure. The nucleotide sequences of the first strand of several exemplary mammalian chromosomal regions (e.g., BACs, assemblies, chromosomes, etc.), as well as many pathogens, are known, and may be found in NCBI's Genbank database, for example. The second strand of a region is complementary to that region.

The term "oligonucleotide", as used herein, refers to a single stranded multimer of nucleotides of, inter alia, from about 2 to 500 nucleotides. Oligonucleotides may be synthetic or may be made enzymatically, and, in some embodiments, are 10 to 50 nucleotides in length. Oligonucleotides may contain ribonucleotide monomers (i.e., may be oligoribonucleotides) or deoxyribonucleotide monomers. Oligonucleotides may contain, inter alia, 10 to 20, 21 to 30, 31 to 40, 41 to 50, 51-60, 61 to 70, 71 to 80, 80 to 100, 100 to 150, 150 to 500 or greater than 500 nucleotides in length, for example.

The terms "deoxyribonucleic acid" and "DNA", as used herein, refers to a nucleic acid composed of nucleotides and/or deoxyribonucleotides.

The terms "ribonucleic acid" and "RNA", as used herein, refer to a nucleic acid composed of nucleotides and/or ribonucleotides.

An "internucleotide bond" or "nucleotide bond" refers to a chemical linkage between two nucleoside moieties, such as the phosphodiester linkage in nucleic acids found in nature, or linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or a protecting group or replaced with another atom, e.g., a sulfur atom, or the nitrogen atom of a mono- or di-alkyl amino group.

The terms "heterocycle", "heterocyclic", "heterocyclic group" or "heterocyclo", as used herein, refer to fully saturated or partially or completely unsaturated cyclic groups having at least one heteroatom in at least one carbon atom-containing ring, including aromatic ("heteroaryl") or nonaromatic (for example, 3 to 13 member monocyclic, 7 to 17 member bicyclic, or 10 to 20 member tricyclic ring systems). Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be fused, bridged and/or joined through one or more spiro unions. Nitrogen-containing bases are examples of heterocycles. Other examples include piperidinyl, morpholinyl and pyrrolidinyl.

The term "electron-withdrawing group" refers to a moiety that has a tendency to attract valence electrons from neighboring atoms (i.e., the substituent is electronegative with respect to neighboring atoms). A quantification of the level of electron-withdrawing capability is given by the Hammett sigma constant. This well known constant is described in many references, for instance, March, Advanced Organic Chemistry 251-59, McGraw Hill Book Company, New York, (1977). Electron-withdrawing groups include nitro, acyl, formyl, sulfonyl, trifluoromethyl, cyano, chloride, and the like.

The term "electron-donating group" refers to a moiety that has a tendency to repel valence electrons from neighboring atoms (i.e., the substituent is less electronegative with respect to neighboring atoms). Electron-donating groups include amino, methoxy, alkyl (including C1-6 alkyl that can have a linear or branched structure), C4-9 cycloalkyl, and the like.

The phrase "protecting group", as used herein, refers to a species which prevents a portion of a molecule from undergoing a specific chemical reaction, but which is removable from the molecule following completion of that reaction. A "protecting group" is used in the conventional chemical sense as a group which reversibly renders unreactive a functional group under certain conditions of a desired reaction, as taught, for example, in Greene, et al., "Protective Groups in Organic Synthesis," John Wiley and Sons, Second Edition, 1991. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

The terms "hydroxyl protecting group" or "O-protecting group", as used herein, refers to a protecting group where the protected group is a hydroxyl. A "reactive-site hydroxyl" is the terminal 5'-hydroxyl during 3'-5' polynucleotide synthesis, or the 3'-hydroxyl during 5'-3' polynucleotide synthesis. A "free reactive-site hydroxyl" is a reactive-site hydroxyl that is available to react to form an internucleotide bond (e.g., with a phosphoramidite functional group) during polynucleotide synthesis.

The term "alkyl", as used herein, refers to a saturated straight chain, branched or cyclic hydrocarbon group (e.g., having 1 to 24, typically 1 to 12) carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. Alkyls include "cycloalkyls", which refer to cyclic alkyl groups such as cyclopropyl, cyclobutyl, cyclopentyl, cyclohexyl, cycloheptyl and cyclooctyl.

The term "alkenyl", as used herein, unless otherwise specified, refers to a branched, unbranched or cyclic (e.g. in the case of $C_5$ and $C_6$) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to eight carbon atoms, and specifically includes vinyl and allyl. The term "cycloalkenyl" refers to cyclic alkenyl groups.

The term "alkynyl", as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to eight carbon atoms, and includes, for example, acetylenyl and propynyl, and the term "cycloalkynyl" refers to cyclic alkynyl groups.

The term "hydrocarbyl", as used herein, refers to alkyl, alkenyl or alkynyl. Unless indicated otherwise, the term hydrocarbyl generally encompasses "substituted hydrocarbyl", which refers to hydrocarbyl moieties having substituents replacing a hydrogen on one or more carbons of the hydrocarbon backbone. Such substituents may include, for example, a hydroxyl, a halogen, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclic, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN, and the like. Cycloalkyls may be further substituted with alkyls, alkenyls, alkoxys, alkylthios, aminoalkyls, carbonyl-substituted alkyls, —CN, and the like.

The term "alkoxy" or "alkyloxy" means an alkyl group linked to oxygen and may be represented by the formula: R—O—, wherein R represents the alkyl group. An example is the methoxy group $CH_3O—$.

The term "aryl" refers to 5-, 6-, and 7-membered single- or multi-ring aromatic groups that may include, inter alia, from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The term "aryl" also includes polycyclic ring systems having two or more cyclic rings in which two or more carbons are common to two adjoining rings (the rings are "fused rings") wherein at least one of the rings is aromatic (e.g., the other cyclic rings may be cycloalkyls, cycloalkenyls, cycloalkynyls, aryls, and/or heterocycles). An example of a fused ring aryl group is naphthalene. A "lower aryl" contains up to 18 carbons, such as up to 14, 12, 10, 8 or 6 carbons.

The aromatic rings may be substituted at one or more ring positions with such substituents as described above for substituted hydrocarbyls, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclic, aromatic or heteroaromatic moieties, —$CF_3$, —CN, or the like.

The term "halogen", as used herein, refers to fluorine, chlorine, bromine, or iodine.

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

The term "functionalized", as used herein, refers to a process whereby a material is modified to have a specific moiety bound to the material, e.g., a molecule or substrate is modified to have the specific moiety; the material (e.g. molecule or support) that has been so modified is referred to as a functionalized material (e.g., functionalized molecule or functionalized support).

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group. For example, when an alkyl group has a "R" group and R is hydrogen, the alkyl group is considered unsubstituted at the marked location, whereas when that hydrogen is replaced with a halogen, it is considered substituted by a halogen at that location.

The term "substituent", as used herein, refers to a group that replaces another group in a chemical structure. Typical substituents include nonhydrogen atoms (e.g. halogens), functional groups (such as, but not limited to amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include alkyl, lower alkyl, aryl, aralkyl, lower alkoxy, thioalkyl, hydroxyl, thio, mercapto, amino, imino, halo, cyano, nitro, nitroso, azide, carboxy, sulfide, sulfone, sulfoxy, phosphoryl, silyl, silyloxy, boronyl, and modified lower alkyl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups. The descriptions (1) and (2) are equivalent to the moiety being optional and includes embodiments in which the moiety is present and embodiments in which the moiety is not present.

If the optional moiety is not present (is present in the structure zero times), adjacent groups described as linked by the optional moiety are linked to each other directly.

"Isolated" or "purified" generally refers to isolation of a substance (compound, polynucleotide, protein, polypeptide, polypeptide, chromosome, etc.) such that the substance comprises a substantial portion of the sample in which it resides (excluding solvents), i.e. greater than the substance is typically found in its natural or un-isolated state. Typically, a substantial portion of the sample comprises at least about 1%, at least about 5%, at least about 10%, at least about 20%, at least about 30%, at least about 50%, preferably at least about 80%, or more preferably at least about 90% of the sample (excluding solvents). For example, a sample of isolated RNA will typically comprise at least about 5% total RNA, where percent is calculated in this context as mass (e.g. in micrograms) of total RNA in the sample divided by mass (e.g. in micrograms) of the sum of (total RNA+other constituents in the sample (excluding solvent)). Techniques for purifying polynucleotides and polypeptides of interest are well known in the art and include, for example, gel electrophoresis, ion-exchange chromatography, affinity chromatography, flow sorting, and sedimentation according to density. In some embodiments, one or more of the nucleotide composition(s) is in isolated form.

As used herein, $(C_x-C_y)$ refers in general to groups that have from x to y (inclusive) carbon atoms. Therefore, for example, $C_1-C_6$ refers to groups that have 1, 2, 3, 4, 5, or 6 carbon atoms, which encompass $C_1-C_2$, $C_1-C_3$, $C_1-C_5$, $C_2-C_3$, $C_2-C_4$, $C_2-C_5$, $C_2-C_6$, and all like combinations. $(C_1-C_{20})$ and the likes similarly encompass the various combinations between 1 and 20 (inclusive) carbon atoms, such as $(C_1-C_6)$, $(C_1-C_{12})$ and $(C_3-C_{12})$.

The terms "covalent" or "covalently", as used herein, refer to the nature of a chemical bonding interaction between atoms. A covalent bond is a chemical bonding that involves the sharing of electron pairs between atoms. The stable balance of attractive and repulsive forces between atoms when they share electrons is referred to as covalent bonding. The sharing of electrons allows each atom to attain the equivalent of a full outer shell, corresponding to a stable electronic configuration. Covalent bonding includes various kinds of interactions, e.g., σ-bonding, π-bonding, metal-to-metal bonding, agnostic interactions, and three-center two-electron bonds.

The terms "non-covalent" or "non-covalently", as used herein, refer to the nature of a chemical bonding interaction between atoms. A non-covalent bond is a type of chemical bonding that does not involve the sharing of pairs of electrons, but rather involves more dispersed variations of electromagnetic interactions. There are four commonly mentioned types of non-covalent interactions: hydrogen bonds, ionic bonds, van der Waals forces, and hydrophobic interactions.

The terms "purified" or "to purify", as used herein, refer to the removal of components (e.g., contaminants) from a sample.

DETAILED DESCRIPTION

The present disclosure provides novel approaches to reliable synthesis of nucleic acid molecules of greater length than those produced by conventional techniques, while achieving acceptable purity and yield. Aspects of the present disclosure are methods and compositions that make use of phosphorus and/or nucleobase protecting groups that provide for the synthesis of long polynucleotides (e.g., DNA) having a sequence of 200 or more monomeric units in length.

Phosphorus protecting groups are provided that help increase the stepwise coupling yield and/or phosphorous protecting groups that can be removed during the oxidation step. Amidine nucleobase protecting groups are provided that find use in the subject compositions and methods which provides for increased resistance to depurination during polynucleotide synthesis, reduced nucleobase deprotection times, e.g., during polynucleotide cleavage in ammonia, and increased purity of crude oligonucleotides with less byproducts, e.g., nucleobase adducts. In some instances, the methods and compositions disclosed herein may utilize a combination of the phosphorus and nucleobase protecting groups in the synthesis of polynucleotides having a sequence of 200 or more monomeric units in length.

Aspects of the present disclosure include new phosphorus protecting groups that can be removed during iodine oxidation such that the internucleotide bond is less susceptible to hydrolysis reactions (see e.g., the schematic below) that occur during the next oxidation cycles. This novel approach leads to oligonucleotides with fewer large deletions.

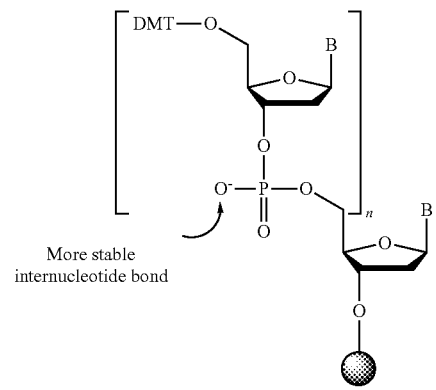

More stable internucleotide bond

Using the protecting groups of the present disclosure on the internucleotide bond also offers the advantage of increased coupling efficiency of the phosphoramidite. The phosphorus protective group most often used for solid-phase phosphoramidite DNA synthesis is the cyanoethyl protective group. (Letsinger, et al. 1969 *J. Am. Chem. Soc.* 91(12), 3360-5). This protecting group is removed via a beta-elimination reaction under the same conditions that the heterobase protecting groups are removed at the end of the synthesis using ammonia or an alkyl amine, as depicted in the following scheme:

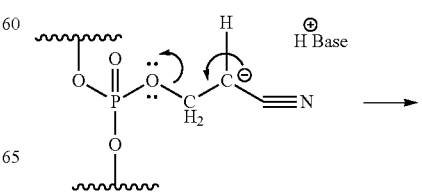

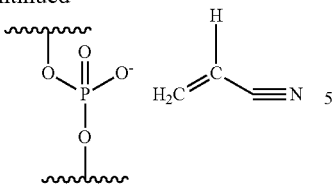

A further aspect of the present disclosure is the design of a phosphorus protecting group that minimizes the hydrolysis of the phosphotriester internucleotide bond that may occur in the practice of the current cyanoethyl phosphoramidite chemistry. Instead, during the iodine oxidation, the phosphotriester internucleotide intermediate is converted—by cleavage of the protecting group—to a phosphodiester internucleotide linkage that is stable to hydrolysis. The cleavage of the phosphorus protecting group can be incomplete, for example as much as 50% but can still have a significant effect on preventing hydrolysis of the internucleotide bond. It is preferred that the cleavage is greater than 50% and more preferred that it is close to 100%. A further aspect of this present disclosure is a protecting group that is cleaved at 50% to 100% during the iodine oxidation and then completely cleaved at the end of the oligonucleotide synthesis by nucleophilic attack using for example a thiolate reagent or derivative thereof or by beta-elimination or alpha fragmentation using a base or basic amines or a combination.

Another aspect of the present disclosure is the addition of a base to the iodine oxidation solution to facilitate and increase the cleavage of the phosphorus protecting group during the oxidation step. Examples of such bases include t-butyl amine, diisopropyl amine, diethyl amine, triethyl amine, diisopropylethyl amine, DBU and other non-nucleophilic bases.

In one aspect, the present disclosure generally relates to a compound having the structural formula (I):

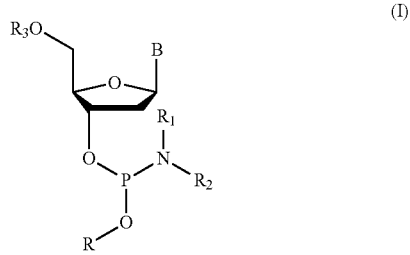

wherein

B is a nucleobase or an analogue thereof;

each of $R_1$ and $R_2$ is independently a linear, branched or cyclic, substituted or un-substituted alkyl, or $R_1$ and $R_2$ together form a 5-, 6-, 7- or 8-membered non-aromatic ring;

$R_3$ is an acid-labile protecting group; and

R is a phosphorus protecting group selected from the group consisting of benzyl alcohol derivatives (except o-methyl benzyl), alpha-methyl aryl alcohols derivatives, naphthalene alcohol derivatives, bi-cyclic aliphatic alcohol derivatives, acylthioalkyl alcohol derivatives, S-ethylthioate derivatives and amino acid derivatives.

In some embodiments, B is a nucleobase or a protected nucleobase, where the nucleobase is selected from Adenine, Guanine, Thymine, Cytosine and Uracil, or a derivative or analog thereof.

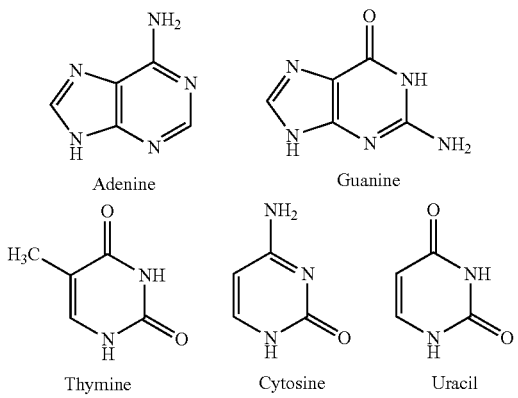

Any convenient protecting groups may be utilized in the subject compounds. In some embodiments, B is a protected nucleobase. In certain embodiments, the nucleobase may be a conventional purine or pyrimidine base, e.g., adenine (A), thymine (T), cytosine (C), guanine (G) or uracil (U), or a protected form thereof, e.g., wherein the base is protected with a protecting group such as acetyl, difluoroacetyl, trifluoroacetyl, isobutyryl, benzoyl, phenoxyacetyl, 4-(t-butyl) phenoxyacetyl and the like. In certain embodiments, the nucleobase includes an amidine protecting group (e.g., as described herein).

The purine or pyrimidine base may also be an analog of the foregoing; suitable analogs include, but are not limited to: 1-methyladenine, 2-methyladenine, $N^6$-methyladenine, $N^6$-isopentyladenine, 2-methylthio-$N^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl) uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

$R_1$ and $R_2$ can be the same or different. $R_1$ and $R_2$ can be both linear, both branched or cyclic, or mixed alkyl groups. $R_1$ and $R_2$ can be both un-substituted alkyls, or one of them is substituted, or both are substituted.

In some cases, $R_1$ and $R_2$ may be components of and together form a 5-, 6-, 7- or 8-membered ring structure (ring Q as shown below), for example, a non-aromatic ring.

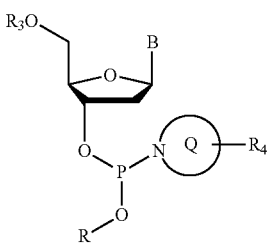

In certain embodiments, each of $R_1$ and $R_2$ independently is a linear, branched or cyclic, substituted or un-substituted $C_1$-$C_{18}$ alkyl. In certain embodiments, each of $R_1$ and $R_2$ independently is a linear or branched un-substituted $C_1$-$C_6$ alkyl. In certain embodiments, each of $R_1$ and $R_2$ independently is a linear $C_1$-$C_3$ alkyl (i.e., methyl, ethyl and propyl). In certain embodiments, each of $R_1$ and $R_2$ independently is a branched $C_3$-$C_6$ alkyl. For example, in the compound of formula ($I_a$), each of $R_1$ and $R_2$ may be isopropyl, as shown in formula ($I_a$), or isobutyl.

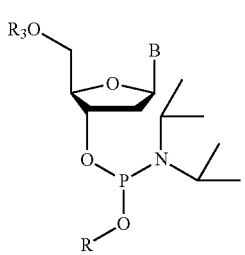

($I_a$)

In certain embodiments, ring Q is a 5- or 6-membered non-aromatic ring, wherein the ring has 0 or 1 hetero-atom in the backbone. In certain embodiments, ring Q is a 5-membered non-aromatic ring with 0 hetero-atom in the backbone. In certain embodiments, ring Q is a 5-membered non-aromatic substituted or unsubstituted cycloalkyl ring.

Structural formula ($I_b$) shows an exemplary embodiment wherein Q is a 5-membered non-aromatic ring. $R_4$ may be any suitable group, for example, each is independently selected from hydrogen, halogen, $C_1$-$C_6$ alkyl and $C_1$-$C_6$ alkyloxy.

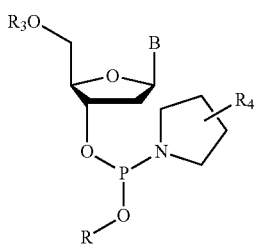

($I_b$)

In certain embodiments, $R_4$ is hydrogen (i.e., unsubstituted ring Q), and the structure is shown as formula ($I_c$)

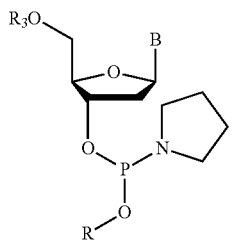

($I_c$)

In some instances, $R_3$ is an acid-labile protecting group. Examples of $R_3$ groups of interest include, but are not limited to, (4,4'-dimethoxytrityl) (DMT), MMT (monomethoxytirtyl), trimethoxy trityl, Pixyl(9-phenylxanthyl) and pivaloyl. (Fisher, et al. 1983 *Nucleic Acids Res.* 11, 1589-1599.)

In some instances, R is a group selected from the group consisting of benzyl alcohol derivatives (except o-methyl benzyl), alpha-methyl aryl alcohols derivatives, naphthalene alcohol derivatives, bi-cyclic aliphatic alcohol derivatives, acylthioalkyl alcohol derivatives and amino acid derivatives. In certain cases, the R is a S-(ethyl)benzothioate.

An acylthioalkyl alcohol derivative includes an acylated thiol group connected to an alkyl group (e.g., R—C(=O)S-alkyl-, where R is a hydrocarbyl, an aryl or a heteroaryl). In certain instances, the alkyl group of the acylthioalkyl alcohol derivative is an ethyl group. As used here, the terms "S-ethylthioate" and "acylthioethyl" are used interchangeably. In some embodiments, the acylthioalkyl alcohol derivative is an S-ethylthioate derivative. In certain cases, the acylthioalkyl alcohol derivative is S-(ethyl)benzothioate. In certain embodiments, the compound of the present disclosure has the structural formula ($I_d$) of:

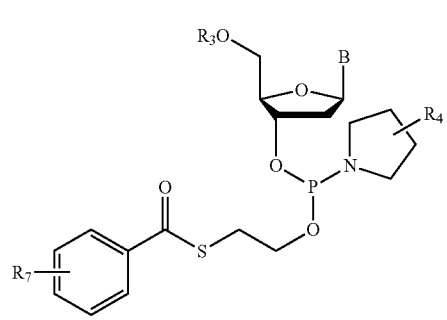

($I_d$)

wherein each $R_7$ is independently selected from hydrogen, halogen, a hydrocarbyl (e.g., $C_1$-$C_6$ alkyl, $C_2$-$C_6$ alkenyl, $C_2$-$C_6$ alkynyl) and an alkyloxy.

In certain embodiments, the compound of the present disclosure has the structural formula ($I_e$):

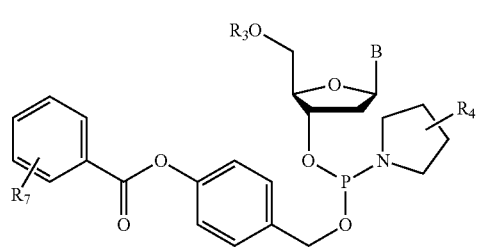

($I_e$)

wherein each $R_7$ is independently selected from hydrogen, halogen, a hydrocarbyl (e.g., $C_1$-$C_6$ alkyl, $C_2$-$C_6$ alkenyl, $C_2$-$C_6$ alkynyl) and an alkyloxy.

In certain embodiments, the compound of the present disclosure has the structural formula ($I_f$):

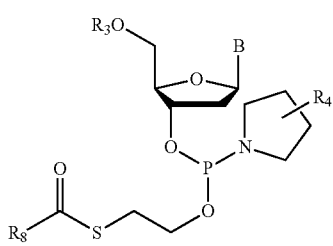

(If)

wherein $R_8$ is an aliphatic group.

In certain embodiments, R (in formula (Ia-c) above) is a derivative of benzyl alcohol (except o-methyl benzyl) having the structural formula (II):

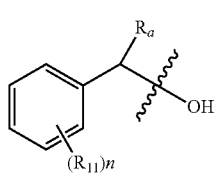

(II)

wherein $R_a$ is hydrogen, or alkyl; each $R_{11}$ is independently hydrogen, alkyl, alkoxy, alkyl-S—, cyano, methylcyano or halogen; and n is 1, 2, or 3. In some embodiments of Formula (II) when $R_a$ is hydrogen, $R_{11}$ is not methyl at the ortho-position.

Exemplary groups from which R may be selected include derivatives of benzyl alcohol such as:

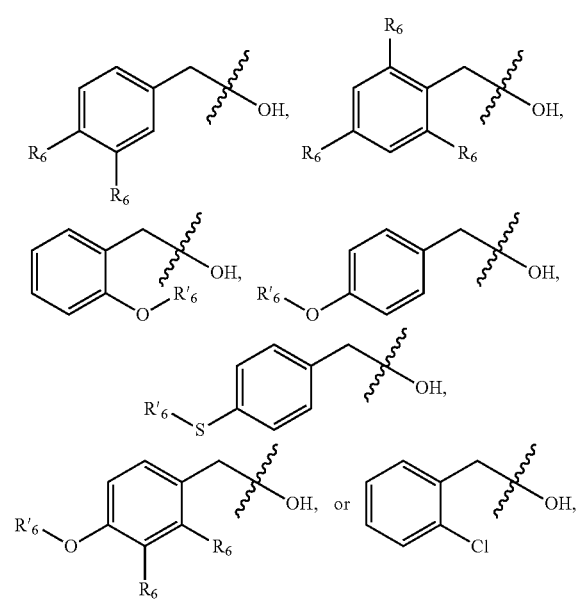

wherein each $R_6$ is independently selected from hydrogen, halogen, cyano, methylcyano, and hydrocarbyl (e.g., $C_1$-$C_6$ alkyl, $C_2$-$C_6$ alkenyl, $C_2$-$C_6$ alkynyl).

In particular, exemplary groups from which R can be derived include:

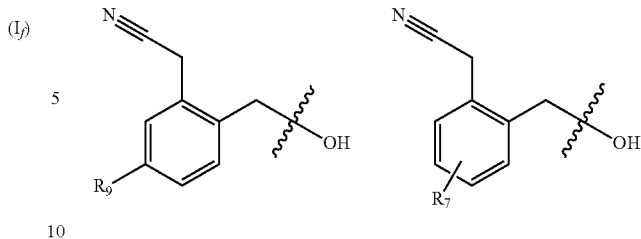

wherein $R_9$ is selected from hydrogen, halogen, cyano, cyanoethyl, $C_1$-$C_6$ alkyl, $C_1$-$C_6$ alkyloxy, nitro and other electron withdrawing groups, $R_7$ is one or more substituent independently selected from hydrogen, halogen, hydrocarbyl (e.g., $C_1$-$C_6$ alkyl, $C_2$-$C_6$ alkenyl, $C_2$-$C_6$ alkynyl), alkyloxy and an electron withdrawing group.

In some embodiments, R is described by the structure:

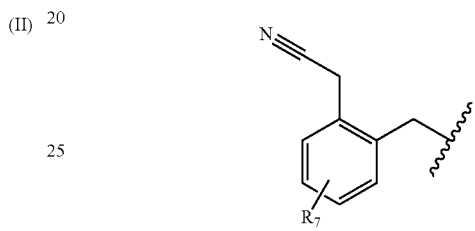

wherein $R_7$ is one or more substituents each independently selected from hydrogen, halogen, hydrocarbyl (e.g., $C_1$-$C_6$ alkyl, $C_2$-$C_6$ alkenyl, $C_2$-$C_6$ alkynyl), alkyloxy and an electron withdrawing group.

In certain embodiments, R is described by the structure:

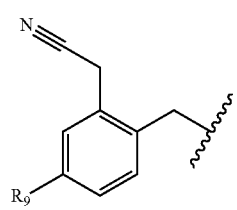

wherein $R_9$ is selected from hydrogen, halogen, cyano, cyanoethyl, $C_1$-$C_6$ alkyl, $C_1$-$C_6$ alkyloxy, nitro and an electron withdrawing group.

Exemplary groups from which R may be derived also include alpha-methyl aryl alcohol derivative having the structural formula (III):

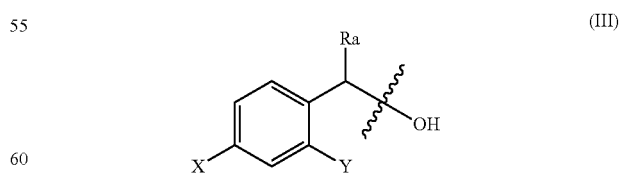

(III)

wherein X is hydrogen, halogen, cyano or trifluoromethyl; Y is hydrogen, alkyl, haloalkyl or alkoxyalkyl; $R_a$ is hydrogen or alkyl. In some embodiments of Formula (III), X and Y are not simultaneously hydrogen and when both $R_a$ and X is hydrogen, Y is not methyl. Exemplary R groups include

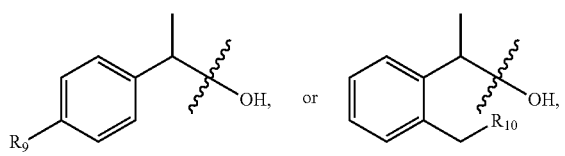

wherein $R_9$ is halogen, cyano, or trifluoromethyl; and $R_{10}$ is selected from hydrogen, halogen, $C_1$-$C_6$ alkyl, $C_1$-$C_6$ alkyloxy, nitro and other electron withdrawing groups.

R may also be derived from naphthalene alcohol derivatives having the structural formula (IV):

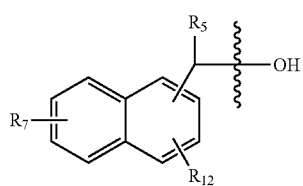

(IV)

wherein $R_7$ is one or more groups, each $R_7$ is independently selected from hydrogen, halogen, cyano, methylcyano, hydrocarbyl (e.g., $C_1$-$C_6$ alkyl, $C_2$-$C_6$ alkenyl, $C_2$-$C_6$ alkynyl) and alkyloxy; $R_5$ is selected from hydrogen and hydrocarbyl (e.g., $C_1$-$C_6$ alkyl, $C_2$-$C_6$ alkenyl, $C_2$-$C_6$ alkynyl); and $R_{12}$ is one or more groups, each $R_{12}$ is independently selected from hydrogen and alkoxy. In certain cases, $R_7$ is a single group and $R_{12}$ is a single group.

Exemplary groups from which R may be derived also include:

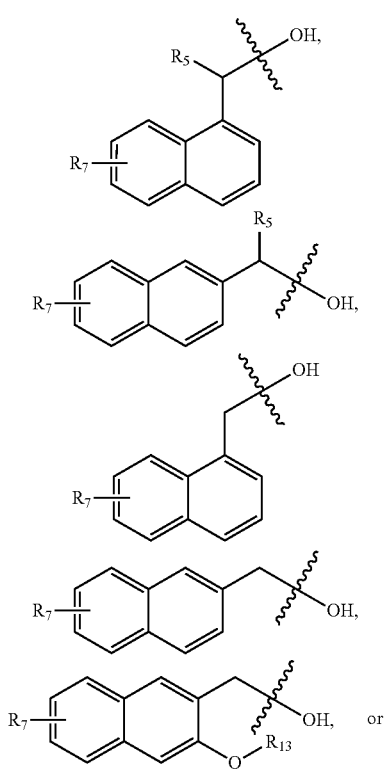

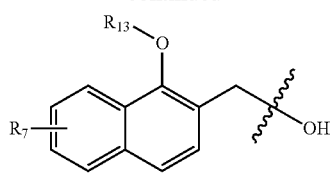

wherein each $R_7$ is independently selected from hydrogen, halogen, cyano, methylcyano, $C_1$-$C_6$ alkyl and $C_1$-$C_6$ alkyloxy; $R_5$ is independently selected from hydrogen and hydrocarbyl (e.g., $C_1$-$C_6$ alkyl, $C_2$-$C_6$ alkenyl, $C_2$-$C_6$ alkynyl); and $R_{13}$ is $C_1$-$C_6$ alkyl, R may also be selected from bi-cyclic aliphatic alcohol derivatives having the structural formula (V) or (VI):

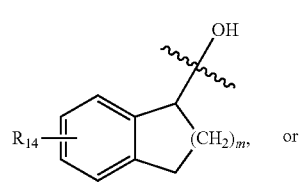

(V)

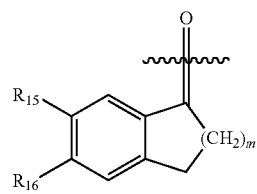

(VI)

wherein $R_{14}$ is selected from hydrogen, halogen, $C_1$-$C_6$ alkyl and $C_1$-$C_6$ alkyloxy; $R_{15}$ and $R_{16}$ are each independently hydrogen, cyano, cyanomethyl, alkoxy, or halogen, and m is 1 or 2.

Exemplary groups from which R may be derived also include:

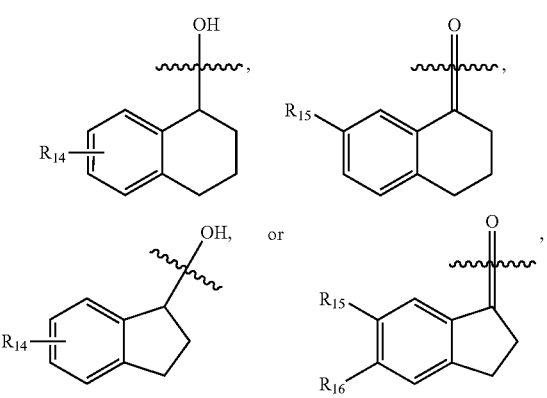

wherein $R_{14}$ is selected from hydrogen, halogen, $C_1$-$C_6$ alkyl and $C_1$-$C_6$ alkyloxy; $R_{15}$ is hydrogen, halogen or $C_1$-$C_6$ alkoxy, $R_{16}$ is hydrogen, cyano, or halogen.

Additionally, exemplary groups from which R may be selected include:

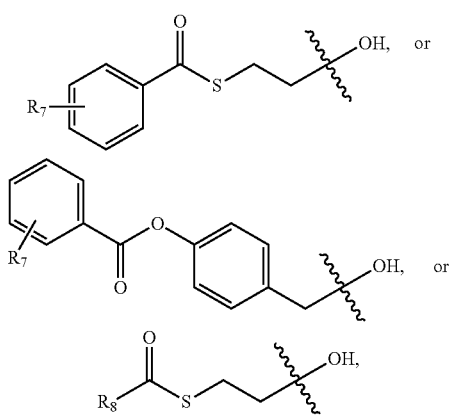

wherein each $R_7$ is selected from hydrogen, halogen, cyano, methylcyano, $C_1$-$C_6$ alkyl and $C_1$-$C_6$ alkyloxy; and $R_8$ is an aliphatic group.

In some embodiments, R is derived from a S-(2-hydroxylethyl)benzothioate-alcohol having the following structure:

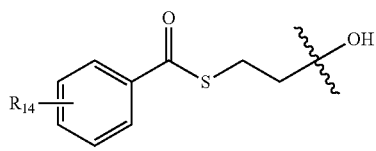

wherein $R_7$ is hydrogen, halogen, cyano, methylcyano, $C_1$-$C_6$ alkyl or $C_1$-$C_6$ alkyloxy.

In some embodiments, R is derived from a S-(2-hydroxylethyl)alkylthioate-alcohol having the following structure:

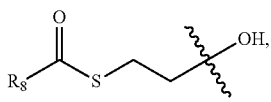

wherein $R_8$ is an aliphatic group.

Additionally, exemplary groups from which R may be selected include:

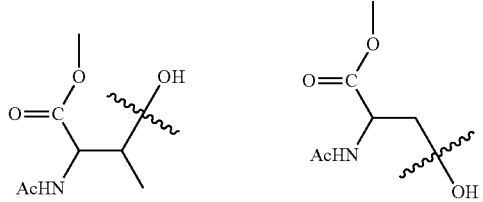

Acetyl-L-threonine methyl ester     Acetyl-L-serine methyl ester

Methods

Aspects of the present disclosure include a method of synthesizing a polynucleotide using the subject compounds. In some embodiments, the method includes: (a) providing a nucleoside residue having an unprotected hydroxyl group; and (b) contacting the nucleoside residue with a nucleoside monomer (e.g., as described herein) to covalently bond the nucleoside monomer to the nucleoside residue and produce the polynucleotide.

In some embodiments, the method further includes exposing the polynucleotide to an oxidizing agent. Any convenient oxidizing agents may be utilized. In some embodiments, the method further includes exposing the nucleic acid to a deprotection agent, e.g., to deprotect the terminal protecting group (e.g., a 3' or a 5'-acid labile protecting group, as described herein) and produce a free hydroxyl terminal capable of further coupling reactions.

In some embodiments, the method further includes reiterating the contacting step at least once. The steps of the method may be repeated until a polynucleotide of a desired length is obtained. In some instances, the cycles of polynucleotide synthesis are repeated 200 times or more, such as 250 times or more, 300 times or more, 400 times or more, 500 times or more, 600 times or more, 700 times or more, 800 times or more, 900 times or more, 1000 times or more, or even more, until a polynucleotide (e.g., a DNA) of a desired length and sequence is obtained.

In some embodiments of the method, the nucleoside residue is covalently bound to a solid support. Any convenient supports may be utilized in the subject methods. Supports of interest include, but are not limited to, planar surfaces such as arrays, beads, and the like. Suitable solid supports are in some cases polymeric, and may have a variety of forms and compositions and derive from naturally occurring materials, naturally occurring materials that have been synthetically modified, or synthetic materials. Examples of suitable support materials include, but are not limited to, polysaccharides such as agarose (e.g., that available commercially as Sepharose®, from Pharmacia) and dextran (e.g., those available commercially under the tradenames Sephadex® and Sephacryl®, also from Pharmacia), polyacrylamides, polystyrenes, polyvinyl alcohols, copolymers of hydroxyethyl methacrylate and methyl methacrylate, silicas, teflons, glasses, and the like. The initial monomer of the polynucleotide to be synthesized on the substrate surface is in some cases bound to a linking moiety which is in turn bound to a surface hydrophilic group, e.g., to a surface hydroxyl moiety present on a silica substrate. In certain embodiments of the method said method further comprises cleaving the nucleic acid from the solid support to produce a free polynucleotide (e.g., a free nucleic acid).

Any convenient polynucleotide synthesis methods, strategies and chemistries may be adapted for use with the subject compositions and methods. Polynucleotide synthesis chemistries and methods of interest that may be adapted for use in the subject methods include, but are not limited to, phosphoramidite, H-phosphonate, phosphodiester, phosphotriester, and phosphite triester, and those methods and materials described in S. L. Beaucage et al. (1981) Tetrahedron Lett. 22:1859, U.S. Pat. No. 6,222,030 to Dellinger et al.; U.S. patent application Publ'n No. US2002/0058802 A1 to Dellinger et al.; and Seio et al. (2001) Tetrahedron Lett. 42 (49):8657-8660.

In certain embodiments, for 3'-to-5' synthesis, a support-bound nucleoside residue is provided having the following structure:

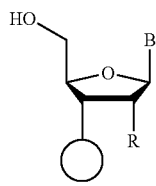

wherein:

represents the solid support (connected via an optional linker) or a support-bound polynucleotide chain;

R is hydrogen, protected hydroxyl group, fluoro, an alkoxy, O-ethyleneoxyalkyl(O—CH$_2$CH$_2$OR), a protected amino, a protected amido, or protected alkylamino wherein when R is hydrogen, the support-bound nucleoside is a deoxyribonucleoside, as will be present in DNA synthesis, and when R is a protected hydroxyl group, the support-bound nucleoside is a ribonucleoside, as will be present in RNA synthesis; and B is a nucleobase or a protected nucleobase, e.g. a purine or pyrimidine base.

In certain embodiments, the nucleobase may be a conventional purine or pyrimidine base, e.g., adenine (A), thymine (T), cytosine (C), guanine (G) or uracil (U), or a protected form thereof, e.g., wherein the base is protected with a protecting group such as acetyl, difluoroacetyl, trifluoroacetyl, isobutyryl, benzoyl, or the like. The purine or pyrimidine base may also be an analog of the foregoing; suitable analogs include, but are not limited to: 1-methyladenine, 2-methyladenine, N$^6$-methyladenine, N$^6$-isopentyladenine, 2-methylthio-N$^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In another aspect, the present disclosure provides a method for synthesizing a DNA using one or more compounds disclosed herein.

In certain embodiments, the synthesized nucleic acid (e.g., a DNA) has a sequence of at least about 150 nucleotides, such as at least about 155 nucleotides, at least about 160 nucleotides, at least about 165 nucleotides, at least about 170 nucleotides, at least about 175 nucleotides, at least about 180 nucleotides, at least about 185 nucleotides, at least about 190 nucleotides, at least about 195 nucleotides, at least about 200 nucleotides, at least about 205 nucleotides, at least about 210 nucleotides, at least about 215 nucleotides, at least about 220 nucleotides, at least about 225 nucleotides, at least about 230 nucleotides, at least about 240 nucleotides, at least about 250 nucleotides, at least about 255 nucleotides, at least about 260 nucleotides, at least about 270 nucleotides, at least about 280 nucleotides, at least about 300 nucleotides. In some instances, any one of the embodiments described above, the synthesized nucleic acid (e.g., a DNA) has a sequence having about 500 nucleotides or less, such as about 400 nucleotides or less, or about 300 nucleotides or less. In certain embodiments, the synthesized DNA has a sequence of at least about 200 nucleotides. In certain embodiments, the synthesized DNA has a sequence of between about 150 and about 500 nucleotides, such as between about 150 and about 400 nucleotides, between about 150 and about 300 nucleotides, or between about 200 and about 300 nucleotides.

In certain embodiments, the synthesized DNA is of a length of about 200-mer to about 1,000-mer, (e.g., containing, inter alia, from about 200-mer to about 800-mer, from about 200-mer to about 500-mer, from about 300-mer to about 800-mer, from about 300-mer to about 500-mer). In certain embodiments, the synthesized DNA has 2 or fewer single nucleotide deletions per 100 nucleotides. In certain embodiments, the synthesized DNA has 1 or less single nucleotide deletions per 100 nucleotides.

In some embodiments, the method further includes coupling a first free nucleic acid with a second free nucleic acid to produce an extended free nucleic acid having a length containing, inter alia, from about 300 to about 10,000 nucleotides. As used herein, the term extended free nucleic acid refers to a free nucleic acids that is produced by fragment condensation of nucleic acid fragments synthesized using the subject linear stepwise synthesis methods. Any convenient nucleic acid fragment coupling methods may be utilized to assembly larger extended nucleic acid molecules from nucleic acids fragments of interest produced by the subject linear stepwise synthesis methods. In certain embodiments, the method further includes coupling (e.g., fragment condensation) of one or more additional free nucleic acids to the extended free nucleic acid to produce a gene.

Aspects of the present disclosure further include the nucleic acid products of the subject methods. The nucleic acid products, e.g., RNA, DNA, of the methods of the disclosure may vary in size, ranging in certain embodiments from 200 or more monomeric units in length, such as 250 or more, 300 or more, 350 or more, 400 or more, 450 or more, 500 or more, or even more. In some embodiments, the nucleic acid products are 200 to 1000 monomeric units in length, including, inter alia, 200 to 500 monomeric units in length, such as 200 to 400 or 300 to 500 monomeric units in length, In certain embodiments, the nucleic acid product has 1 or less (e.g., 1 in 150 nucleotides) single nucleotide deletions per 100 nucleotides and no multiple nucleotide deletions.

As stated before, the synthetic methods of the present disclosure may be conducted on a solid support having a surface to which chemical entities may bind. In some embodiments, multiple oligonucleotides being synthesized are attached, directly or indirectly, to the same solid support and may form part of an array. An "array" is a collection of separate molecules of known monomeric sequence each arranged in a spatially defined and a physically addressable manner, such that the location of each sequence is known. The number of molecules, or "features," that can be contained on an array will largely be determined by the surface area of the substrate, the size of a feature and the spacing between features, wherein the array surface may or may not comprise a local background region represented by non-feature area. Arrays can have densities of up to several hundred thousand or more features per cm$^2$, such as 2,500 to 200,000 features/cm$^2$. The features may or may not be covalently bonded to the substrate. An "array," or "chemical array' used interchangeably includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "probe" may be the one which is to be evaluated by the other (thus, either one could be an unknown mixture of analytes, e.g., polynucleotides, to be evaluated by binding with the other).

In some embodiments, the array is part of a microfluidic device, and is two or three-dimensional. The solid support comprising such an array, may be substantially planar or may comprise a plurality of microstructures, such as wells, channels and microchannels, elevated columns or posts.

In some embodiments, oligonucleotides being synthesized are attached to a bead directly or indirectly. The beads may optionally be placed in an array of wells or channels. Suitable solid supports may have a variety of forms and compositions and derive from naturally occurring materials, naturally occurring materials that have been synthetically modified, or synthetic materials.

Examples of suitable support materials include, but are not limited to, silicas, silicon and silicon oxide (including any materials used in semiconductor fabrication), teflons, glasses, polysaccharides such as agarose (e.g., Sepharose® from Pharmacia) and dextran (e.g., Sephadex® and Sephacryl®, also from Pharmacia), polyacrylamides, polystyrenes, polyvinyl alcohols, copolymers of hydroxyethyl methacrylate and methyl methacrylate, and the like. The initial monomer of the oligonucleotide to be synthesized on the substrate surface is typically bound to a linking moiety which is in turn bound to a surface hydrophilic group, e.g., a surface hydroxyl moiety present on a silica substrate. In some embodiments, a universal linker is used. In some other embodiments, the initial monomer is reacted directly with, e.g., a surface hydroxyl moiety. Alternatively, oligonucleotides can be synthesized first according to the present disclosure, and attached to a solid substrate post-synthesis by any method known in the art. Thus, the present disclosure can be used to prepare arrays of oligonucleotides wherein the oligonucleotides are either synthesized on the array, or attached to the array substrate post-synthesis.

With the efficiency and ease of the present method, oligonucleotide synthesis can be performed in small or large scales. The quantity of oligonucleotide made in one complete run of the present method (in one container) can thus be less than a microgram, or in micrograms, tens of micrograms, hundreds of micrograms, grams, tens of grams, hundreds of grams, or even kilograms.

In some embodiments, an array of nucleic acids is synthesized by the method and compositions of the present disclosure. In some embodiments, the nucleic acids are kept attached to the array for their use in array-based applications (such as for example gene expression, cytogenetics, genotyping, transcripts or exons profiling etc.). In other embodiments, the nucleic acids are all- or sometime only a subset-released from the solid support to produce a library or libraries of nucleic acids, or pools that can be optionally amplified prior or after cleavage from the solid support. Pools or libraries of nucleic acids can be used for example as baits for selective target enrichment, or used as probes for in situ hybridization assays (e.g. o-FISH) or other hybridization assays, multiplex site-directed mutagenesis, multiplex genome engineering and accelerated evolution (MAGE), genes knockout with libraries encoding siRNAs, shRNAs, miRNAs, genome engineering with libraries of nucleic acids encoding CRISPR RNAs and/or Cas proteins, or the nucleic acids encoding genes or genes fragments can be further assembled and ligated in to longer DNA fragments, genes and/or genome. In some embodiments, the assembled nucleic acids are DNA having a length from about 300 nucleotides to about 10,000 nucleotides. In other embodiments, the length of the assembled nucleic acids may vary in size, ranging in certain embodiments from 300 or more nucleotides in length, such as 400 or more, 1,000 or more, 2,000 or more, 3,000 or more, 4,000 or more, 5,000 or more, 6,000 or more, 8,000 or more, 10,000 or more, or even more.

Also provided is a library of nucleic acids produced using the subject compositions and methods. In some embodiments of the library, the library includes a plurality of nucleic acids, where each nucleic acid is synthesized by a subject method as described herein. Also provided is a library including a plurality of nucleic acids having a length from about 300 to about 10,000 nucleotides, wherein each nucleic acid is composed of assembled nucleic acid fragments synthesized by a subject method as described herein. The nucleic acids may be free nucleic acids. The plurality of nucleic acids may have sequences that together define a gene of interest. The plurality of nucleic acids of the library may be assembled into a gene, e.g., using any convenient methods of fragment coupling.

The product nucleic acids find use in a variety of applications, including research, diagnostic and therapeutic applications. For example, the product nucleic acids find use in research applications such as genomics, cytogenetics, target enrichment and sequencing, site-directed mutagenesis, synthetic biology, gene synthesis, gene assembly, e.g., as probes, primers, gene fragments, DNA/RNA arrays, libraries of nucleic acids. With respect to diagnostic applications, such as genomics, cytogenetics, oncology, infectious diseases, non-invasive prenatal testing (NIPT), target enrichment and sequencing, the product nucleic acids may also find use as probes (for example oligoFISH), primers, gene fragments, transcripts, DNA/RNA arrays, libraries of nucleic acids, libraries of transcripts or other agents employed in diagnostic protocols. With respect to therapeutic applications, the product nucleic acids find use as any DNA, RNA or other nucleic acid therapeutic, such as antisense nucleic acids, in gene therapy applications, gene editing, interfering RNA (i.e., iRNA or RNAi) applications, etc.

EXAMPLES

The following examples illustrate the general synthetic strategy of compounds (22-54) described herein.

Synthesis of various 5'-O-Dimethoxytrityl-2'-deoxy-ribothymidine 3'-O-arylphosphoramidite

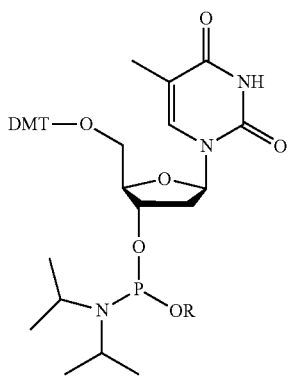

Bis(N,N-diisopropylamino)chlorophosphine (Chem Genes, 0.019 mols, 5.20 grams) was dissolved in anhydrous dichloromethane (20 mL) in a flame-dried 250-mL Schlenk flask equipped with a magnetic stir bar and septum under argon. To this solution 5'-O-dimethoxytrityl-2'-deoxyribothymidine (Chem Genes, 0.019 mols, 1.0 equiv) was added. When the 2'-deoxyribonucleoside was completely dissolved, N,N-Diisopropylethylamine (Sigma Aldrich, 0.057 mol, 3.0 equiv) was added and the mixture was allowed to stir under argon at room temperature for thirty minutes. The 31P NMR spectrum after thirty minutes indicated complete conversion of the starting material to product. After the solvent was removed in vacuo, the crude product was isolated by chromatography using a 50-90% gradient of ethyl acetate in hexane containing 1% triethylamine. 31P NMR (CDCl3): δ 115.9 (s).

5'-O-Dimethoxytrityl-2'-deoxyribothymidine 3'-O-phosphorodiamidite (2.58 mmols, 2 grams) and the aryl alcohol (1.0 equiv.) were dissolved in anhydrous dichloromethane (15 mL) in a 100 mL round-bottom flask and stirred under argon at room temperature. 1H-Ethylthiotetrazole (0.25 M in anhydrous acetonitrile, Glen Research, VA, 1.0 equiv.) was added dropwise to the mixture via a syringe over a period of 15 min and the mixture was allowed to stir under nitrogen at room temperature until TLC analysis showed the complete conversion of the starting material to an higher running spot. The solvent was removed in vacuo, the crude product was isolated by chromatography using a 50-90% gradient of ethyl acetate in hexane containing 1% triethylamine.

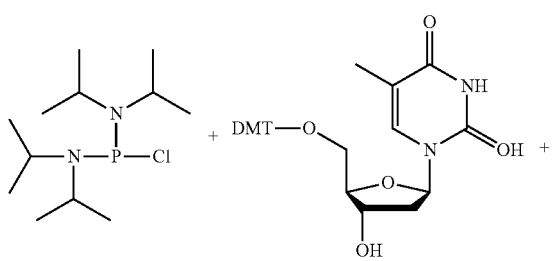

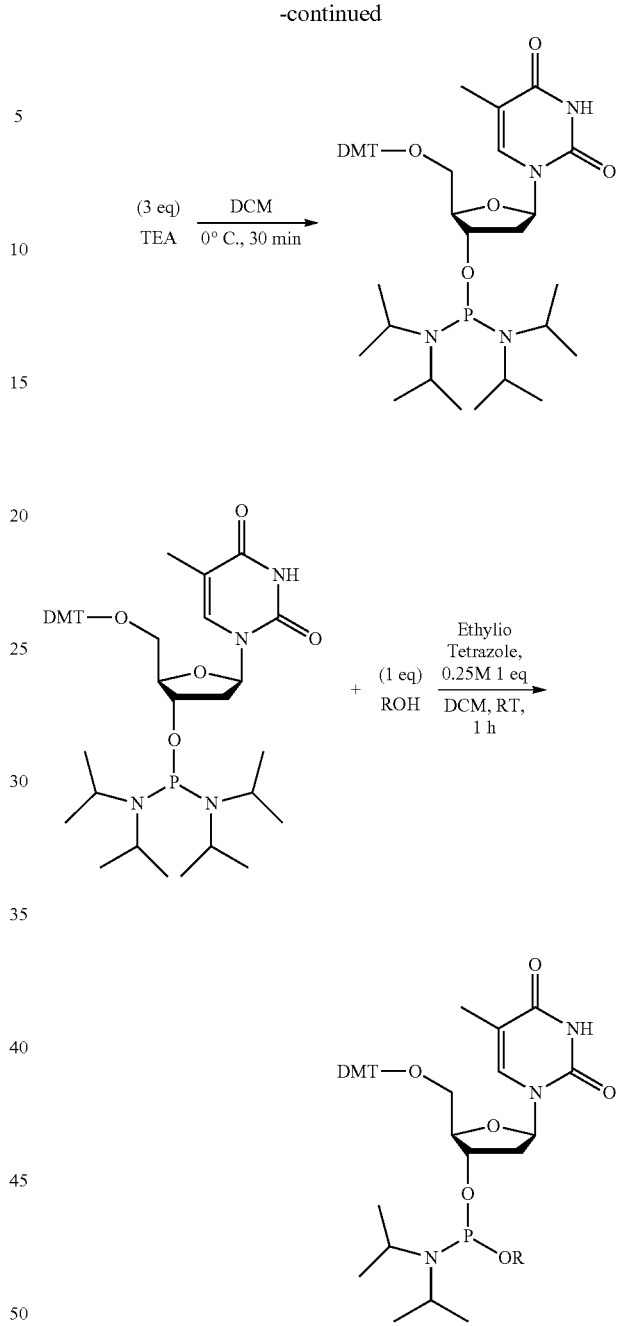

TABLE 1

Phosphorus protecting groups partially removable during oxidation step (e.g., protecting group R of Formula (I))

| Naphtalene motif | |
|---|---|
| | 24 (31P NMR: δ 148.7, 147.9) |

TABLE 1-continued
Phosphorus protecting groups partially removable during oxidation step (e.g., protecting group R of Formula (I))
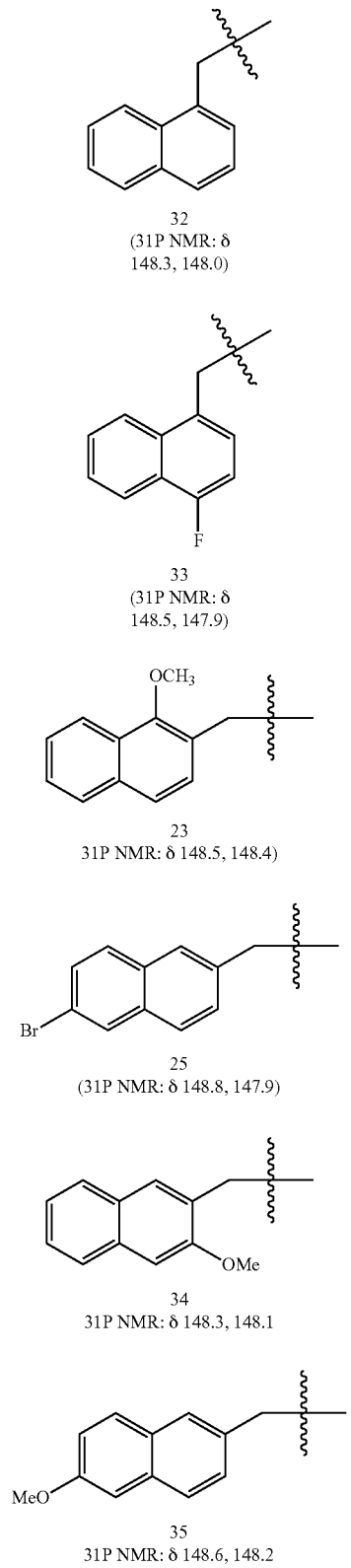
32
(31P NMR: δ 148.3, 148.0)
33
(31P NMR: δ 148.5, 147.9)
23
31P NMR: δ 148.5, 148.4)
25
(31P NMR: δ 148.8, 147.9)
34
31P NMR: δ 148.3, 148.1
35
31P NMR: δ 148.6, 148.2
TABLE 1-continued
Phosphorus protecting groups partially removable during oxidation step (e.g., protecting group R of Formula (I))
Alpha methyl motif
36
(31P NMR: δ 146.9, 146.4, 146.0)
22
(31P NMR: δ 146.9, 146,4, 146.0)
37
(31P NMR: δ 146.6, 146.3, 145.9)
38
(31P NMR: δ 147.1, 146.5, 146.0)
39
(31P NMR: δ 147.0, 146.9, 146.2, 146.0)
Benzyl motif
40
(31P NMR: δ 147.9)

TABLE 1-continued

Phosphorus protecting groups partially removable during oxidation step (e.g., protecting group R of Formula (I))

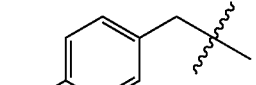

27
(31P NMR: δ 148.9, 148.5)

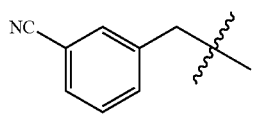

28
(31P NMR: δ 149.1, 148.6)

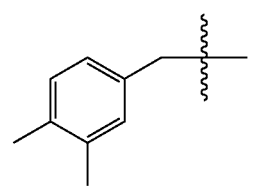

41
(31P NMR: δ 148.0, 147.6)

42
(31P NMR: δ 148.0, 147.9)

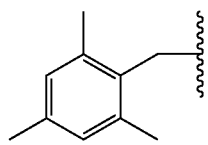

43
(31P NMR: δ 148.0, 147.5)

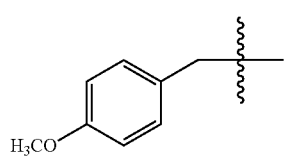

44
(31P NMR: δ 148.04, 148.00)

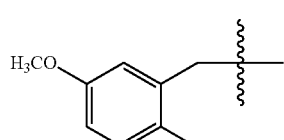

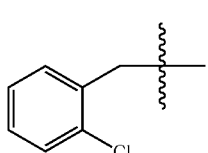

45
(31P NMR: δ 148.5)

TABLE 1-continued

Phosphorus protecting groups partially removable during oxidation step (e.g., protecting group R of Formula (I))

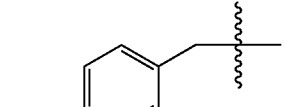

46
(31P NMR: δ 148.2, 147.7)

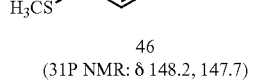

29
(31P NMR: δ 148.23, 148.20)

Bicyclic aliphatic motif Fused rings

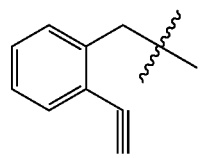

26
(31P NMR: δ 148.7, 148.2, 148.0, 147.8)

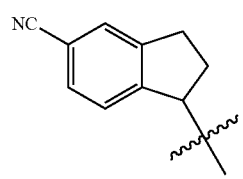

47
(31P NMR: δ 149.1, 149.0, 148.9, 148.8)

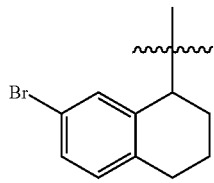

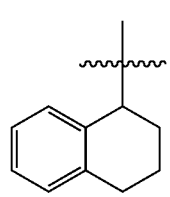

48
(31P NMR: δ 148.3, 148.1, 147.8, 147.2)

TABLE 1-continued

Phosphorus protecting groups partially removable during oxidation step (e.g., protecting group R of Formula (I))

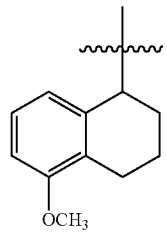

49
(31P NMR: δ 148.6, 148.2, 147.7, 147.3)

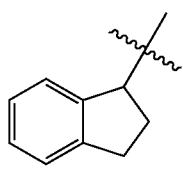

50
(31P NMR: δ 148.2, 147.5, 147.4, 146.8)

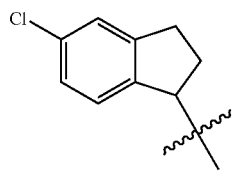

51
(31P NMR: δ 148.1, 147.4, 147.82)

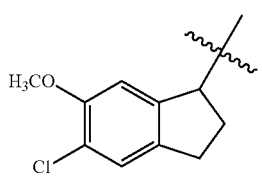

52
(31P NMR: δ 148.4, 147.9, 147.0, 146.9)

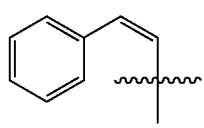

53
(31P NMR: δ 149.2, 148.5)

TABLE 2

Phosphorus protecting groups removable during ammonia cleavage (e.g., protecting group R of Formula (I))

Acetyl-L-threonine methyl ester (30)

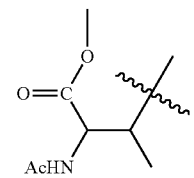

30
(31P NMR: δ 148.4, 147.0)

Acetyl-L-Serine methyl ester (54)

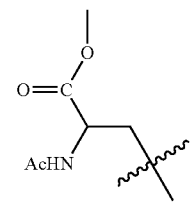

54

S-ethyl benzothioate (31)

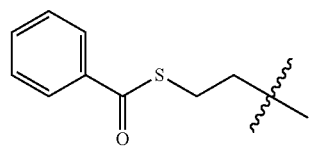

31
(31P NMR: δ 148.2, 147.6

Synthesis of various 5'-O-Dimethoxytrityl-2'-deoxy-ribothymidine 3'-O—S-(ethyl)benzothioate-pyrrolidinylphosphoramidite

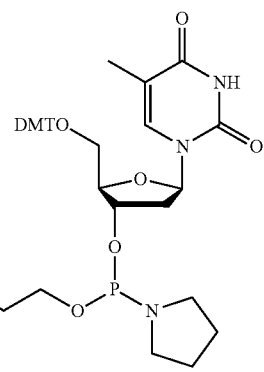

Tris(1-pyrrolidinyl)phosphine (0.016 mols, 4 grams) was dissolved in anhydrous dichloromethane (20 mL) in a 100 mL round-bottom flask and stirred under argon at room temperature. To this solution 5'-O-dimethoxytrityl-2'-deoxy-ribothymidine (Chem Genes, 0.016 mols, 1.0 equiv.) was added. In the end 1H-Ethylthiotetrazole (0.25 M in anhydrous acetonitrile, Glen Research, VA, 1.0 equiv) was added dropwise to the mixture via a syringe over a period of 15 min and the mixture was allowed to stir under nitrogen at room temperature for thirty minutes when the 31P NMR spectrum indicated complete conversion of the starting material to product. The solvent was removed in vacuo, the crude product was isolated by chromatography using a 30-60% gradient of ethyl acetate in dichloromethane containing 1% triethylamine. 31P NMR (CDCl3): δ 135.2 (s).

5'-O-Dimethoxytrityl-2'-deoxyribothymidine 3'-O-bis(1-pyrrolidinyl)phosphorodiamidite (2.80 mmols, 2 grams) and the thioester (1.0 equiv) were dissolved in anhydrous dichloromethane (15 mL) in a 100 mL round-bottom flask and stirred under argon at room temperature. 1H-Ethylthiotetrazole (0.25 M in anhydrous acetonitrile, Glen Research, VA, 1.0 equiv) was added dropwise to the mixture via a syringe over a period of 15 min and the mixture was allowed to stir under nitrogen at room temperature until TLC analysis showed the complete conversion of the starting material to an higher running spot. The solvent was removed in vacuo, the crude product was isolated by chromatography using a 30-60% gradient of ethyl acetate in dichloromethane containing 1% triethylamine. 31P NMR (CDCl3): δ 144.1, 144.3 (d)

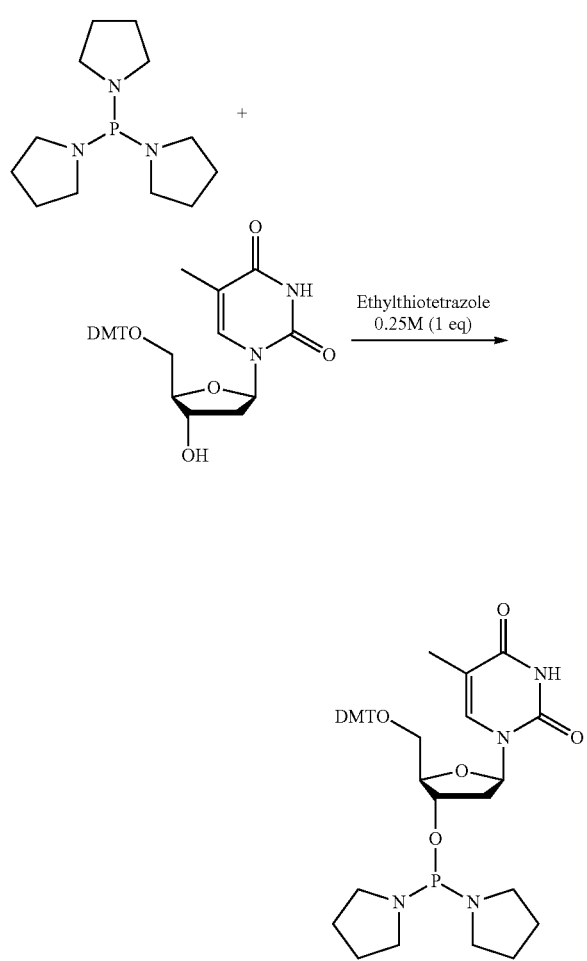

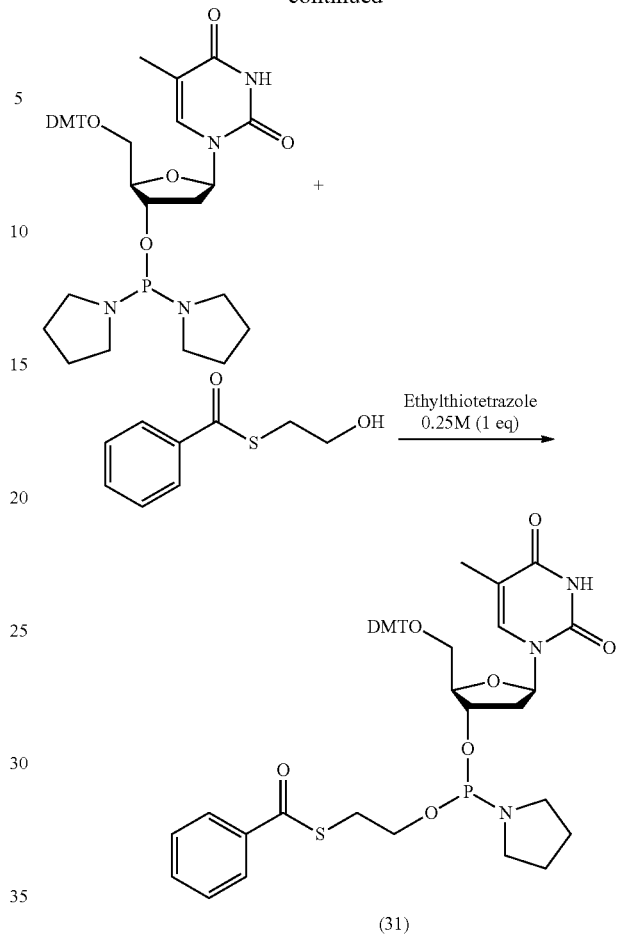

(31)

General Procedure for Solid-Phase Oligonucleotide Synthesis

Synthesis is performed on 0.2 (60mer) and 1.0 micromole (20mer) scale using dT-CPG columns (500 Angstrom for 20mer and 1000 Angstrom for 60mer) from Glen Research according to the standard DNA cycle on an ABI model 394 automated DNA synthesizer. The synthetic protocol was based on the conventional DMT phosphoramidite method. All protected deoxyribothymidine 3'-O-arylphosphoramidite were dissolved in anhydrous acetonitrile at a concentration of 100 mM and placed on the appropriate ports of the synthesizer. Prior to synthesis, the 5'-DMT group on the support-bound 2'-deoxyribonucleoside was removed with 3% dichloroacetic acid in dichloromethane. The activator was 5-ethylthio-1H-tetrazole (0.25 M in anhydrous acetonitrile, Glen Research, VA). After each condensation step, the support was washed with acetonitrile for 40 s and Unicap phosphoramidite (Glen Research, VA) was used according to the manufacturer's recommendations for capping failure sequences. The standard oxidation reagent (0.02 M iodine in THF/water/pyridine) was used for oxidation. Postsynthesis oligomers were cleaved from solid support by treatment with Ammonia (Macron, solution with 10-35% Ammonia). In several cases, before the cleavage, the oligonucleotide still joined to CPG was treated with 1 M solution of 2-carbamoyl-2-cyanoethylene-1,1-dithiolate in DMF (1 mL) for 4 to 8 hours. The resin was then washed with DMF followed by MeOH and dried under argon and finally cleaved with ammonia. The cleavage mixture was discarded and the solid-support was evaporated to dryness in a Speed-Vac. The ODN product adsorbed on the support was dissolved in water and analyzed by LC-MS.

LC-MS Analysis of Crude Oligonucleotides

Analysis of 20mers and 60mers were performed on Agilent 6530 Accurate-Mass Q-TOF LC/MS in negative mode. Data were processed with Agilent Mass Hunter Qualitative Analysis B 04.00 software.

Two different reverse phase columns were used: ACQUITY UPLC BEH C18, 1.7 µm, 2.1×100 nm Column for the analysis of 20mers and ACQUITY UPLC PrST C4, 1.7 µm, 2.1 mm×150 mm, Column for the analysis of 60mers. More than one eluent system and several gradients were used:

Eluent System 1

Buffer A: 200 mmHFIP, 8 mMTEA, 5% Methanol in water
Buffer B: 90% Methanol in water Eluent System 2

Buffer A: 5 mM Dibutylammonium Acetate, 5% Organic component in water
Buffer B: 5 mM Dibutylammonium Acetate, 10% water in Organic component
Organic Component: 1:1 Acetonitrile: 2-Isopropanol

TABLE 3

| Gradient 1 | | |
| --- | --- | --- |
| Time (min) | % Buffer B | Flow (mL/min) |
| 0.0 | 5.0 | 0.2 |
| 3.0 | 5.0 | 0.2 |
| 30.0 | 50.0 | 0.2 |
| 45.0 | 80.0 | 0.2 |
| 47.0 | 5.0 | 0.2 |
| 70.0 | 5.0 | 0.2 |

TABLE 4

| Gradient 2 | | |
| --- | --- | --- |
| Time (min) | % Buffer B | Flow (mL/min) |
| 0.0 | 15.0 | 0.2 |
| 15.0 | 25.0 | 0.2 |
| 30.0 | 45.0 | 0.2 |
| 35.0 | 60.0 | 0.2 |
| 40.0 | 15.0 | 0.2 |
| 45.0 | 15.0 | 0.2 |

TABLE 5

| Gradient 3 | | |
| --- | --- | --- |
| Time (min) | % Buffer B | Flow (mL/min) |
| 0.0 | 5.0 | 0.2 |
| 30.0 | 25.0 | 0.2 |
| 35.0 | 60.0 | 0.2 |
| 40.0 | 10.0 | 0.2 |
| 45.0 | 5.0 | 0.2 |
| 50.0 | 5.0 | 0.2 |

All the samples were run in negative mode and the following is a list of all the mass parameters used.

TABLE 6

| Source Parameters | | | | | |
| --- | --- | --- | --- | --- | --- |
| AJS ESI (seg) | | AJS Exp | | MS TOF (Exp) | |
| Gas Temp | 325° C. | V Cap | 3800 V | Fragmentor | 175 V |
| Drying Gas | 9 l/min | Nozzle Voltage (exp) | 100 V | Skimmer | 65 V |
| Nebulizer | 20 psig | | | OctopoleRF Vpp | 750 V |
| Sheat Gas Temp | 250° C. | | | | |
| Sheat Gas Flow | 11 l/min | | | | |

All the samples were processed with the MassHunter Qualitative Analysis software to extract chromatograms from various signal types as Total Ion Chromatogram (TIC), DAD Chromatogram and Extracted Ion Chromatogram (EIC).

The following examples illustrate the analysis of 20mers and 60mers by using phosphoramidites (22-31) described herein. In particular each oligonucleotide has been analyzed by TIC, DAD and EIC Chromatograms.

dT₂₀ Using 5'-O-Dimethoxytrityl-2'-deoxyribothymidine 3'-O-α-methyl-p-bromobenzylphosphoramidite (22)

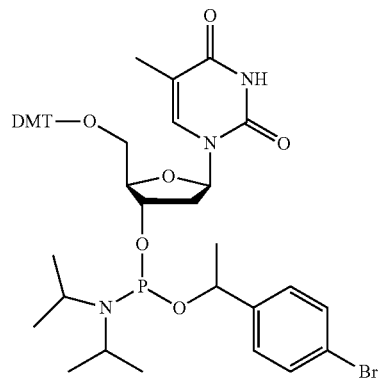
(22)

TIC, DAD chromatograms and Mass analysis of dT₂₀ using 1-(4-Bromophenyl)Ethanol as phosphorus protecting group are shown in FIG. 1.

dT₂₀ Using 5'-O-Dimethoxytrityl-2'-deoxyribothymidine 3'-O-1-methoxynaphtalenephosphoramidite (23)

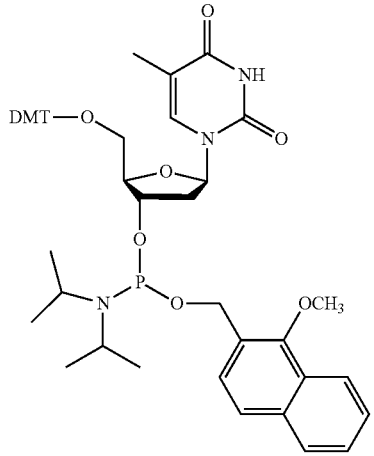
(23)

Figure 2:
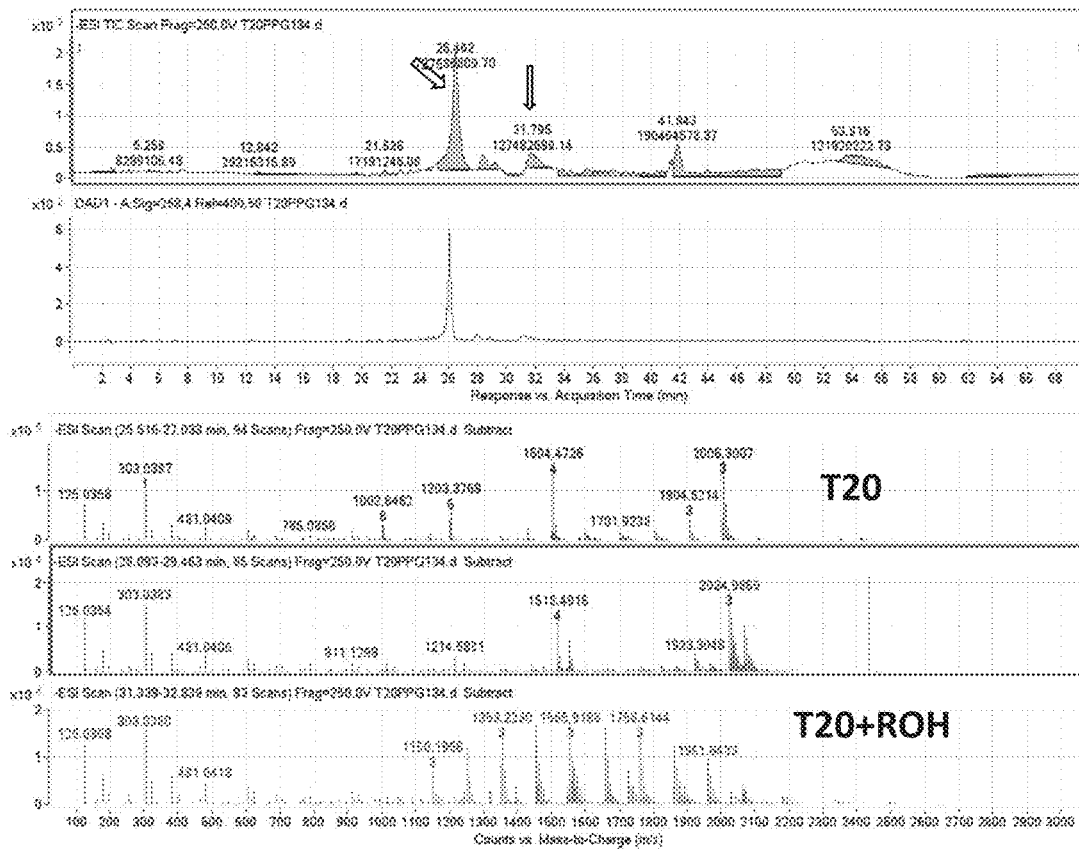
FIG. 2 shows TIC and HPLC chromatograms and Mass analysis of the synthesis of $dT_{20}$ using 1-methoxy-2-naphtalenemethanol as phosphorus protecting group.

TIC, DAD chromatograms and Mass analysis of dT20 using 1-methoxy-2-naphtalenemethanol as phosphorus protecting group are shown in FIG. 2.

dT20 Using 5'-O-Dimethoxytrityl-2'-deoxyribothymidine 3'-O-Naphtalenephosphoramidite (24)

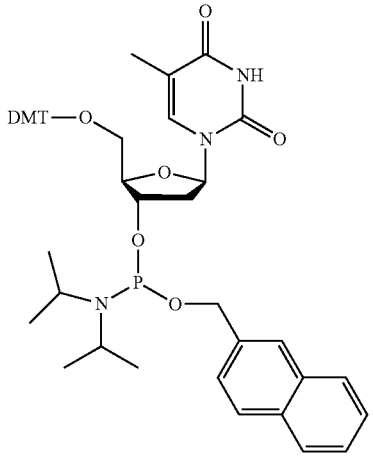
(24)

Figure 3:
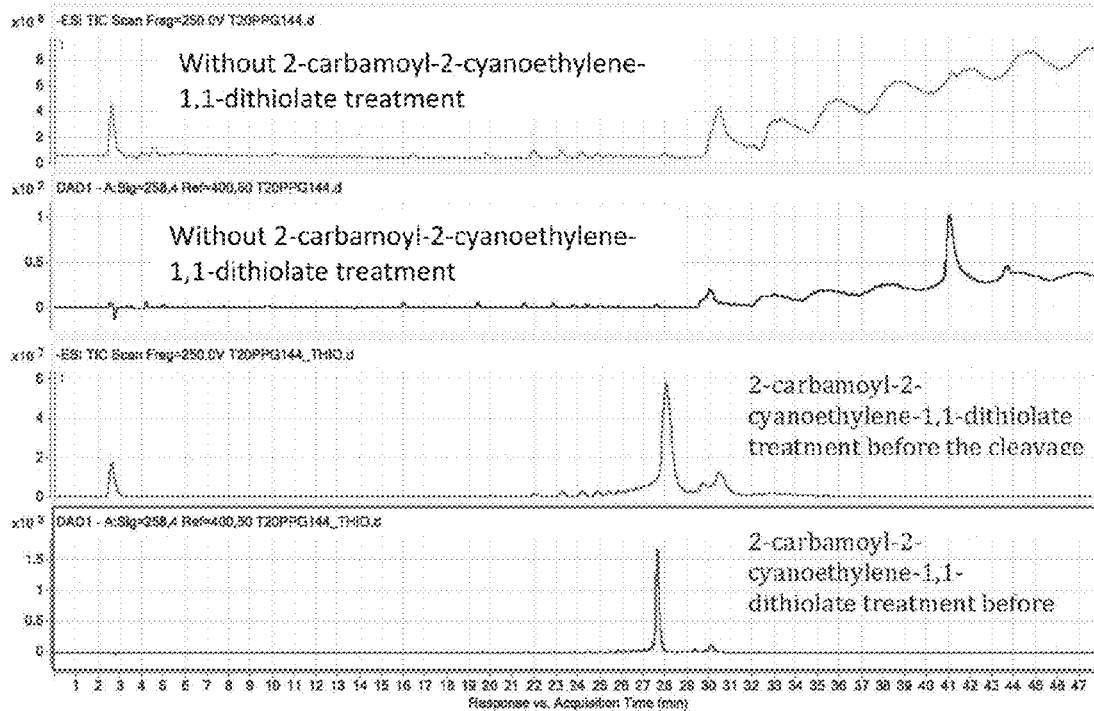
FIG. 3 shows TIC and HPLC chromatograms and Mass analysis of the synthesis of $dT_{20}$ using 2-naphtalenemethanol as phosphorus protecting group with a 2-carbamoyl-2-cyanoethylene-1,1-dithiolate treatment.
Figure 3:
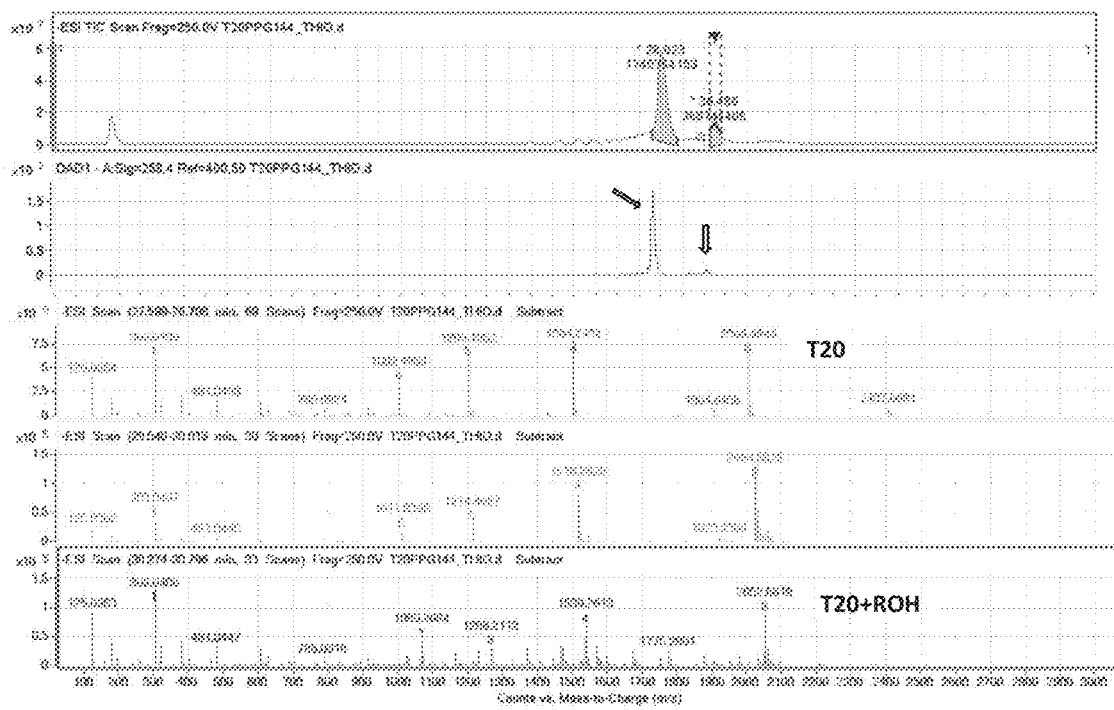

TIC, DAD chromatograms and mass analysis of dT₂₀ using 2-naphtalenemethanol as phosphorus protecting group with a 2-carbamoyl-2-cyanoethylene-1,1-dithiolate treatment are shown in FIG. 3.

dT₂₀ Using 5'-O-Dimethoxytrityl-2'-deoxyribothymidine 3'-O-6-Bromo-2-naphtalenehosphoramidite (25)

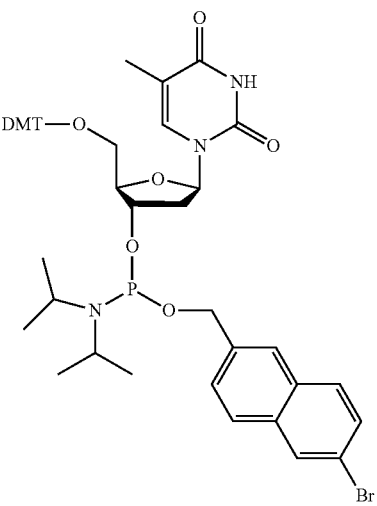
(25)

Figure 4:
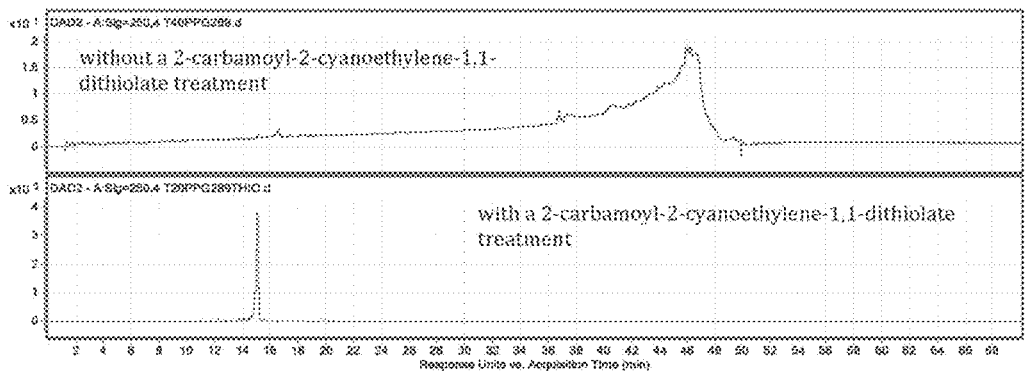
FIG. 4 shows TIC and HPLC chromatograms and Mass analysis of the synthesis of $dT_{20}$ using 6-Bromo-2-naphtalenemethanol as phosphorus protecting group with a 2-carbamoyl-2-cyanoethylene-1,1-dithiolate treatment.
Figure 4:
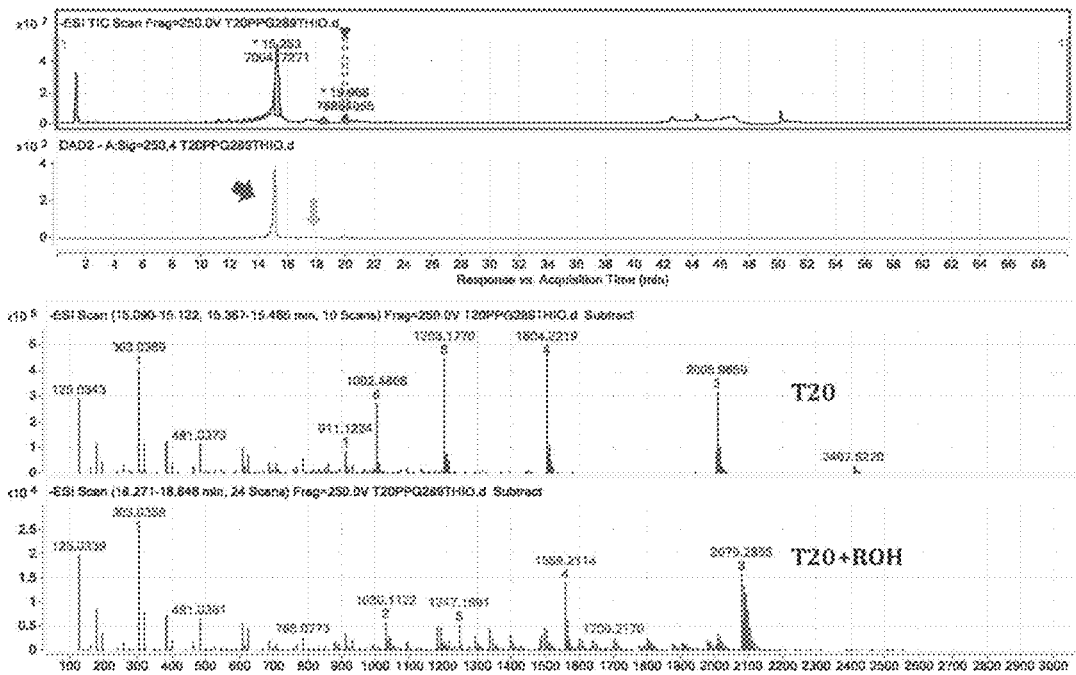

TIC, DAD chromatograms and mass analysis of dT20 using 6-Bromo-2-naphtalenemethanol as phosphorus protecting group with a 2-carbamoyl-2-cyanoethylene-1,1-dithiolate treatment are shown in FIG. 4.

dT$_{20}$ by Using 5'-O-Dimethoxytrityl-2'-deoxyribo-thymidine 3'-O-1-indane-5-carbonitrilephosphoramidite (26)

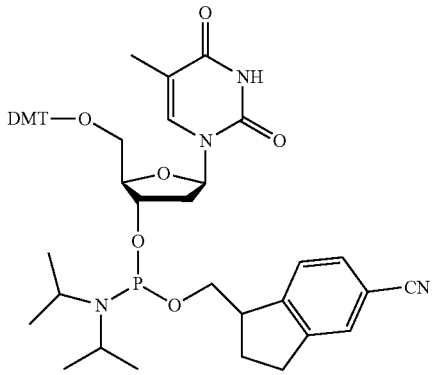
(26)

Figure 5:
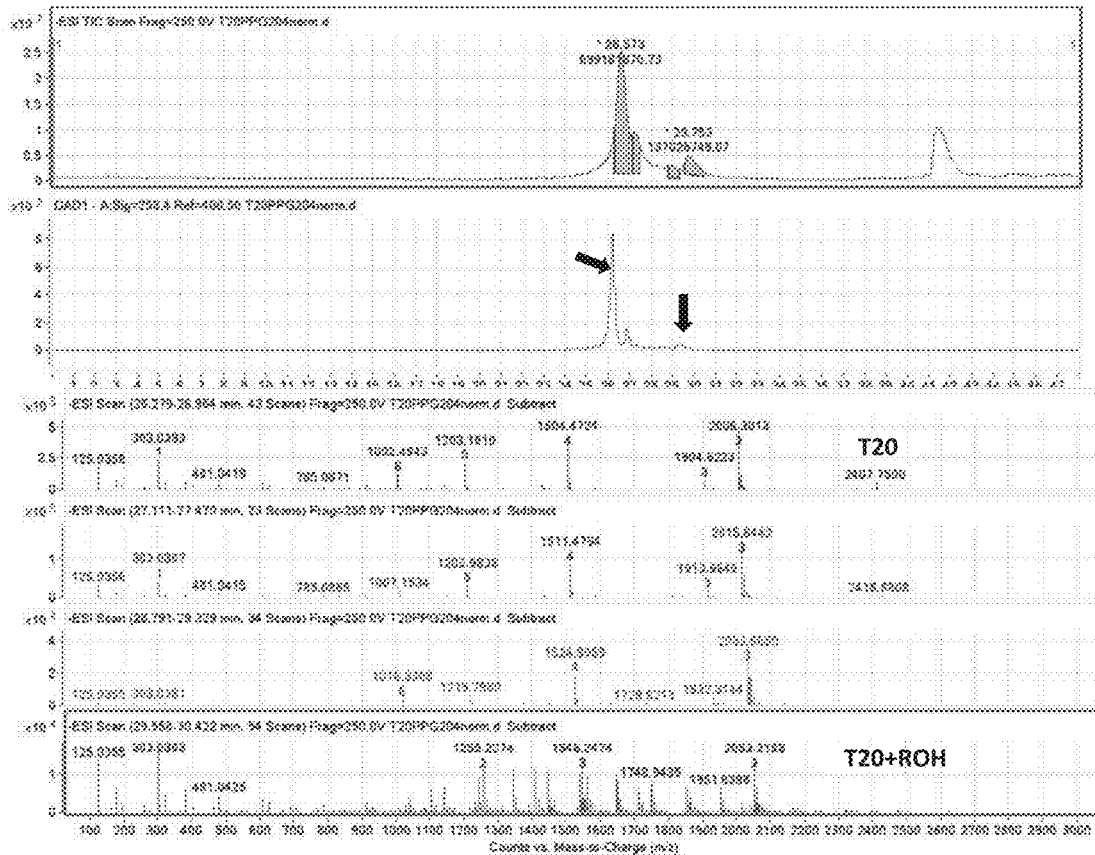
FIG. 5 shows TIC and HPLC chromatograms and Mass analysis of the synthesis of $dT_{20}$ using 1-hydroxyindane-5-carbonitrile as phosphorus protecting group.

TIC, DAD chromatograms and Mass analysis of dT$_{20}$ using 1-hydroxyindane-5-carbonitrile as phosphorus protecting group are shown in FIG. 5.

dT$_{20}$ Using 5'-O-Dimethoxytrityl-2'-deoxyribothymidine 3'-O-4-cyanobenzylphosphoramidite (27)

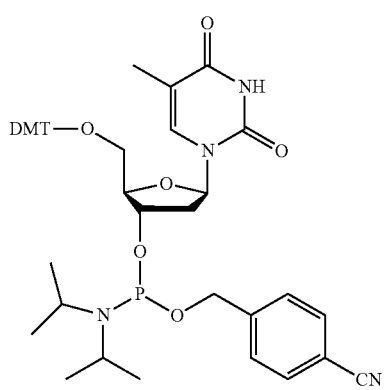
(27)

Figure 6:
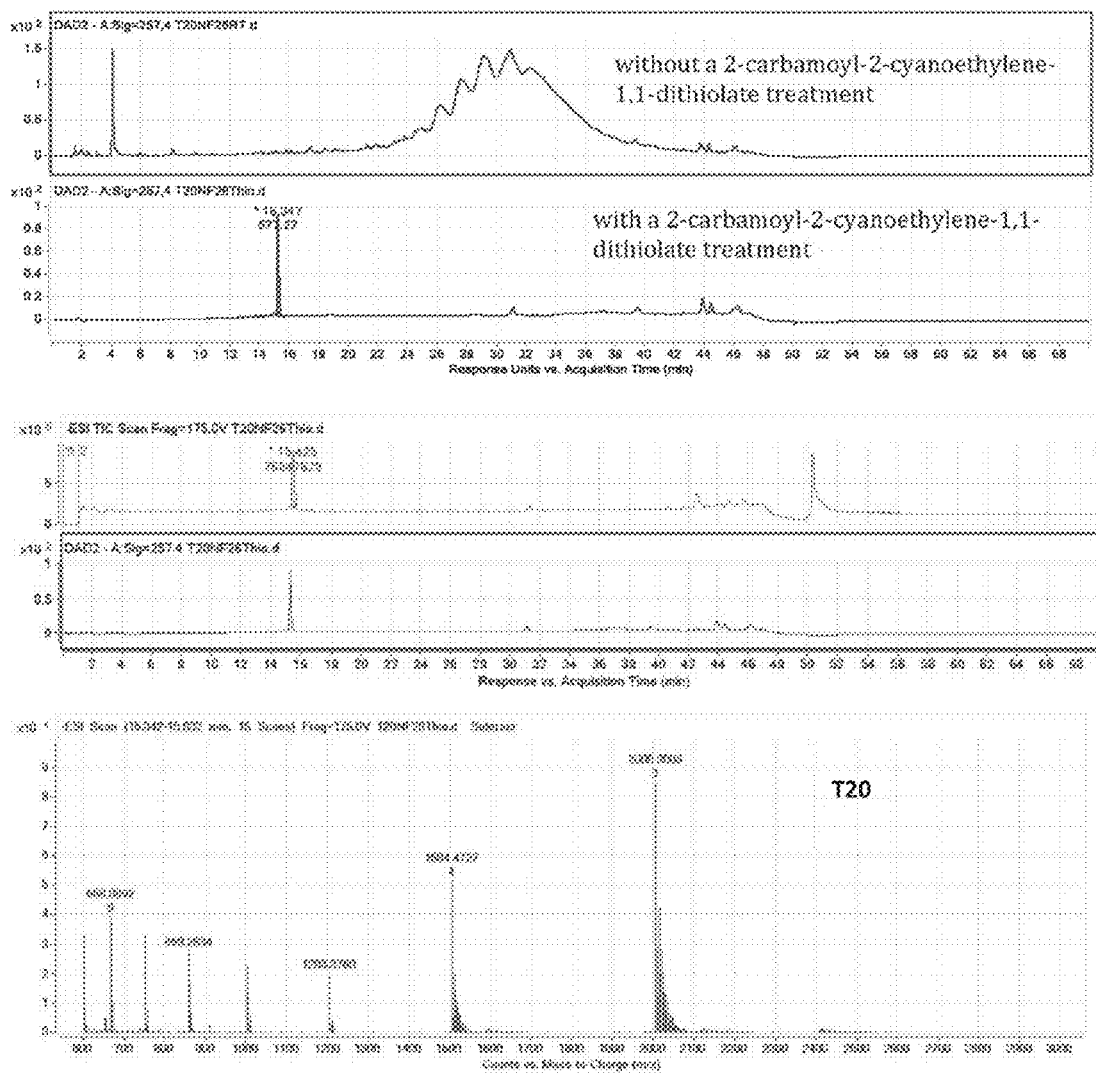
FIG. 6 shows TIC and HPLC chromatograms and Mass analysis of the synthesis of $dT_{20}$ using 4-cyanobenzyl alcohol as phosphorus protecting group with a 2-carbamoyl-2-cyanoethylene-1,1-dithiolate treatment.

TIC, DAD chromatograms and mass analysis of dT$_{20}$ using 4-cyanobenzyl alcohol as phosphorus protecting group with a 2-carbamoyl-2-cyanoethylene-1,1-dithiolate treatment are shown in FIG. 6.

dT$_{20}$ using 5'-O-Dimethoxytrityl-2'-deoxyribothymidine 3'-O-3-cyanobenzylphosphoramidite (28)

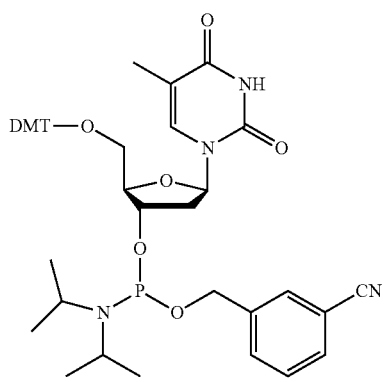
(28)

Figure 7:
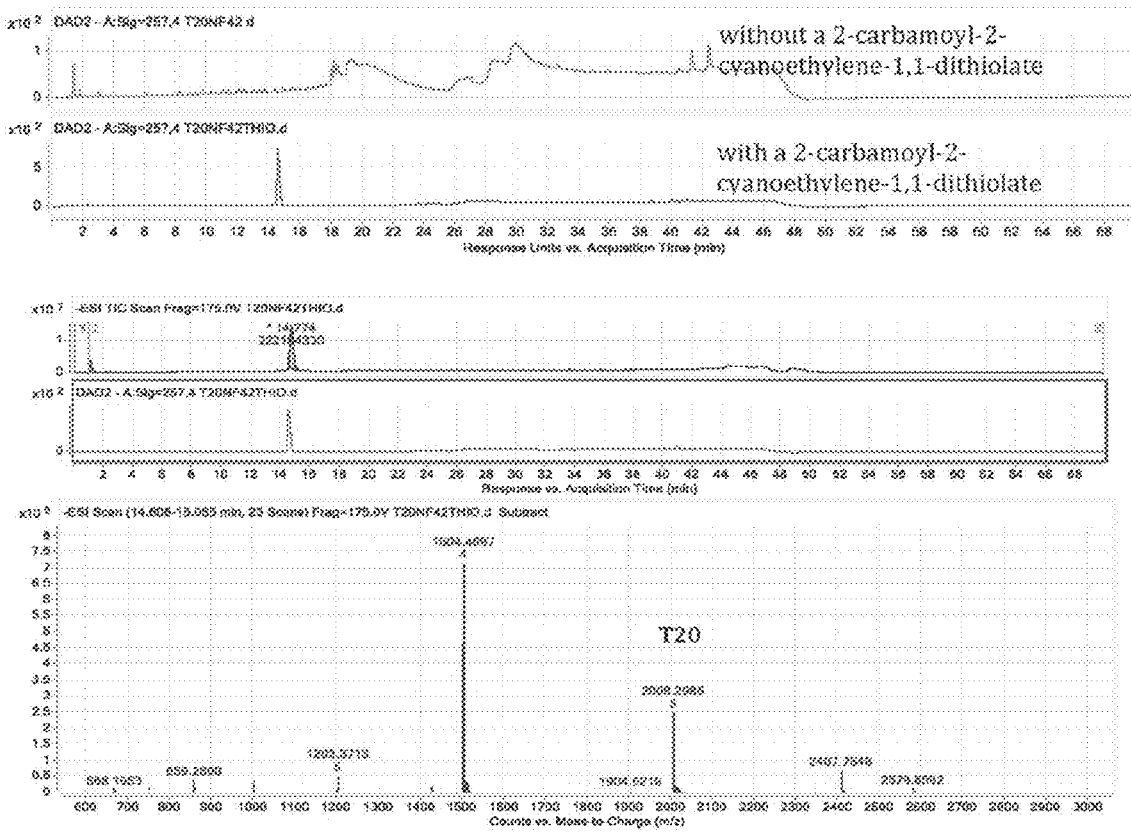
FIG. 7 shows TIC and HPLC chromatograms and Mass analysis of the synthesis of $dT_{20}$ using 3-cyanobenzyl alcohol as phosphorus protecting group with a 2-carbamoyl-2-cyanoethylene-1,1-dithiolate treatment.

TIC, DAD chromatograms and mass analysis of dT$_{20}$ using 3-cyanobenzyl alcohol as phosphorus protecting group with a 2-carbamoyl-2-cyanoethylene-1,1-dithiolate treatment are shown in FIG. 7.

dT$_{20}$ by Using 5'-O-Dimethoxytrityl-2'-deoxyribothymidine 3'-O-2-ethynylbenzylphosphoramidite (29)

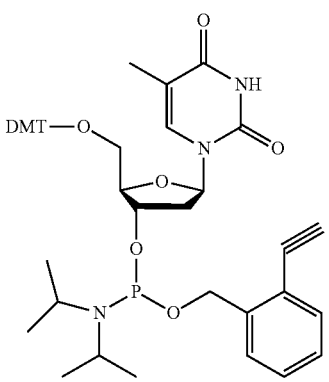
(29)

Figure 8:
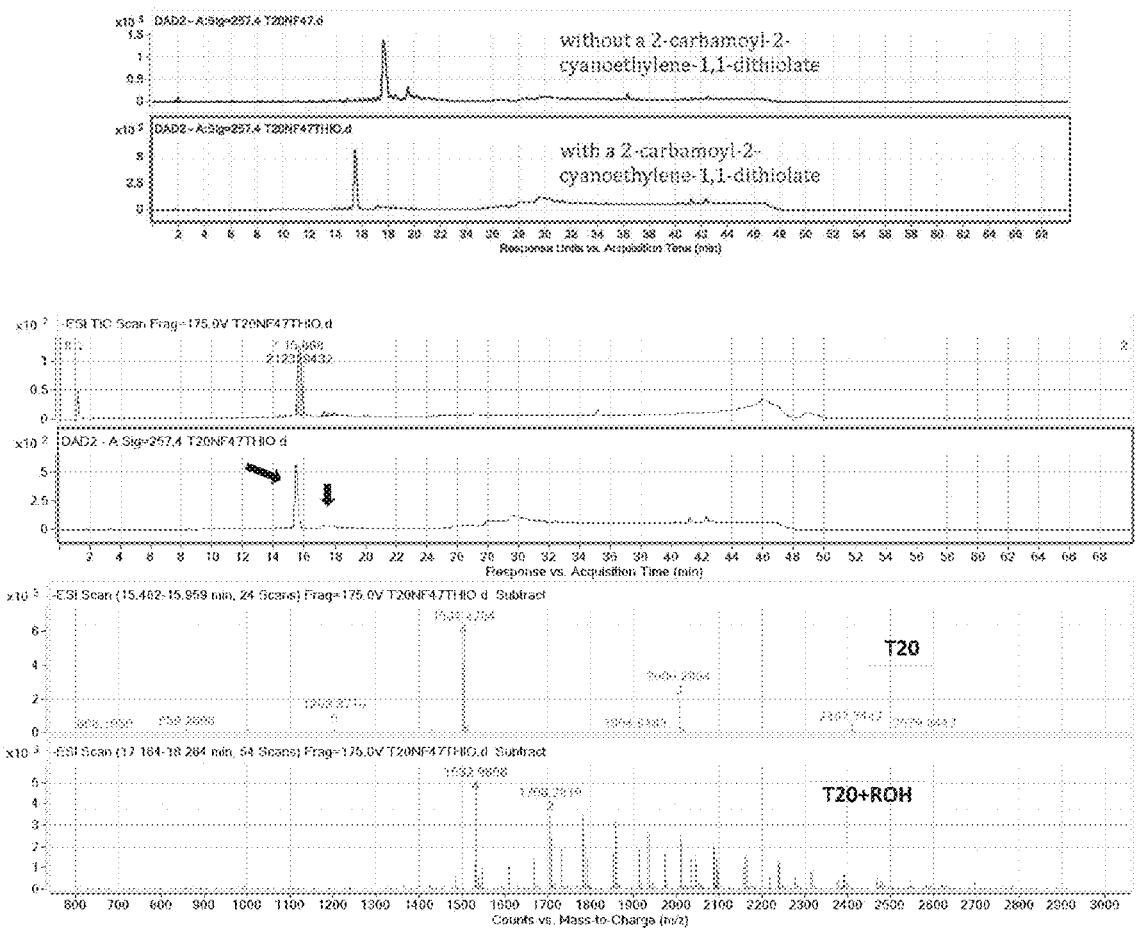
FIG. 8 shows TIC and HPLC chromatograms and Mass analysis of the synthesis of $dT_{20}$ using 2-ethynylbenzyl alcohol as phosphorus protecting group with a 2-carbamoyl-2-cyanoethylene-1,1-dithiolate treatment.

TIC, DAD chromatograms and mass analysis of dT$_{20}$ using 2-ethynylbenzyl alcohol as phosphorus protecting group with a 2-carbamoyl-2-cyanoethylene-1,1-dithiolate treatment are shown in FIG. 8.

dT$_{20}$ Using 5'-O-Dimethoxytrityl-2'-deoxyribothymidine 3'-O-Acetyl-L-threoninemethylesterphosphoramidite (30)

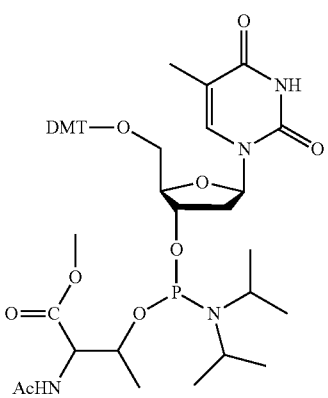
(30)

Figure 9:
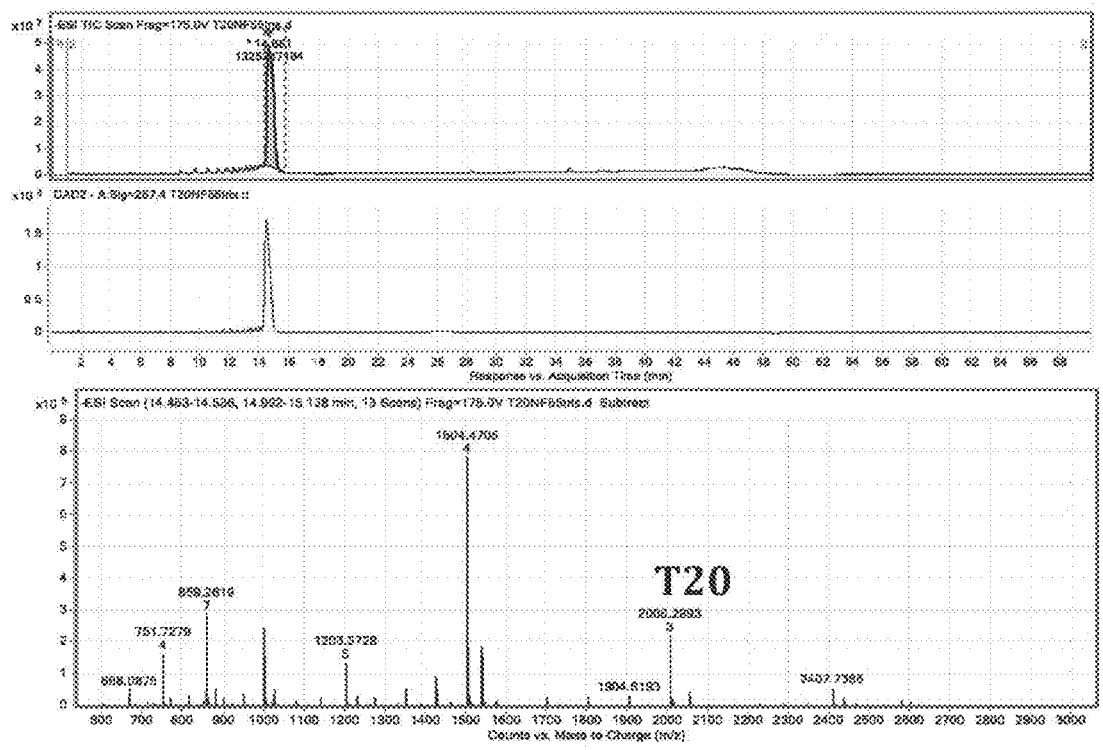
FIG. 9 shows TIC and HPLC chromatograms and Mass analysis of the synthesis of $dT_{20}$ using Acetyl-L-threoninemethylester as phosphorus protecting group.
Figure 9:
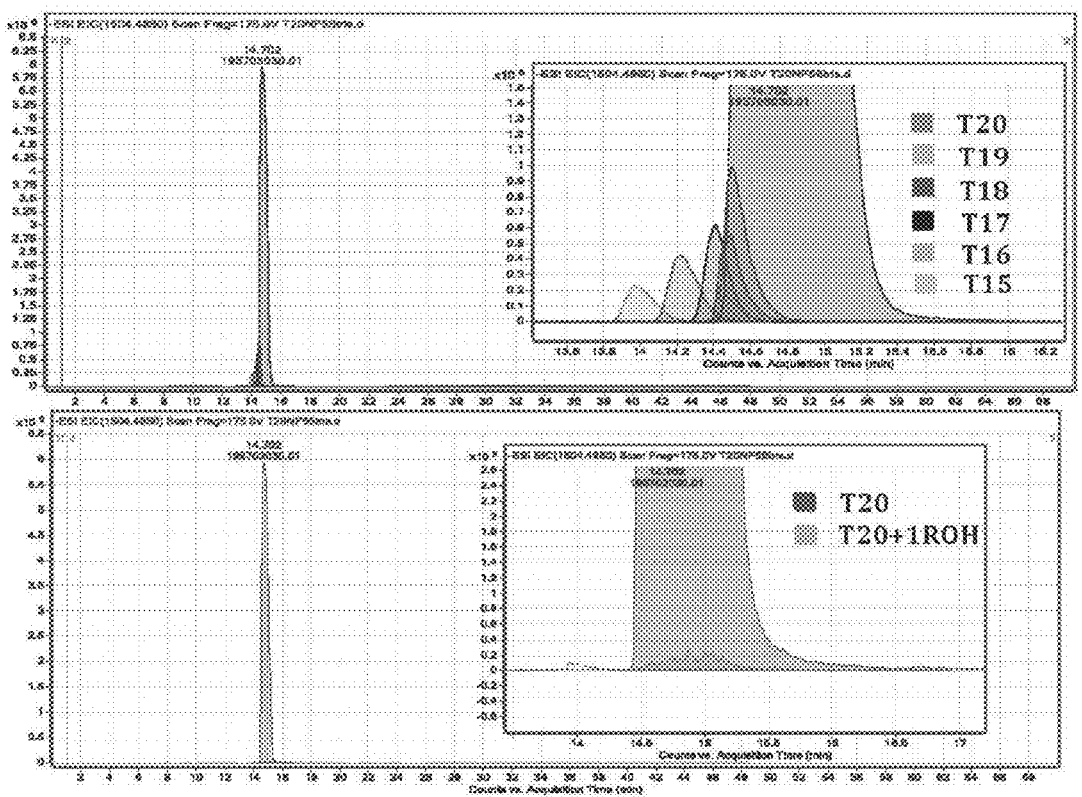

TIC, DAD chromatograms and Mass analysis of dT$_{20}$ using acetyl-L-threoninemethylester as phosphorus protecting group are shown in FIG. 9.

dT$_{20}$ Using 5'-O-Dimethoxytrityl-2'-deoxyribothymidine 3'-O—S-ethylbenzothioate-pyrrolidinylphosphoramidite (31)

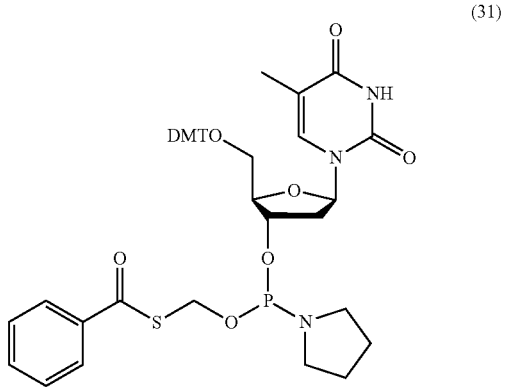

(31)

Figure 10:
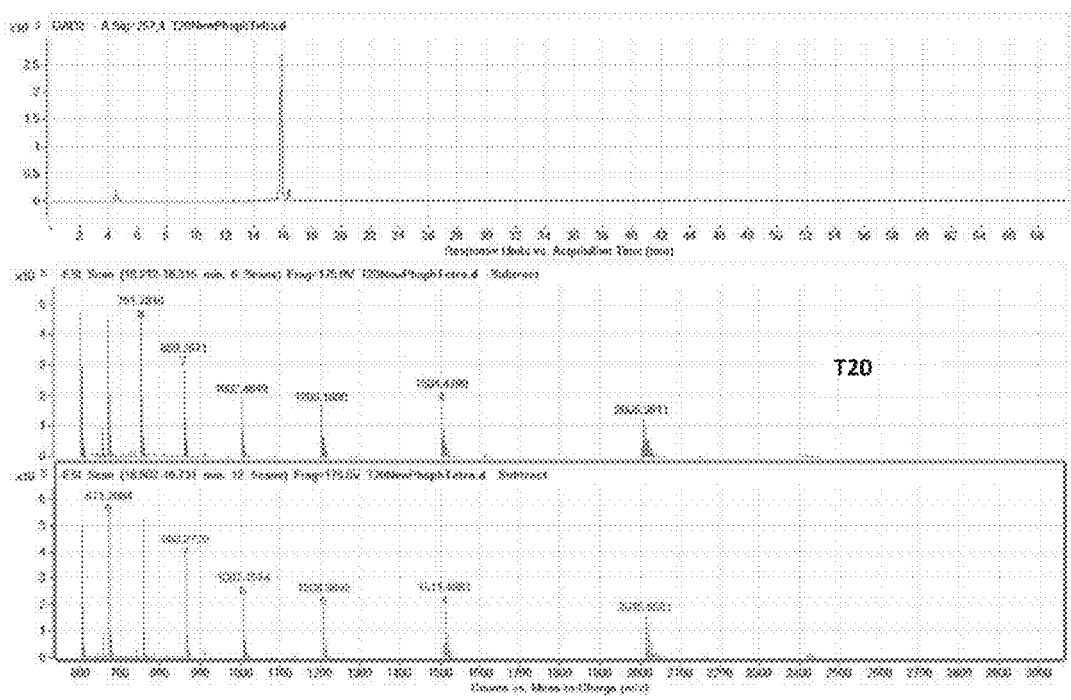
FIG. 10 shows TIC and HPLC chromatograms and Mass analysis of the synthesis of $dT_{20}$ using S-ethylbenzothioate as phosphorus protecting group.

DAD chromatogram and Mass analysis of dT$_{20}$ using S-ethylbenzothioate as phosphorus protecting group are shown in FIG. 10.

dT$_{60}$ Using 5'-O-Dimethoxytrityl-2'-deoxyribothymidine 3'-O-4-cyanobenzylphosphoramidite (27)

27

Figure 11:
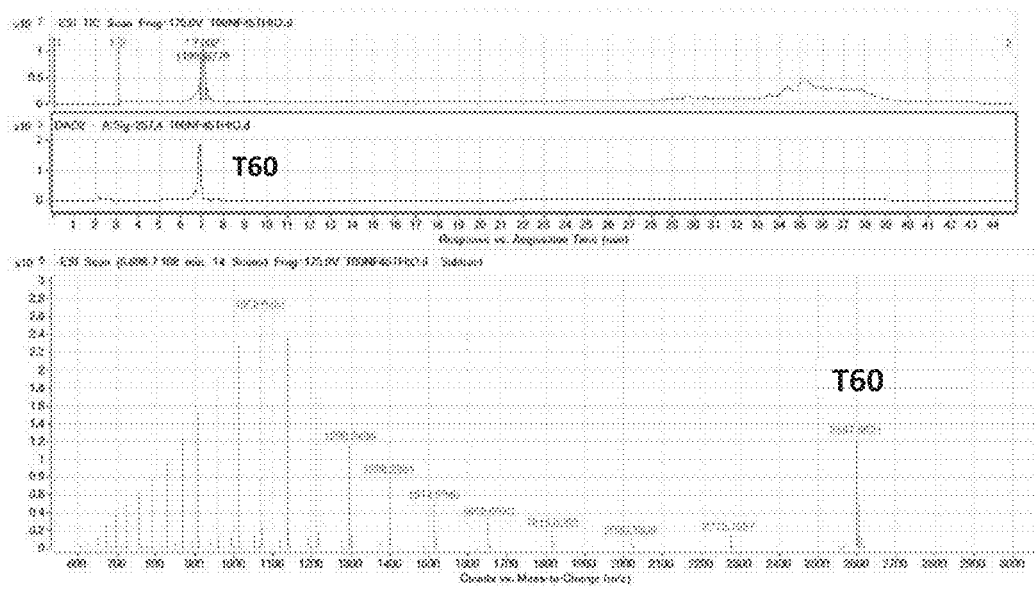
FIG. 11 shows TIC and HPLC chromatograms and Mass analysis of the synthesis of $dT_{20}$ using 4-cyanobenzyl alcohol as phosphorus protecting group with a 2-carbamoyl-2-cyanoethylene-1,1-dithiolate treatment.
Figure 11:
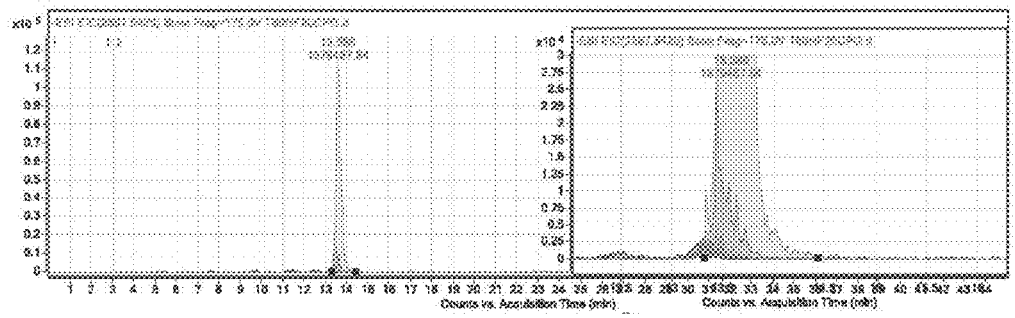

TIC, DAD chromatograms and mass analysis of dT$_{20}$ using 4-cyanobenzyl alcohol as phosphorus protecting group with a 2-carbamoyl-2-cyanoethylene-1,1-dithiolate treatment are shown in FIG. 11.

dT$_{60}$ Using 5'-O-Dimethoxytrityl-2'-deoxyribothymidine 3'-O-Acetyl-L-threoninemethylesterphosphoramidite (30)

Figure 12:
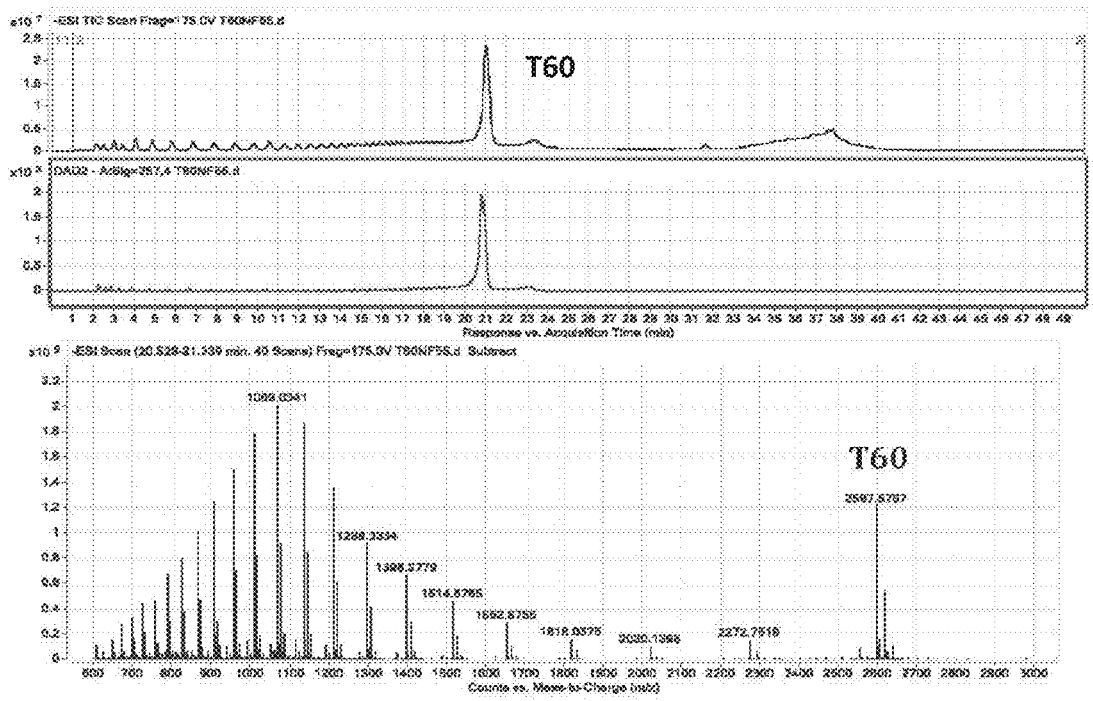
FIG. 12 shows TIC and HPLC chromatograms and Mass analysis of the synthesis of $dT_{60}$ using Acetyl-L-threoninemethylester as phosphorus protecting group.
Figure 12:
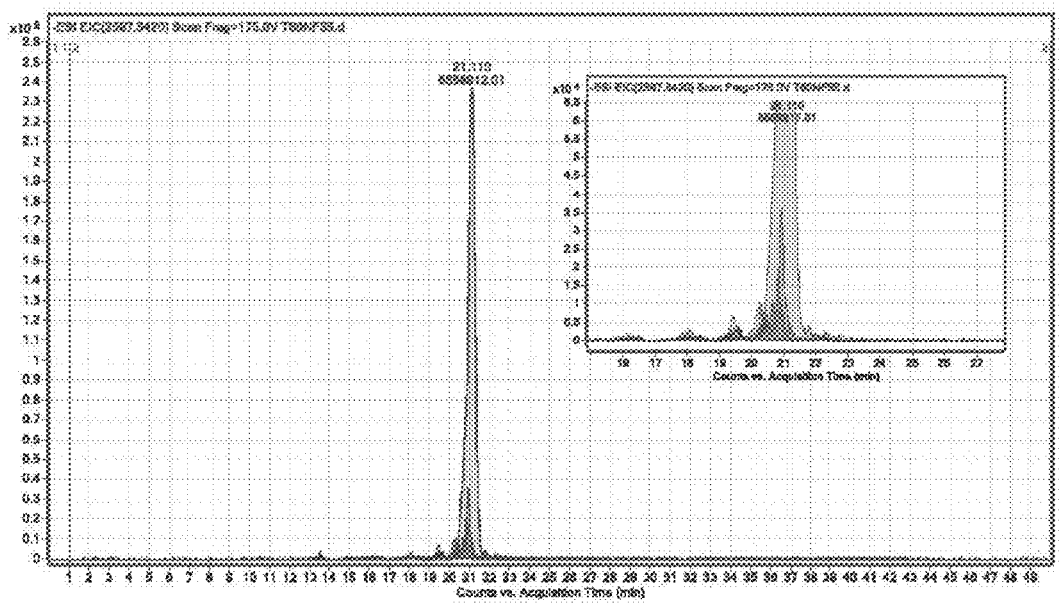

TIC, DAD chromatograms and Mass analysis of dT$_{60}$ using Acetyl-L-threoninemethylester as phosphorus protecting group are shown in FIG. 12.

dT60 by Using 5'-O-Dimethoxytrityl-2'-deoxyribothymidine 3'-O—S-ethylbenzothioate-pyrrolidinylphosphoramidite (31)

Figure 13:
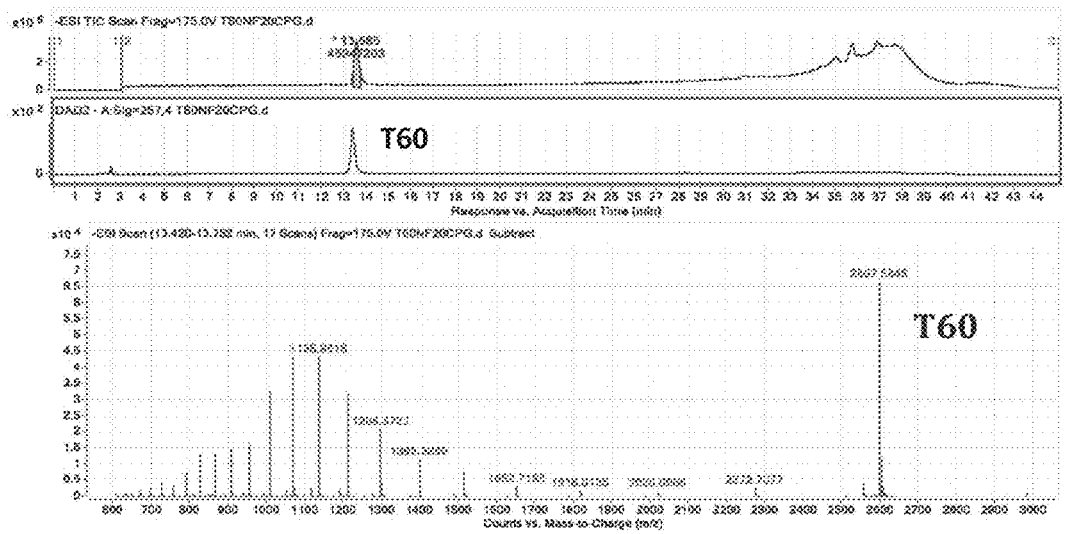
FIG. 13 shows TIC and HPLC chromatograms and Mass analysis of the synthesis of $dT_{60}$ using S-ethylbenzothioate as phosphorus protecting group.
Figure 13:
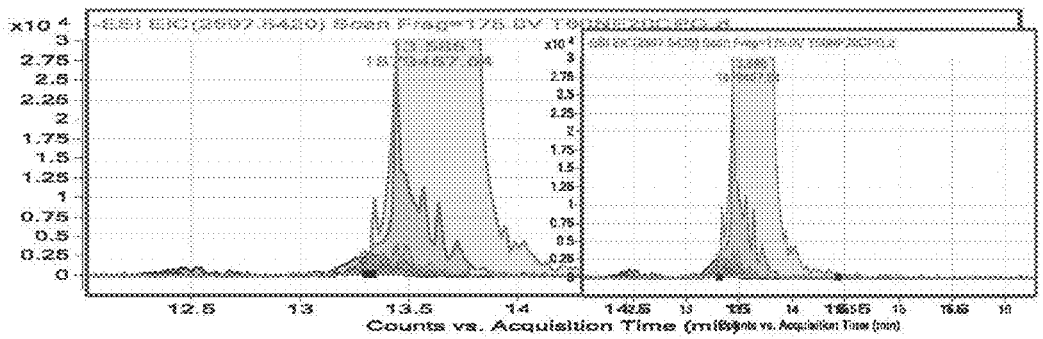

TIC, DAD chromatograms and Mass analysis of dT$_{60}$ using S-ethylbenzothioate as phosphorus protecting group are shown in FIG. 13.

Figure 14:
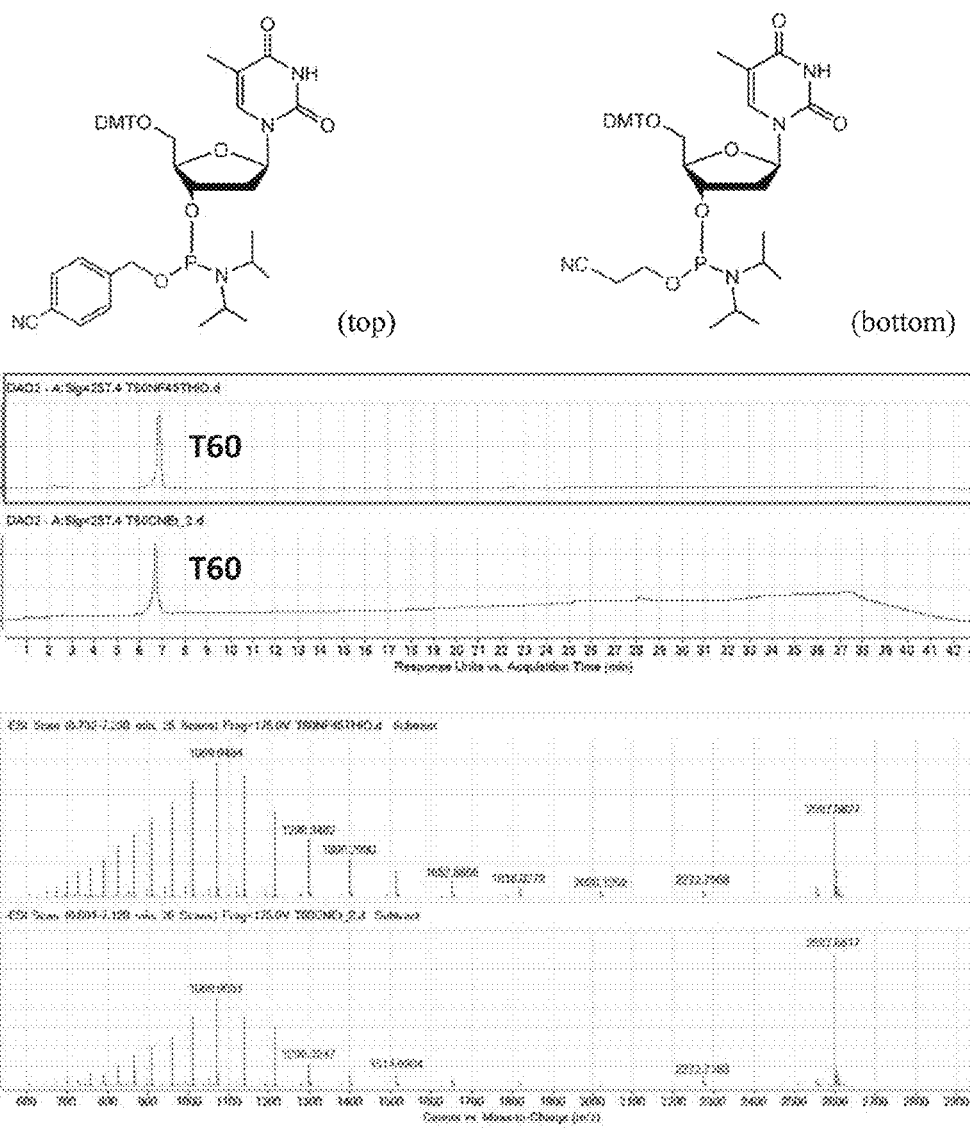
FIG. 14 shows a comparison of TIC and HPLC chromatograms and Mass analysis of a $T_{60}$ synthesized using S-ethylbenzothioate as phosphorus protecting group and a $T_{60}$ synthesized with a standard 2-cyanoethyl phosphoramidite.
Figure 15:
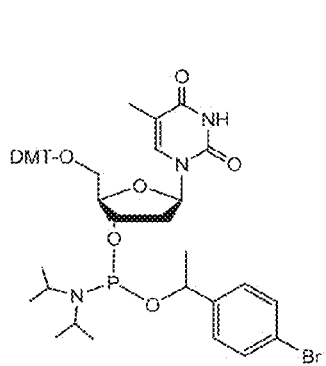
FIG. 15 depicts the structures of phosphoramidite compounds of interest (22-31) used in the synthesis of the oligonucleotides selected and shown in FIG. 1 to FIG. 14.
Figure 15:
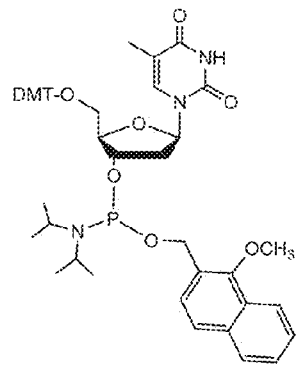
Figure 15:
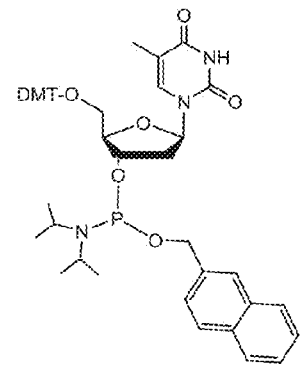
Figure 15:
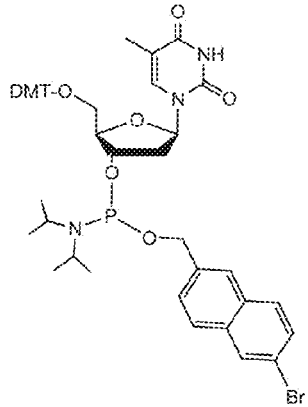
Figure 15:
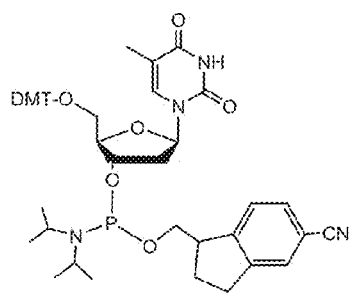
Figure 15:
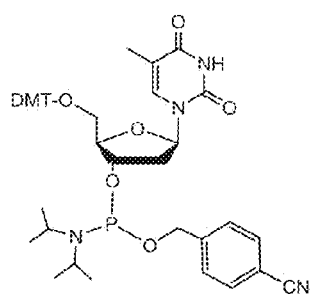
Figure 15:
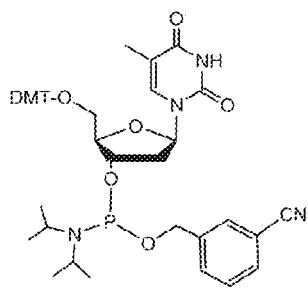
Figure 15:
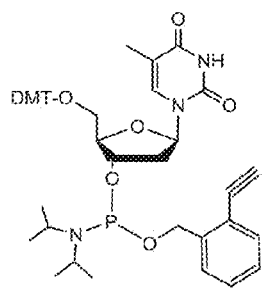
Figure 15:
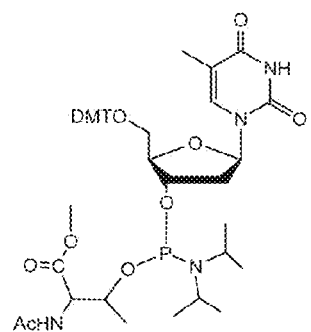
Figure 15:
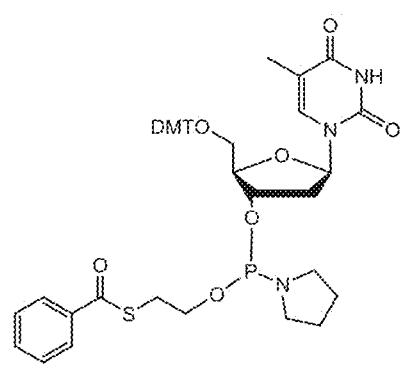
Figure 16:
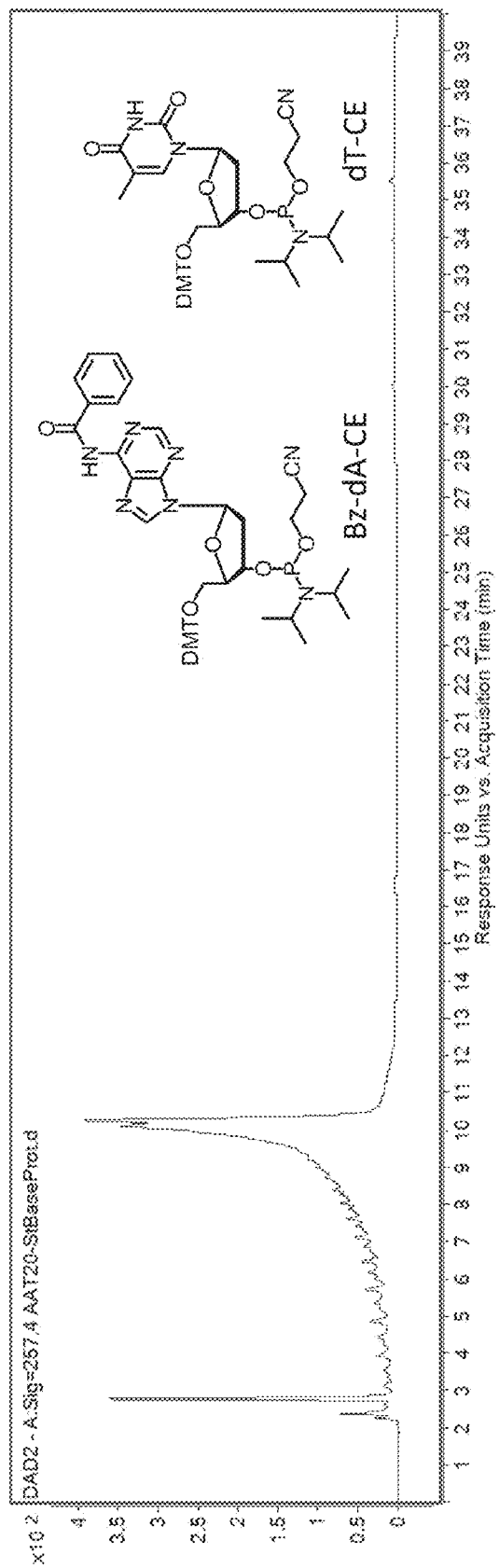
FIG. 16 shows the HPLC chromatogram of a $d(AAT)_{20}$ 60 mers oligonucleotide synthesized with standard benzoyl protecting group on the amino N-6 of adenosine.
Figure 17:
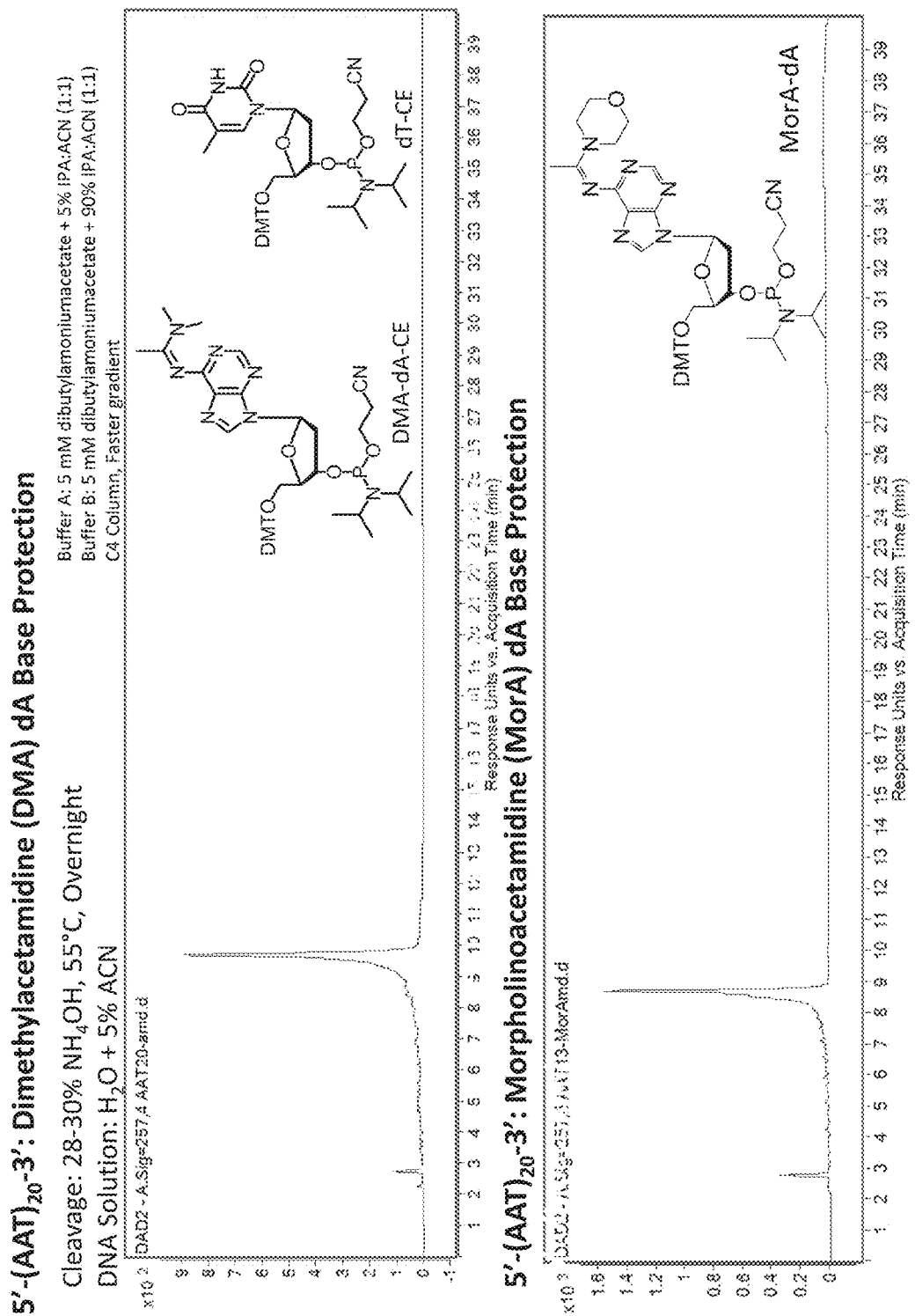
FIG. 17 shows two HPLC chromatograms of a $d(AAT)_{20}$ 60 mers oligonucleotide synthesized with respectively $N^6$-(N,N-dimethylamidino) protecting group on the amino N-6 of adenosine (top) and $N^6$-(1-(morpholino)ethylidene)-dA (bottom).
Figure 18:
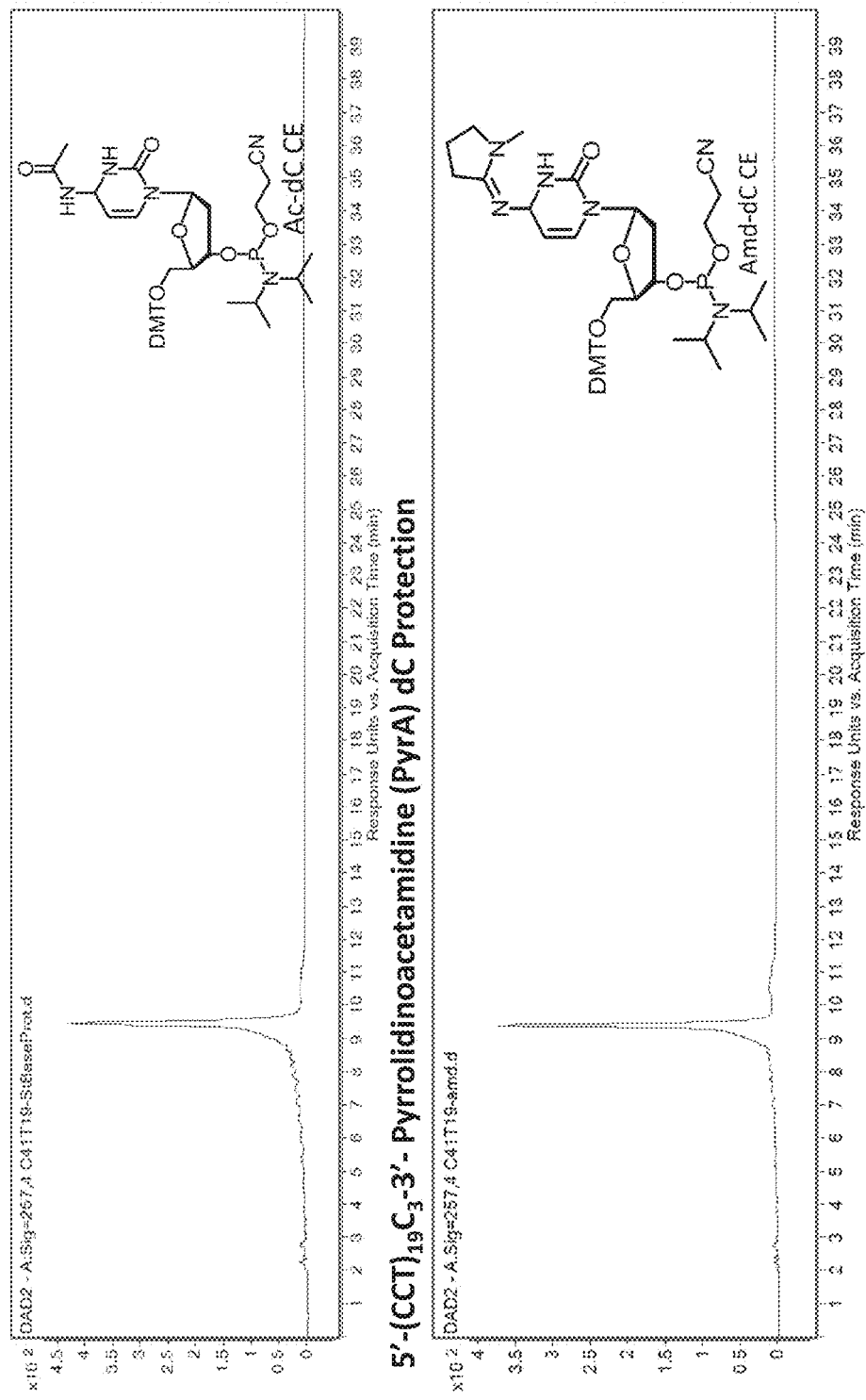
FIG. 18 shows two HPLC chromatograms of a $(CCT)_{19}C_3$ 60 mers oligonucleotide synthesized with respectively $N^4$acetyl dC standard protecting group (top) and $N^4$-(N-methyl-2-pyrrolidinyldene)-dC (bottom).
Figure 19:
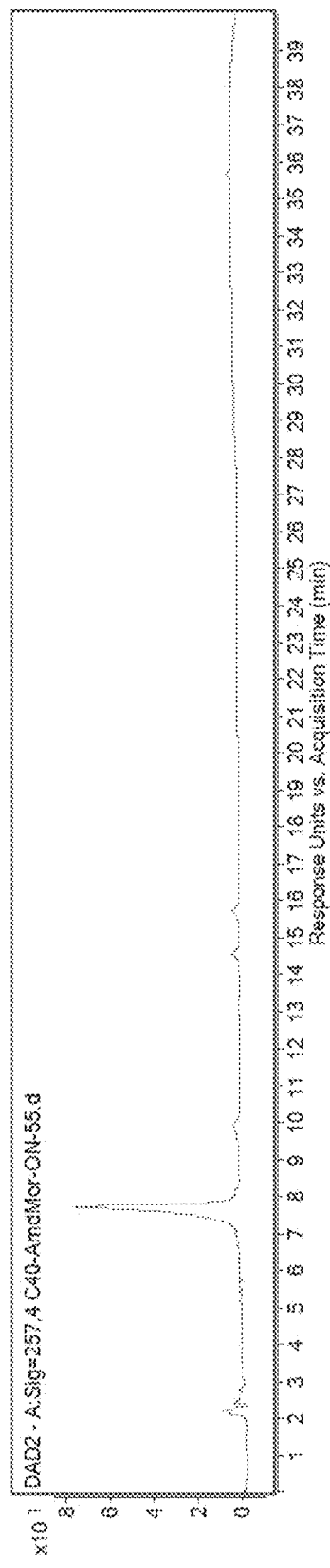
FIG. 19 shows a HPLC chromatogram of a $dC_{40}$ synthesized with $N^4$-(1-(morpholino)ethylidene)-dC.
Figure 19:
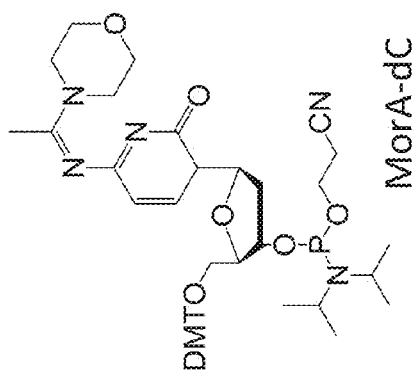
Figure 20:
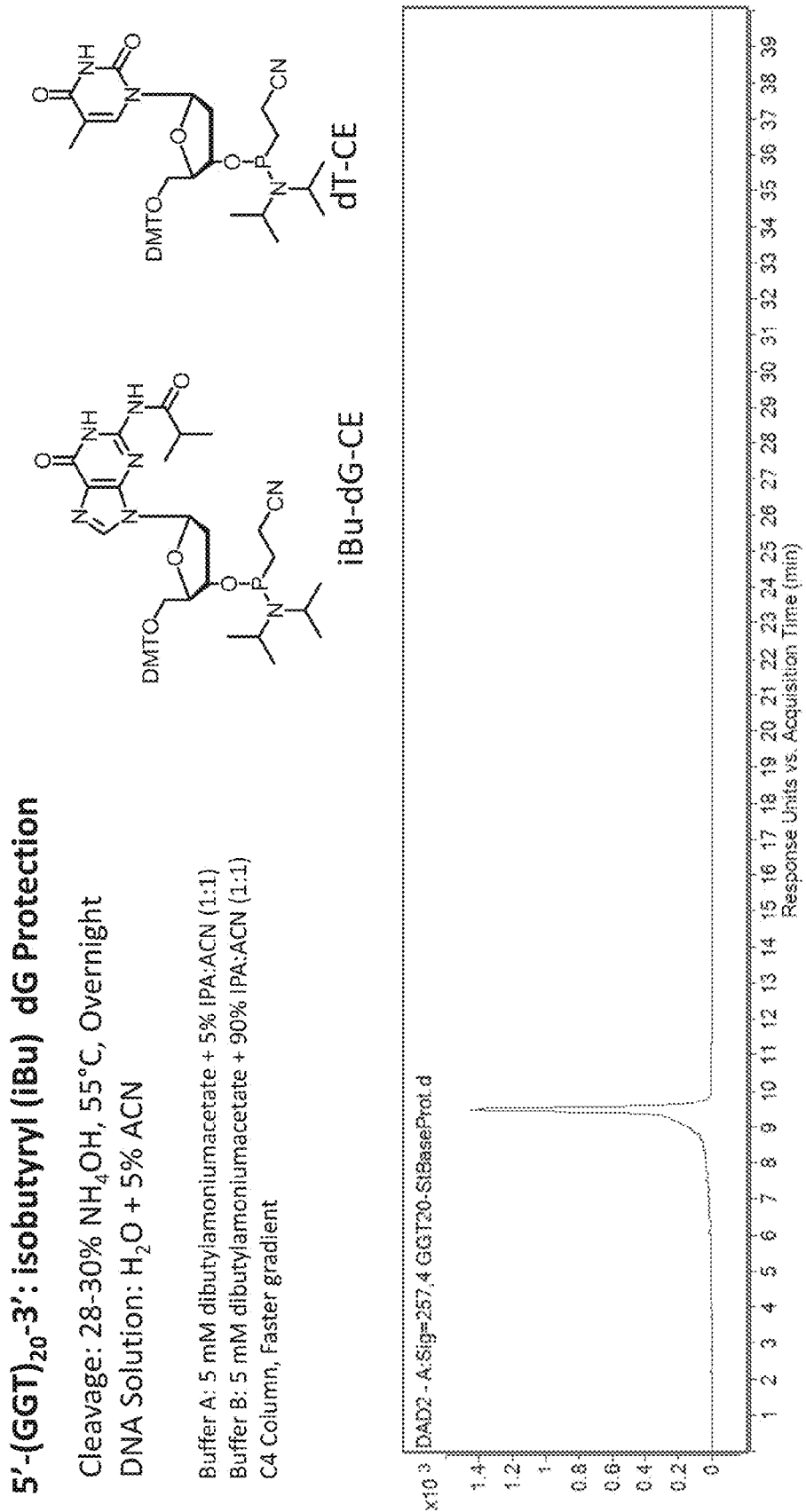
FIG. 20 shows a HPLC chromatogram of a $d(GGT)_{20}$ a 60mers oligonucleotide synthesized with standard $N^2$-(isobutyryl)-dG.
Figure 21:
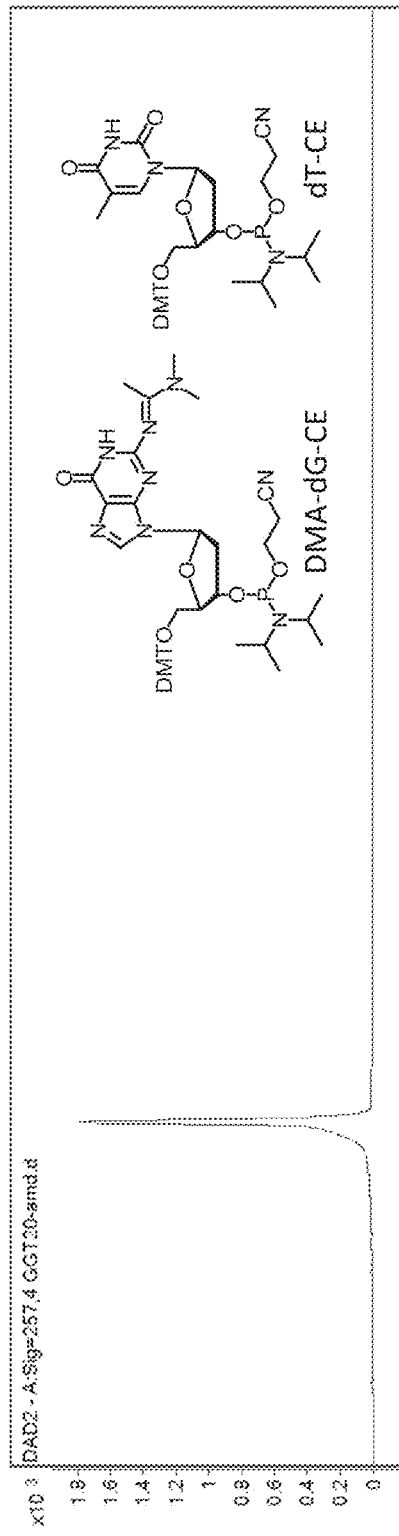
FIG. 21 shows two HPLC chromatograms of a $d(GGT)_{20}$ 60 mers oligonucleotide synthesized with respectively $N^2$—(N,N-dimethylamidino) dG (top) and $N^2$-(1-(morpholino) ethylidene)-dG (bottom).
Figure 21:
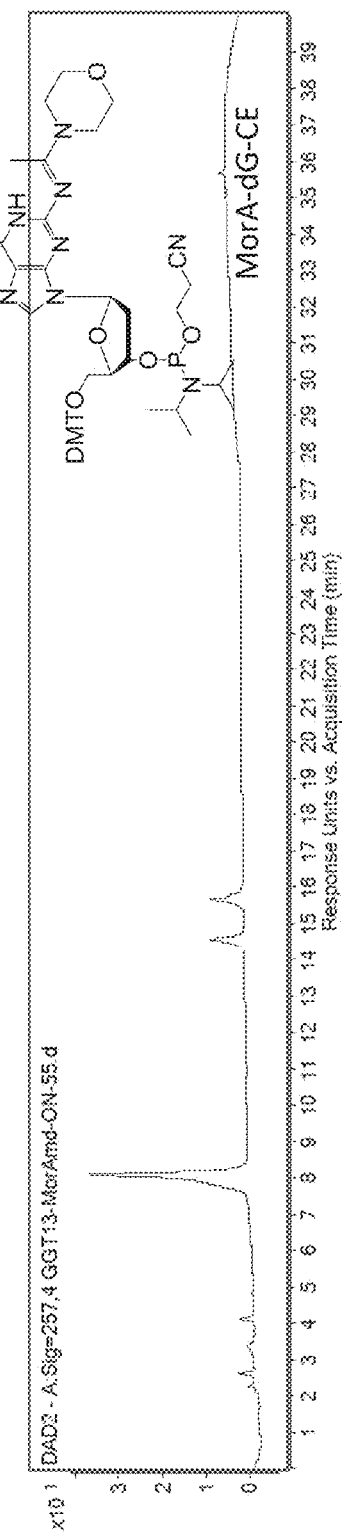
Figure 22:
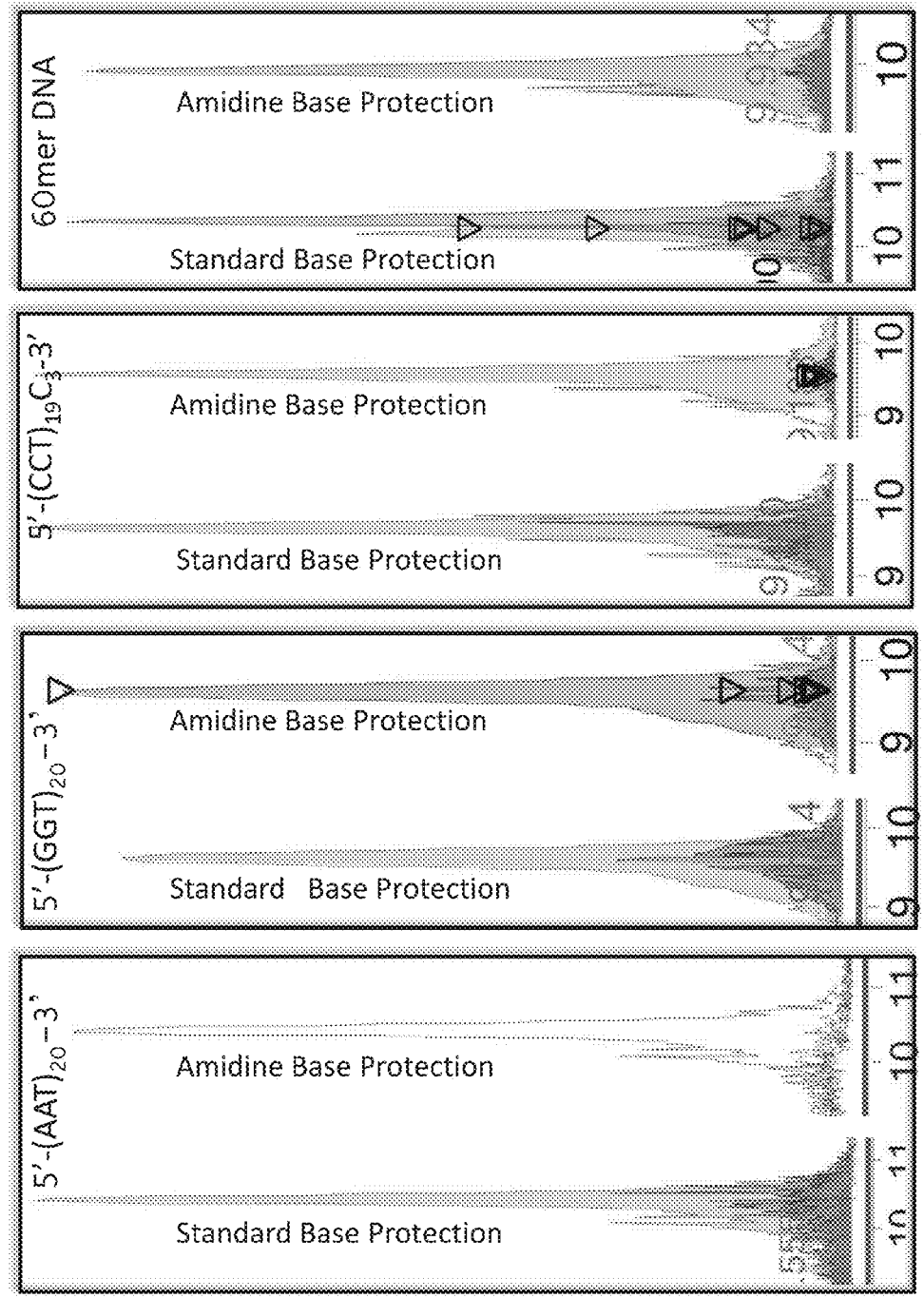
FIG. 22 shows comparative 4 TIC chromatograms of 60mers oligonucleotides synthesized with standard protecting groups and amidine protecting groups. The decrease of base adducts is noticeable when the amidine protecting groups are used.
Figure 23:
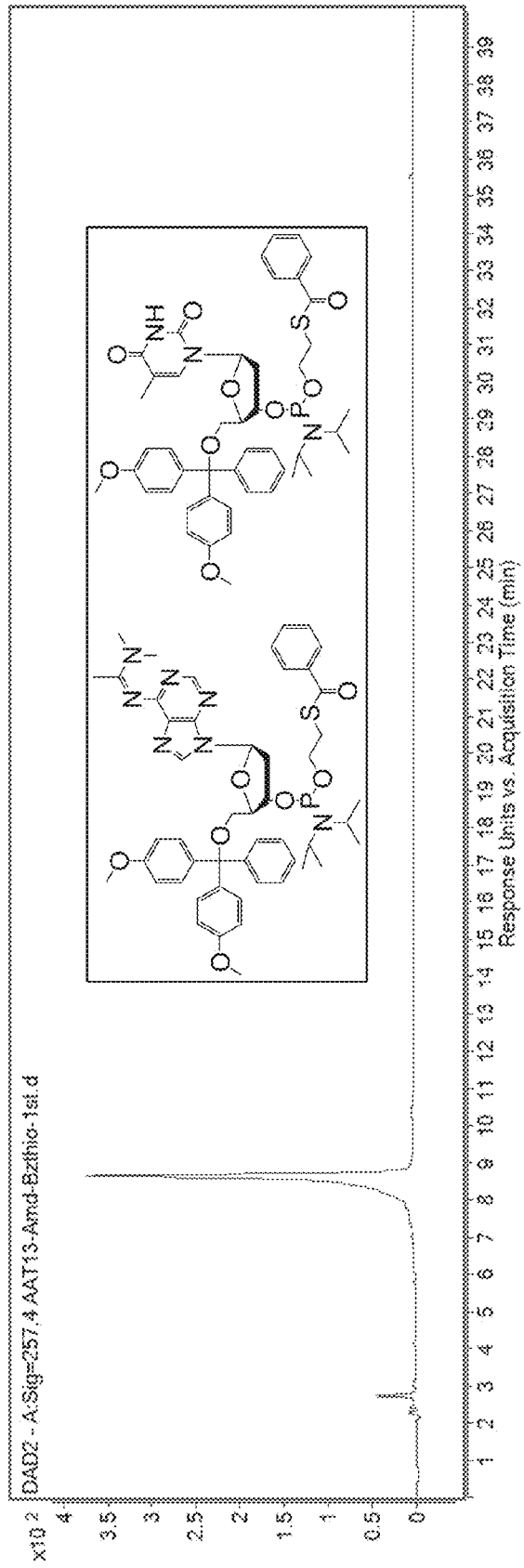
FIG. 23 shows a HPLC chromatogram of a $d(AAT)_{13}$ 39 mers oligonucleotide synthesized with $N^6$—(N,N-dimethylamidino)-dA-3'O—S-(ethyl)benzothioate phosphoramidite.
Figure 24:
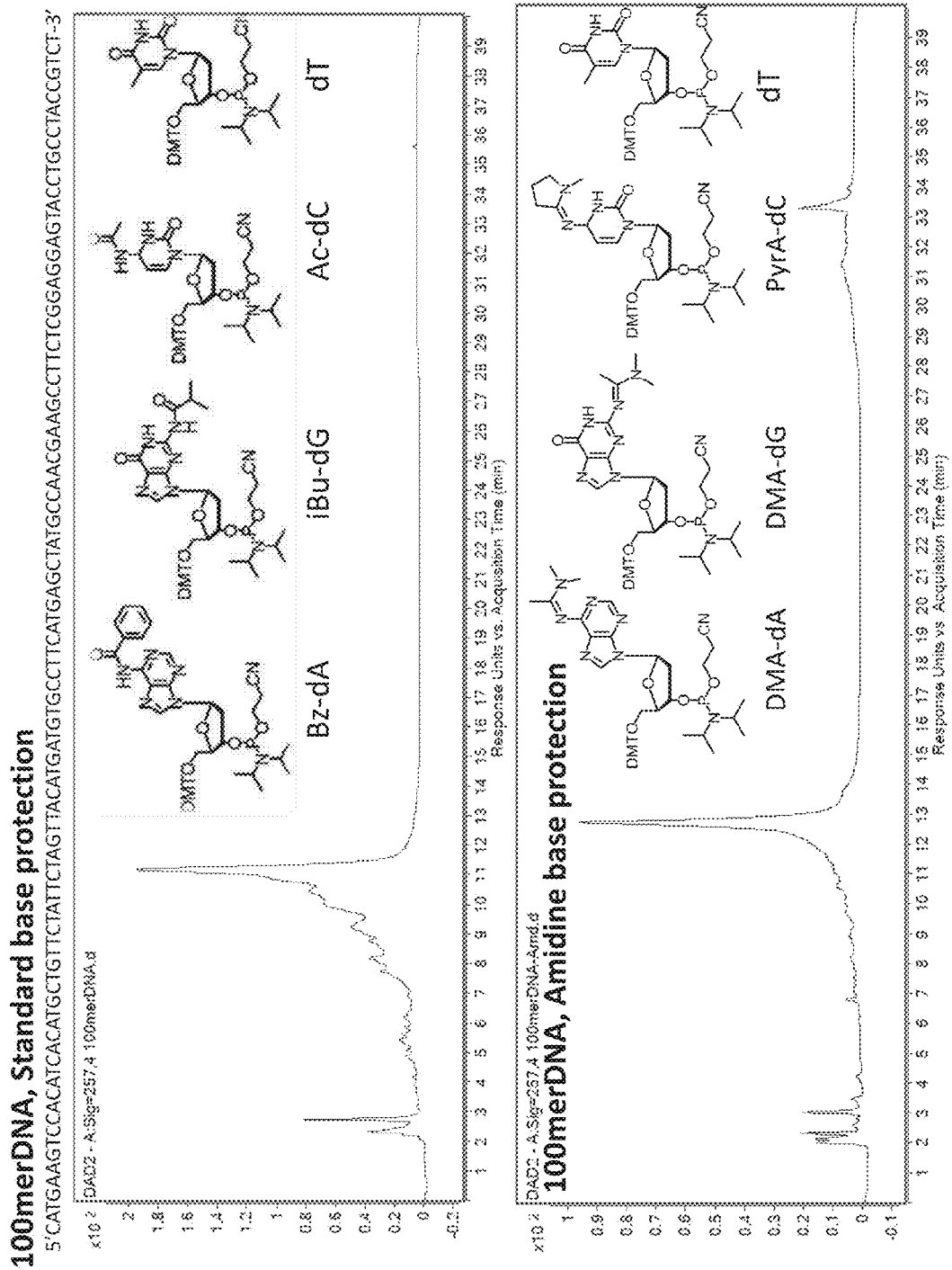
FIG. 24 shows two comparative HPLC chromatograms of two 100mers oligonucleotides synthesized respectively with standard nucleobase protecting groups (top) and amidine protecting groups (bottom).

Comparison of a T$_{60}$ synthesized using S-ethylbenzothioate as phosphorus protecting group with a T$_{60}$ synthesized with a standard 2-cyanoethyl phosphoramidite is shown in FIG. 14.

The following examples illustrate the general synthetic strategy of additional compounds (1-15) described herein.

Materials and Methods:

5'-Dimethoxytrityl-N$^6$-dimethylaminoacetamidine-2'-deoxyadenosine,3'-[(2-cyanoethyl)-(N,N-diisopropyl)]-phosphoramidite DMA-dA-CE, adenosine hydrate, guanosine hydrate, cytidine hydrate, dimethoxytrityl chloride were purchased from Chem Genes, 5'-Dimethoxytrityl-N$^4$-acetyl-T-deoxycytidine,3'-[(2-cyanoethyl)-(N,N-diisopropyl)]-phosphoramidite (Ac-dC-CE), 5'-Dimethoxytrityl-N$^2$-isobutyryl-2'-deoxyguanosine,3'-[(2-cyanoethyl)-(N,N-diisopropyl)]-phosphoramidite iBu-dG-CE, dT-CE, dT-CPG column (1 μmol), dC-CPG column (1 μmol), 0.45M ethylthio-tetrazole in acetonitrile, CAP Mix A (THF/Pyridine/Ac$_2$O) and CAP Mix B (16% MeIm in THF), 0.02M I$_2$ in THF/Pyridine/H2O, 3% Trichloroacetic acid in dichloromethane, dry acetonitrile were purchased from Glen Research. 4-acetylmorpholine, N,N-dimethyl acetamide diethyl acetal, N-Methylpyrrolidone, N,N-Diisopropylethylamine, dry pyridine, Dimethyl Sulphate, NaOMe were purchased from Sigma-Aldrich.

DNA synthesis and LCMS studies: DNAs were synthesized in 394 RNA/DNA synthesizer (Applied Bio system. 0.2 μmole method). P(III) chemistry of phosphoramidite method was used to synthesize DNA in standard four step cycle viz. deprotection, activation and coupling, oxidation and capping. 3% Trichloroacetic acid in dichloromethane was used for the deprotection, 0.45M ethylthio-tetrazole in acetonitrile was used as the activating agent. 0.02M I$_2$ in THF/Pyridine was used for oxidation from amidite to phosphate. THF/Pyridine/Ac$_2$O and 16% N-Methylimidazole in THF were used to cap the sequences that fail to couple. Controlled pore glass (CPG) was used as the immobilized phase. Shorter DNA was synthesized on the CPG of 500 Å pore size in 1 μmole scale while longer sequences (>20 bp) were synthesized on CPG of 1000 Å pore size in 0.2 μmole scale. The DNAs were cleaved from the solid support by treating CPG with 28-30% NH$_4$OH at 55° C. for overnight. However the cleavage and deprotection efficiency of NH$_4$OH was studied for the acetamidine and morpholinoacetamidine protecting groups at variable temperature from ambient temperature to 55° C. and 2 h to overnight.

The cleaved DNA was extracted into H$_2$O containing 5% acetonitrile and filtered. The filtered DNA was directly used for LCMS studies. LCMS spectra were recorded in Agilent 6500 Q-TOF LC/MS system. LC/MS were recorded by using dibutylammonium acetate/isopropyl alcohol (IPA)/acetonitrile (ACN) as the eluent buffer system. The composition of buffer was: Buffer A: 5 mM dibutylammoniumacetate+5% IPA:ACN (1:1), Buffer B: 5 mM dibutylammonium acetate+90% IPA:ACN (1:1). Dibutylammonium acetate was selected for the mobile phase to reduce mass spectral signal of higher charge states. It helped to extract EIC spectra of the DNA of desired mass. Mass spectra of the DNA was analysed by Agilent MassHunter Workstation Qualitative Analysis B.06.00. EIC spectra of oligos with desired mass was extracted from the TIC chromatogram by the input of exact and calculated mass value of the DNA or adducts.

Synthesis of Precursor Reagents for the Nucleobase Protection

N,N-Dimethylacetamide Diethyl acetal

N,N-Dimethylacetamide Diethyl acetal was synthesized according to the procedure of McBride, L. J; Kierzek, R.; Beaucage, S. L.; Caruthers, M. H. J. Am. Chem. Soc., 1986, 108, 2040-2048.

2,2-Dimethoxy-1-methylpyrrolidine (Lu, J.; Khdour, O. M.; Armstrong, J. S.; Hecht, S. M. Bioorg. Med. Chem., 2010, 18, 7628-7638)

A mixture N-methyl-2-pyrrolidinone (26 mL, 273 mmol) and of dimethyl sulfate (26 mL, 278 mmol) was stirred and heated at 90° C. for 90 min, then allowed to cool to room temperature. A solution containing 65 mL of 25% methanolic sodium methoxide and 135 mL of methanol was added at ~10° C. under argon over a period of 1 h. The precipitated white solid was filtered and the solvent was concentrated under reduced pressure. The yellow oily residue was dissolved in 250 mL of diethylether and stirred for another 1 h, then the precipitated solid was filtered again. The solid was washed with diethylether. After the ether was concentrated, the residue was distilled in vacuo to give the compound as a pale yellow liquid: yield 14.8 g (37%). $^1$H NMR in CHCl$_3$ is according to the literature.

Synthesis of 4-(1,1-dimethoxyethyl)morpholine
(Feng R., -L; Gong, P.; Fang, L.; Hong, W. Chem. Res. Chinese U, 2005, 21, 177-192)

A mixture 4-acetylmorpholine (32 mL, 278 mmol) and of dimethyl sulfate (26 mL, 278 mmol) was stirred and heated at 90° C. for 60 min, then allowed to cool to room temperature. A solution containing 65 mL of 25% methanolic sodium methoxide and 135 mL of methanol was added at ~10° C. under argon over a period of 2 h. The precipitated white solid was filtered and the solvent was concentrated under reduced pressure. The yellow oily residue was dissolved in 250 mL of diethylether and stirred for another 1 h, then the precipitated solid was filtered again. The solid was washed with diethylether. After the ether was concentrated, the residue was used for the next step of the reaction. The weight of the crude oil was 22 g.

Synthesis of dA, dC, dG, dT 3'-(2-cynoethyl)-N,N-diisopropylphosphoramidites

Scheme 1 depicts the synthesis of compound (3) under the following conditions: (i) 4-(1,1-dimethoxyethyl)morpholine, RT, Overnight; (ii) 4,4-Dimethoxytritylchloride, pyridine, N,N-Diisopropylethylamine (2 h); (iii) N,N-Diisopropyl-Cyanoethyl phosphoramiditechloride, N,N-Diisopropylethylamine, CH$_2$Cl$_2$ (2 h).

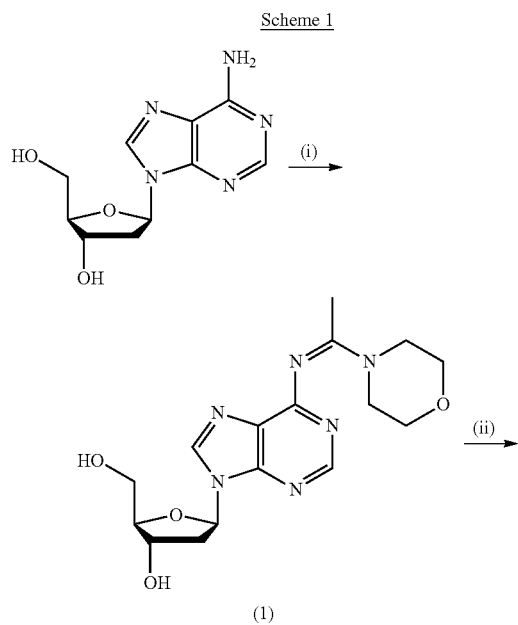

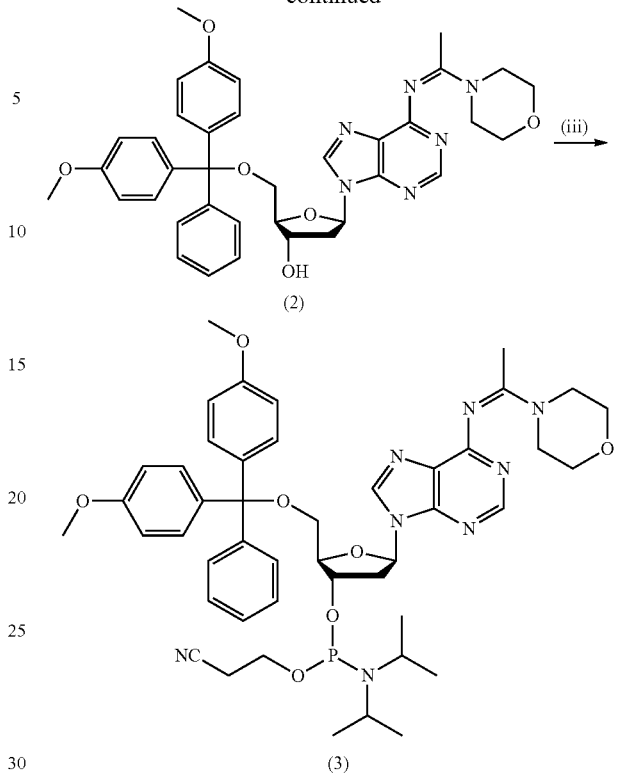

6-N-(1-(morpholino)ethylidene)-2'-deoxyadenosine (1)

2.69 g (10 mmol) of 2'-Deoxyadenosine monohydrate was co-evaporated with pyridine 3 times and was suspended in 20 mL of dry methanol. 10 g of 4-(1,1-dimethoxyethyl) morpholine was added slowly with constant stirring under the argon. The reaction was allowed to continue for overnight. After the reaction methanol was removed by rotary evaporation. The sticky residue was washed several times with diethyl ether to obtain non-sticky white powder. The compound was further purified by silica gel column chromatography with CHCl$_3$ as the eluent. Methanol (0-10%) was used as the gradient. After removing the solvent the pure compound (1) appeared as white foam. Yield: 3.19 g (88%), R$_f$ (CHCl$_3$/MeOH 10/2 v/v): 0.43, $^1$H NMR (CDCl$_3$, 400 MHz): δ8.22 (s, 1H), 7.54 (s, 1H), 5.77 (t, J=6.11 Hz, 1H), 4.03 (d, J=6.4 Hz, 1H), 3.88 (m, 2H), 3.64 (m, 1H), 3.37 (m, 4H. O(CH$_2$)$_2$), 2.83 (m, 4H, N(CH$_2$)$_2$), 2.51-2.29 (m, 2H), 1.73 (s, 3H, C—CH$_3$). $^{13}$C NMR (CDCl$_3$, 400 MHz): δ160.85, 154.22, 152.01, 147.94, 138.21, 122.11, 88.22, 83.19, 71.53, 68.12, 62.41, 46.36, 40.11, 22.38.

5'-O-(Di-p-methoxytrityl)-6-N-(1-(morpholino)ethylidene)-2'-deoxyadenosine (2)

4-N-(1-(Dimethylamino)ethylidene)-2'-deoxyadenosine (1) (3.19 g 0.0088 mole) was dissolved in dry pyridine (25 mL) and the solution made saturated with argon. N,N-diisopropylethylamine (6.42 g, 0.05 mole, 8.65 mL) was added to the solution and stirred for 10 min under the argon. Solution of Di-p-methoxytritylchloride (2.95 g, 0.0088 mole) in 25 mL of dry pyridine was prepared under the argon. The DMT-Cl solution was transferred to the solution of 1 with the continuous flow of argon. The reaction was allowed to continue for 2 h with constant stirring under the argon. Solution was concentrated and further diluted with 100 mL of dichloromethane. The mixture was washed with saturated aqueous solution of NaHCO$_3$ (100 mL) thrice. The organic phase was further washed with saturated aqueous solution of NaCl (100 mL). The organic phase was dried over anhydrous Na$_2$SO$_4$. The compound was further purified by silica gel column chromatography in CH$_2$Cl$_2$ (MeOH was used as the gradient, 0-2%) with 3% triethylamine. After removing the solvent, the compound (2) appeared as the white foam. Yield: 4.54 g (78%); R$_f$ (CH$_2$Cl$_2$/MeOH 10/0.5 v/v): 0.41; $^1$H NMR (CDCl$_3$, 400 MHz): δ8.48 (s, 1H), 7.76 (s, 1H), 7.3-6.6 (m, 13H, aryl), 5.84 (t, J=6.31 Hz, 1H), 4.13 (d, 0.1=7.3 Hz, 1H), 3.93 (m, 2H), 3.76 (s, 6H, (O—CH$_3$)$_2$), 3.54 (m, 1H), 3.33 (m, 4H. O(CH$_2$)$_2$), 2.91 (m, 4H, N(CH$_2$)$_2$), 2.55-2.31 (m, 2H), 1.61 (s, 3H, C—CH$_3$). $^{13}$C NMR (CDCl$_3$, 400 MHz): δ167.15, 157.62, 154.41, 150.37, 147.54, 140.22, 140.14, 133.97, 130.21, 128.33, 124.32, 122.38, 112.76, 91.22, 86.92, 80.27, 74.22, 67.21, 62.12, 59.37, 47.28, 41.19, 23.3.

5'-O-(Di-p-methoxytrityl)-6-N-(1-(morpholino)ethylidene)-2'-deoxyadenosine-2-cyanoethyl-N,N-diisopropylphosphoramidite (3)

5'-O-(Di-p-methoxytrityl)-4-N-(1-morpholinoethylideneamino)-2'-deoxyadenosine (2) (1.66 g, 0.0025 mole) was dissolved in 10 mL of dry CH$_2$Cl$_2$. N,N-diisopropylethylamine (6 mL) was added to the solution with continuous flow of argon and stirring. N,N-Diisopropyl-O-cyanoethyl-chlorophosphoramidite (590 mg, 0.0025 mole) was added to the solution and the reaction was allowed to continue for 2 h under argon. After the reaction was over the solution was poured into 30 mL of saturated aq. NaHCO$_3$ solution and extracted with CH$_2$Cl$_2$ (3×10 mL). The combined organic phases were dried over Na$_2$SO$_4$ and the solvent was evaporated. The resulting oil was purified by column chromatography with CH$_2$Cl$_2$ containing 3% triethylamine to give the final compound (3) as white foam. The compound was further purified by cold hexane precipitation from dichloromethane solution. Yield: 1.51 g (71%). R$_f$ (CH$_2$Cl$_2$/MeOH 10/0.5 v/v): 0.44, $^{31}$P NMR (CDCl$_3$, 400 MHz): δ148.74, 147.91 (Diastereoisomers).

Scheme 21 depicts the synthesis of compound (9) according to the following conditions: (i) N,N-Dimethylacetamide Diethyl acetal, Ethanol, 60° C., 24 h; (ii) 4,4-Dimethoxytritylchloride, pyrideine, N,N-Diisopropylethylamine, RT, 2 h); (iii) N,N-Diisopropyl-Cyanoethyl phosphoramiditechloride, N,N-Diisopropylethylamine, CH$_2$Cl$_2$ (2 h); (iv) 4-(1,1-dimethoxyethyl)morpholine, 60° C., Overnight; (v) 4,4-Dimethoxytritylchloride, pyrideine, N,N-Diisopropylethylamine (3 h); (vi) N,N-Diisopropyl-Cyanoethyl phosphoramiditechloride, N,N-Diisopropylethylamine, CH$_2$Cl$_2$ (2 h).

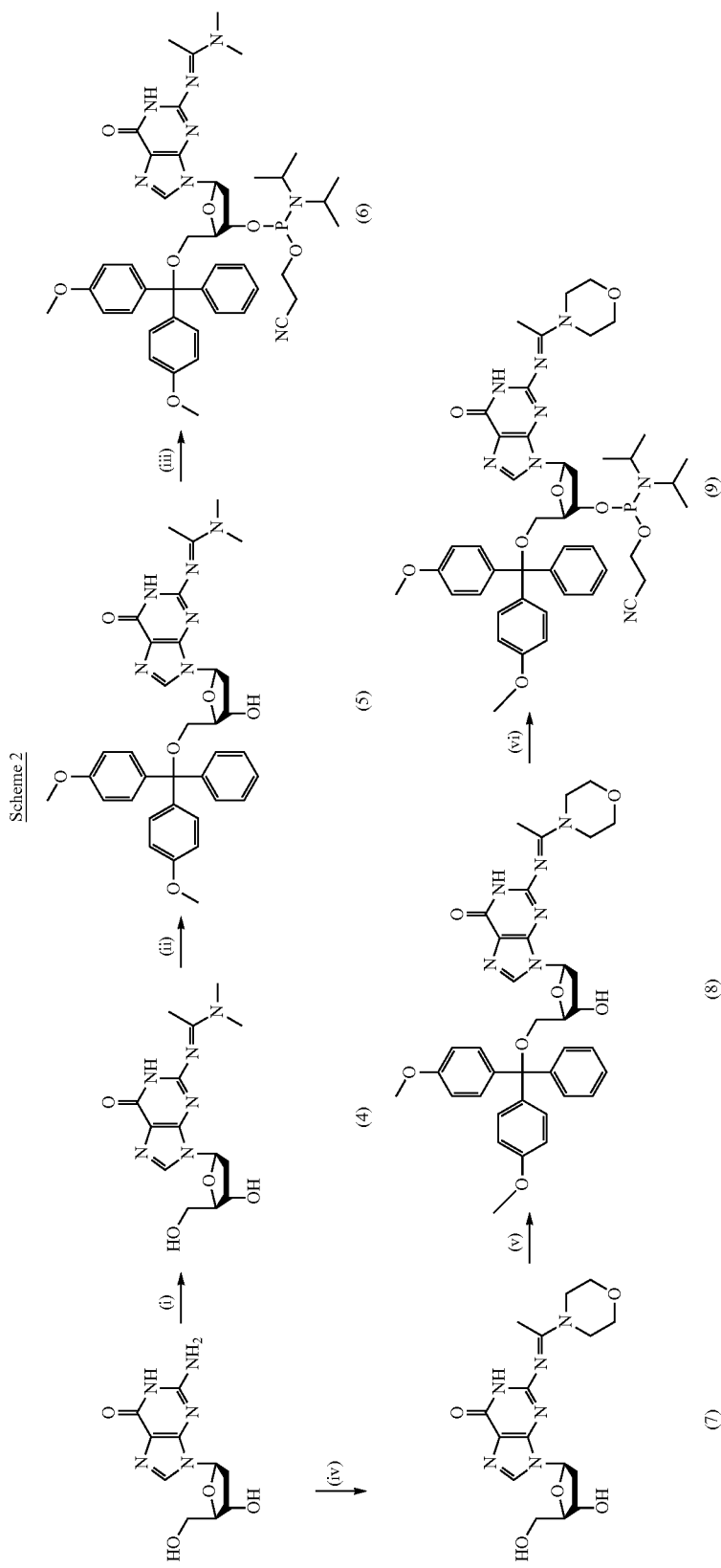

2-N-(1-(Dimethylamino)ethylidene)-2'-deoxyguanosine (4)

2-N-(1-(Dimethylamino)ethylidene)-2'-deoxyguanosine was synthesized according to the literature procedure with minor modification (Lu, J.; Khdour, O. M.; Armstrong, J. S.; Hecht, S. M. Bioorg. Med. Chem., 2010, 18, 7628-7638). 2'-deoxyguanosine dehydrate (3.66 g 12 mmol) was suspended in dry ethanol. N,N-Dimethylacetamide Diethyl acetal (7.8 g, 44 mmol) was added to the suspension with constant stirring. The mixture was warmed to ~70° C. for an hour until the solution became homogenized (pale yellow). Stirring was continued for 24 h. Ethanol was removed by rotary evaporation under reduced pressure. The sticky residue was washed several times with diethylether till the residue become non-sticky solid. The compound was further purified by column chromatography using $CHCl_3$ as the eluent. Methanol was used as the gradient (0-20%). The compound was eluted first. After removing the solvent of the column fractions, the compound (4) was appeared as the foam. Yield: 1.95 g (48%); $R_f$ ($CHCl_3$/MeOH 10/2 v/v): 0.38; $^1$H NMR ($CDCl_3$, 400 MHz): δ8.02 (s, 1H), 6.34 (t, J=6.8 Hz, 1H), 5.84 (m, 1H), 4.75 (s, 1H), 4.14 (d, J=6.6 Hz, 1H), 4.14 (s, 1H), 3.86 (m, 2H), 3.5 (m, 2H), 3.16 (s, 6H, N(CH$_3$)$_2$), 2.71-2.19 (m, 2H), 2.21 (s, 3H, C—CH$_3$). $^{13}$C NMR ($CDCl_3$, 400 MHz): δ162.25, 158.66, 156.26, 147.26, 138.10, 88.70, 86.26, 71.67, 62.61, 40.95, 38.18, 30.29, 17.00; ESI MS: 337.1521 [MH]$^+$

5'-O-(Di-p-methoxytrityl)-2-N-(1-(dimethylamino)ethylidene)-2'-deoxyguanosine (5)

2-N-(1-(Dimethylamino)ethylidene)-2'-deoxyguanosine (4) (3.98 g 0.0118 mole) was dissolved in dry pyridine (25 mL) and the solution made saturated with argon. N,N-diisopropylethylamine (6.42 g, 0.05 mole, 8.65 mL) was added to the solution and stirred for 10 min under the argon. Solution of Di-p-methoxytritylchloride (4.2 g, 0.012 mole) in 25 mL of dry pyridine was prepared under the argon. The DMT-Cl solution was transferred to the solution of (4) under with the continuous flow of argon. The reaction was allowed to continue for 2 h with constant stirring under the argon. Solution was concentrated and further diluted with 100 mL of dichloromethane. The mixture was washed with saturated aqueous solution of NaHCO$_3$ (100 mL) thrice. The organic phase was further washed with saturated aqueous solution of NaCl (100 mL). The organic phase was dried over anhydrous Na$_2$SO$_4$. The compound was further purified by silica gel column chromatography in CH$_2$Cl$_2$ (MeOH was used as the gradient, 0-5%) with 3% triethylamine. After removing the solvent, the compound (5) appeared as the foam. Yield: 5.51 g (73%); $R_f$(CH$_2$Cl$_2$/MeOH 10/0.5 v/v): 0.31; $^1$H NMR (CDCl$_3$, 400 MHz): δ7.71 (s, 1H), 7.4-6.8 (m, 13H, aryl), 6.33 (t, J=7 Hz, 1H) 4.59 (m, 1H), 4.11 (m, 1H), 3.78 (s, 6H, (O—CH$_3$)$_2$), 3.6-3.2 (m, 4H), 3.12 (s, 6H, N(CH$_3$)$_2$), 2.55 (m, 2H), 2.21 (s, 3H, C—CH$_3$). $^{13}$C NMR (CDCl$_3$, 400 MHz): δ162.27, 158.55, 156.39, 147.78, 144.53, 135.86, 130.01, 127.90, 126.91, 119.30, 113.20, 86.55, 85.52, 82.97, 72.47, 64.20, 55.26, 40.83, 38.56, 37.87, 30.20, 16.85, 7.94; ESI MS: 639.3019 [MH]$^+$

5'-O-(Di-p-methoxytrityl)-2-N-(1-(dimethylamino)ethylidene)-2'-deoxyguanosine-2-Cyanoethyl-N,N-diisopropylphosphoramidite (6)

5'-O-(Di-p-methoxytrityl)-2-N-(1-(dimethylamino)ethylidene)-2'-deoxyguanosine (5) (596 mg, 0.93 mmole) was dissolved in 10 mL of dry CH$_2$Cl$_2$. N,N-diisopropylethylamine (1 mL) was added to the solution with continuous flow of argon and stirring. N,N-Diisopropyl-O-cyanoethyl-chlorophosphoramidite (440 mg, 1.86 mmol) was added to the solution and the reaction was allowed to continue for 2 h under argon. After the reaction was over the solution was poured into 30 mL of saturated aq. NaHCO$_3$ solution and extracted with CH$_2$Cl$_2$ (3×10 mL). The combined organic phases were dried over Na$_2$SO$_4$ and the solvent was evaporated. The resulting oil was purified by column chromatography with CH$_2$Cl$_2$ containing 3% triethylamine to give the final compound (6) as a light yellow foam. Yield: 0.74 g (94%). $R_f$ (CH$_2$Cl$_2$/MeOH 10/0.6 v/v): 0.45; $^1$H NMR (CDCl$_3$, 400 MHz): δ11.98 (s, 1H), 7.81 (d, J=8 Hz, 1H), 7.48-6.77 (m, 13H, aryl), 6.21 (t, J=6.9 Hz, 1H), 4.83 (m, 1H), 4.11 (m, 1H), 3.78 (s, 6H, (O—CH$_3$)$_2$), 3.6-3.2 (m, 4H), 3.12 (s, 6H, N(CH$_3$)$_2$), 2.55 (m, 2H), 2.21 (s, 3H, C—CH$_3$). $^{31}$P NMR (CDCl$_3$, 400 MHz): δ148.36, 147.86 (Diastereoisomers).

2-N-(1-(morpholino)ethylidene)-2'-deoxyguanosine (7)

2.85 g (10 mmol) of 2'-Deoxyguanosine hydrate was co-evaporated with pyridine 3 times and was suspended in 20 mL of dry methanol. 12 g of 4-(1,1-dimethoxyethyl) morpholine was added slowly with constant stirring under the argon. The reaction was allowed to continue for overnight at 60° C. till the solution become homogenous and pale yellow in colour. After the reaction methanol was removed by rotary evaporation. The sticky residue was washed several times with diethylether to obtain non-sticky white solid. The compound was further purified by silica gel column chromatography with CHCl$_3$ as the eluent. Methanol (0-20%) was used as the gradient. After removing the solvent the pure compound (7) appeared as white foam. Yield: 3.31 g (82%), $R_f$(CHCl$_3$/MeOH 10/2 v/v): 0.32, $^1$H NMR (CDCl$_3$, 400 MHz): δ7.92 (s, 1H), 6.04 (t, J=5.8 Hz, 1H), 5.67 (m, 1H), 4.17 (d, J=5.8 Hz, 1H), 3.84 (m, 2H), 3.52 (m, 2H), 3.43 (m, 4H. O(CH$_2$)$_2$), 2.96 (m, 4H, N(CH$_2$)$_2$), 2.71-2.19 (m, 2H), 2.03 (s, 3H, C—CH$_3$). $^{13}$C NMR (CDCl$_3$, 400 MHz): δ160.15, 157.26, 154.51, 148.34, 137.11, 87.85, 84.16, 70.28, 66.22, 45.86, 42.35, 38.38, 29.69, 16.80.

5'-O-(Di-p-methoxytrityl)-2-N-(1-(morpholino)ethylidene)-2'-deoxyguanosine (8)

2-N-(1-(morpholino)ethylidene)-2'-deoxyguanosine (7) (3.31 g 0.0087 mole) was dissolved in dry pyridine (25 mL) and the solution made saturated with argon. N,N-diisopropylethylamine (6.42 g, 0.05 mole, 8.65 mL) was added to the solution and stirred for 10 min under the argon. Solution of Di-p-methoxytritylchloride (2.9 g, 0.0087 mole) in 25 mL of dry pyridine was prepared under the argon. The DMT-Cl solution was transferred to the solution of (10) with the continuous flow of argon. The reaction was allowed to continue for 3 h with constant stirring under the argon. The solution was concentrated and further diluted with 100 mL of dichloromethane. The mixture was washed with saturated aqueous solution of NaHCO$_3$ (100 mL) thrice. The organic phase was further washed with saturated aqueous solution of NaCl (100 mL). The organic phase was dried over anhydrous Na$_2$SO$_4$. The compound was further purified by silica gel column chromatography in CH$_2$Cl$_2$ (MeOH was used as the gradient, 0-5%) with 3% triethylamine. After removing the solvent, the compound (8) appeared as the white foam.

Yield: 4.89 g (83%); R$_f$ (CH$_2$Cl$_2$/MeOH 10/0.5 v/v): 0.36; $^1$H NMR (CDCl$_3$, 400 MHz): δ7.78 (s, 1H), 7.3-6.6 (m, 13H, aryl), 6.03 (t, J=6.8 Hz, 1H) 4.59 (m, 1H), 3.84 (s, 6H, (O—CH$_3$)$_2$), 3.7-3.4 (m, 4H), 3.33 (m, 4H, O(CH$_2$)$_2$), 3.02 (m, 4H, N(CH$_2$)$_2$), 2.55 (m, 2H), 2.16 (s, 3H, C—CH$_3$). $^{13}$C NMR (CDCl$_3$, 400 MHz): δ168.22, 160.29, 158.89, 156.19, 148.18, 143.23, 137.16, 132.11, 128.10, 127.21, 123.22, 120.24, 118.60, 113.28, 89.03, 86.55, 85.12, 82.27, 72.47, 66.90, 56.26, 45.83, 37.66, 32.87, 30.20, 16.95.

5'-O-(Di-p-methoxytrityl)-2-N-(1(morpholino)ethylidene)-2'-deoxyguanosine-2-cyanoethyl-N,N-diisopropylphosphoramidite (9)

5'-O-(Di-p-methoxytrityl)-2-N-(1-(morpholino)ethylidene)-2'-deoxyguanosine (8) (1.7 g, 0.0025 mole) was dissolved in 10 mL of dry CH$_2$Cl$_2$. N,N-diisopropylethylamine (6 mL) was added to the solution with continuous flow of argon and stirring. N,N-Diisopropyl-O-cyanoethylchlorophosphoramidite (590 mg, 0.0025 mole) was added to the solution and the reaction was allowed to continue for 2 h under argon. After the reaction was over the solution was poured into 30 mL of saturated aq. NaHCO$_3$ solution and extracted with CH$_2$Cl$_2$ (3×10 mL). The combined organic phases were dried over Na$_2$SO$_4$ and the solvent was evaporated. The resulting oil was purified by column chromatography with CH$_2$Cl$_2$ containing 3% triethylamine to give the final compound as white foam. The compound (9) was further purified by cold hexane precipitation from dichloromethane solution. Yield: 1.62 g (77%). R$_f$(CH$_2$Cl$_2$/MeOH 10/0.7 v/v): 0.49, $^{31}$P NMR (CDCl$_3$, 400 MHz): δ147.56, 146.86 (Diastereoisomers).

Scheme 3 depicts the synthesis of compound (15) according to the following conditions: (i) 2,2-Dimethoxy-1-methylpyrrolidine, methanol, RT (3 h); (ii) 4,4-Dimethoxytritylchloride, pyridine, N,N-Diisopropylethylamine (2 h); (iii) N,N-Diisopropyl-Cyanoethyl phosphoramiditechloride, N,N-Diisopropylethylamine, CH$_2$Cl$_2$ (2 h); (iv) 4-(1,1-dimethoxyethyl)morpholine, RT, Overnight; (v) 4,4-Dimethoxytritylchloride, pyrideine, N,N-Diisopropylethylamine (2 h); (vi) N,N-Diisopropyl-Cyanoethyl phosphoramiditechloride, N,N-Diisopropylethylamine, CH$_2$Cl$_2$ (2 h).

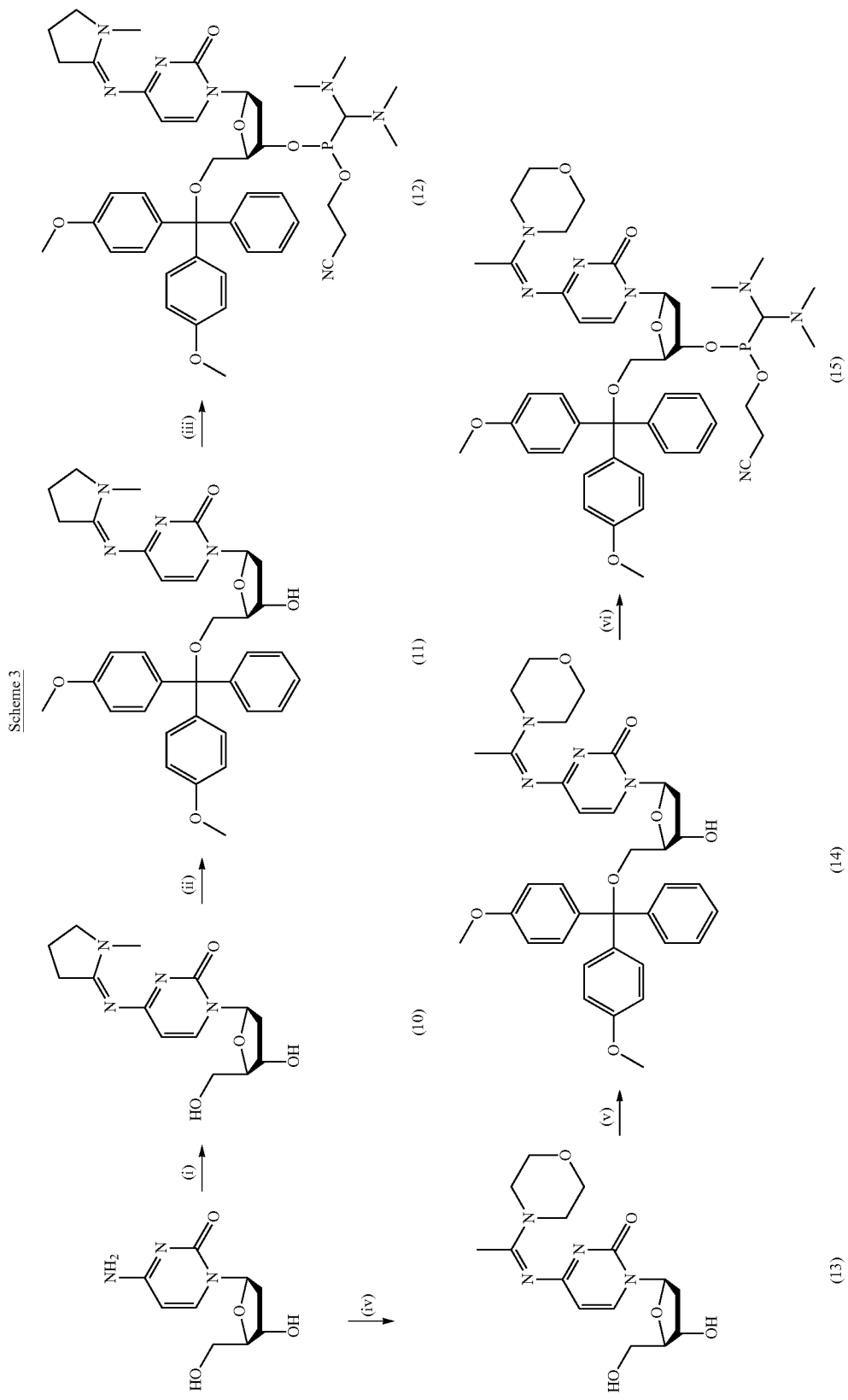

Synthesis of 4-N—(N-methylpyrrolidin-2-ylidene)-2'-deoxycytidine (10)

2.5 g (10 mmol) of 2'-Deoxycytidine hydrate (2a) was suspended in 20 mL of dry methanol. 3.8 g (26 mmol) of 2,2-Dimethoxy-1-methylpyrrolidine was added slowly with constant stirring under the argon. The reaction was allowed to continue for 3 h till the solution become homogenous and pale yellow in colour. After the reaction methanol was removed by rotary evaporation. The sticky residue was washed several times with diethylether to obtain non-sticky solid. The compound was further purified by silica get column chromatography with $CH_2Cl_2$ as the eluent. Methanol (0-20%) was used as the gradient. After removing the solvent the pure compound appeared as a white foam. Yield: 2.61 g (85%); $R_f$ ($CH_2Cl_2$/MeOH 10/2 v/v): 0.3; $^1$H NMR ($CDCl_3$, 400 MHz): δ7.91 (d, J=7.8 Hz, 1H), 6.13 (t, J=7.1 Hz, 1H), 6.03 (d, J=8 Hz, 1H), 4.55 (m, 1H), 4.01 (m, 1H), 3.88 (m, 2H), 3.48 (m, 2H), 3.11 (m, 2H), 3.05 (, 3H), 2.41 (m, 2H), 2.06 (m, 2H); $^{13}$C NMR ($CDCl_3$, 400 MHz): δ172.20, 169.00, 156.74, 141.98, 103.40, 87.53, 70.17, 61.71, 51.71, 40.56, 31.93, 30.53, 19.71; ESI MS: 309.1583 [MH]$^+$

Synthesis of 5'-O-(Di-p-methoxytrityl)-4-N—(N-methylpyrrolidin-2-ylidene)-2'-deoxycytidine (11)

4.2 g (0.0136 mole) of 4-N—(N-methylpyrrolidin-2-ylidene)-2'-deoxycytidine (10) was dissolved in 25 mL of dry pyridine. 9.88 mL of N,N-diisopropylethylamine was added to the solution under argon and stirred for 10 min. 4.8 g (0.0143 mole) of DMT-Cl dissolved in 25 mL of dry pyridine was added under argon and with constant stirring. The reaction was allowed to continue for 2 h. The solution was concentrated and further diluted with 100 mL of dichloromethane. The mixture was washed with saturated aqueous solution of $NaHCO_3$ (100 mL) thrice. The organic phase was further washed with saturated aqueous solution of NaCl (100 mL). The organic phase was dried over anhydrous $Na_2SO_4$. The compound was further purified by silica gel column chromatography in $CH_2Cl_2$ (MeOH was used as the gradient, 0-5%) with 3% triethylamine. After removing the solvent, the compound (11) appeared as the pale yellow foam. Yield: 6.48 g (78%); $R_f$ ($CH_2Cl_2$/MeOH 10/0.5 v/v): 0.4; $^1$H NMR ($CDCl_3$, 400 MHz): δ7.90 (d, 1H), 7.44-6.80 (m, 13H, aryl), 6.42 (t, J=6.8 Hz, 1H), 5.81 (d, J=8 Hz, 1H), 4.54 (m, 1H), 4.15 (m, 1H), 3.80 (s, 6H, (O—$CH_3$)$_2$), 3.70-3.40 (m, 4H), 3.15 (t, J=6.8 Hz, 2H), 3.03 (s, 3H, N—$CH_3$), 2.68 (m, 2H), 2.21 (m, 2H). $^{13}$C NMR ($CDCl_3$, 400 MHz): δ172.09, 169.02, 158.53, 156.59, 144.54, 140.50, 130.10, 128.17, 127.91, 126.91, 113.22, 103.17, 86.64, 86.44, 86.01, 71.52, 63.31, 55.24, 51.55, 42.03, 31.82, 30.63, 19.71; ESI MS: 611.2997 [MH]$^+$

5'-O-(Di-p-methoxytrityl)-4-N—(N-methylpyrrolidin-2-ylidene)-2'-deoxycytidine-2-cyanoethyl-N,N-diisopropylphosphoramidite (12)

5'-O-(Di-p-methoxytrityl)-4-N—(N-methylpyrrolidin-2-ylidene)-2'-deoxycytidine (11) (456 mg, 0.75 mmole) was dissolved in 10 mL of dry $CH_2Cl_2$. N,N-diisopropylethylamine (1 mL) was added to the solution with continuous flow of argon and stirring. N,N-Diisopropyl-O-cyanoethylchlorophosphoramidite (350 mg, 1.48 mmol) was added to the solution and the reaction was allowed to continue for 2 h under argon. After the reaction was over the solution was poured into 30 mL of saturated aq. $NaHCO_3$ solution and extracted with $CH_2Cl_2$ (3×10 mL). The combined organic phases were dried over $Na_2SO_4$ and the solvent was evaporated. The resulting oil was purified by column chromatography with $CH_2Cl_2$ containing 3% triethylamineto give the final compound (12) as a light yellow foam. Yield: 0.53 g (87%). $R_f$ ($CH_2Cl_2$/MeOH 10/0.8 v/v): 0.5; $^{31}$P NMR ($CDCl_3$, 400 MHz): δ149.48, 148.78 (Diastereoisomers)

4-N-(1-(morpholino)ethylidene)-2'-deoxycytidine (13)

2.45 g (10 mmol) of 2'-Deoxycytidine monohydrate was co-evaporated with pyridine 3 times and was suspended in 20 mL of dry methanol. 10 g of 4-(1,1-dimethoxyethyl)morpholine was added slowly with constant stirring under the argon. The reaction was allowed to continue for overnight. After the reaction methanol was removed by rotary evaporation. The sticky residue was washed several times with diethylether till non-sticky white powder was obtained. The compound was further purified by silica gel column chromatography with $CHCl_3$ as the eluent. Methanol (0-10%) was used as the gradient. After removing the solvent the pure compound (13) appeared as white foam. Yield: 3.0 g (88%), $R_f$ ($CHCl_3$/MeOH 10/2 v/v): 0.38; $^1$H NMR ($CDCl_3$, 400 MHz): δ7.53 (d, J=6.3 Hz, 1H), 6.01 (t, J=6.7 Hz, 1H), 5.27 (d, J=7.4 Hz, 1H), 4.35 (m, 1H), 3.91 (m, 1H), 3.88 (m, 2H), 3.55 (m, 4H, O($CH_2$)$_2$), 2.91 (m, 4H, N($CH_2$)$_2$), 2.5-2.3 (m, 2H), 1.73 (s, 3H, C—$CH_3$). $^{13}$C NMR ($CDCl_3$, 400 MHz): δ163.85, 160.12, 153.81, 142.14, 108.11, 92.17, 84.72, 71.60, 67.08, 60.40, 44.78, 40.92, 22.98.

5'-O-(Di-p-methoxytrityl)-4-N-(1-(morpholino)ethylidene)-2'-deoxycytidine (14)

4-N-(1-((morpholino)ethylidene))-2'-deoxycytidine (13) (2.98 g 0.0088 mole) was dissolved in dry pyridine (25 mL) and the solution made saturated with argon. N,N-diisopropylethylamine (6.42 g, 0.05 mole, 8.65 mL) was added to the solution and stirred for 10 min under the argon. Solution of Di-p-methoxytritylchloride (2.95 g, 0.0088 mole) in 25 mL of dry pyridine was prepared under the argon. The DMT-Cl solution was transferred to the solution of 16 with the continuous flow of argon. The reaction was allowed to continue for 2 h with constant stirring under the argon. Solution was concentrated and further diluted with 100 mL of dichloromethane. The mixture was washed with saturated aqueous solution of $NaHCO_3$ (100 mL) thrice. The organic phase was further washed with saturated aqueous solution of NaCl (100 mL). The organic phase was dried over anhydrous $Na_2SO_4$. The compound was further purified by silica gel column chromatography in $CH_2Cl_2$ (MeOH was used as the gradient, 0-2%) with 3% triethylamine. After removing the solvent, the compound (14) appeared as the white foam. Yield: 4.25 g (75%); $R_f$ ($CH_2Cl_2$/MeOH 10/0.5 v/v): 0.38; $^1$H NMR ($CDCl_3$, 400 MHz): δ7.5-6.7 (m, 14H, aryl), 6.05 (t, J=6.7 Hz, 1H), 5.17 (d, J=7.4 Hz, 1H), 4.47 (m, 1H), 4.13 (m, 1H), 3.95 (m, 2H), 3.71 (s, 6H, (O—$CH_3$)$_2$), 3.48 (m, 4H, O($CH_2$)$_2$), 2.87 (m, 4H, N($CH_2$)$_2$), 2.6-2.3 (m, 2H), 1.67 (s, 3H, C—$CH_3$); $^{13}$C NMR ($CDCl_3$, 400 MHz): δ164.75, 161.32, 158.07, 151.71, 147.11, 142.34, 136.21, 129.88, 127.62, 125.65, 115.23, 109.11, 92.17, 87.02, 84.72, 71.60, 68.09, 61.38, 54.28, 44.71, 41.22, 21.61.

5'-O-(Di-p-methoxytrityl)-4-N-(1-(morpholino)ethylidene)-2'-deoxycytidine-2-cyanoethyl-N,N-diisopropylphosphoramidite (15)

5'-O-(Di-p-methoxytrityl)-4-N-(1-morpholinoethylideneamino)-2'-deoxycytidine (14) (1.60 g, 0.0025 mole) was dissolved in 10 mL of dry CH$_2$Cl$_2$. N,N-diisopropylethylamine (6 mL) was added to the solution with continuous flow of argon and stirring. N,N-Diisopropyl-O-cyanoethylchlorophosphoramidite (590 mg, 0.0025 mole) was added to the solution and the reaction was allowed to continue for 2 h under argon. After the reaction was over the solution was poured into 30 mL of saturated aq. NaHCO$_3$ solution and extracted with CH$_2$Cl$_2$ (3×10 mL). The combined organic phases were dried over Na$_2$SO$_4$ and the solvent was evaporated. The resulting oil was purified by column chromatography with CH$_2$Cl$_2$ containing 3% triethylamine to give the final compound as white foam. The compound (15) was further purified by cold hexane precipitation from dichloromethane solution. Yield: 1.4 g (66%). R$_f$ (CH$_2$Cl$_2$/MeOH 10/0.5 v/v): 0.4, $^{31}$P NMR (CDCl$_3$, 400 MHz): δ147.39, 146.13 (Diastereoisomers).

The following examples illustrate the general synthetic strategy of compounds (16-21) describe herein.

Synthesis of 5'-O-Dimethoxytrityl-2'-deoxyribonucleoside-3'-O—S-ethylbenzothioate-pyrrolidinylphosphoramidite

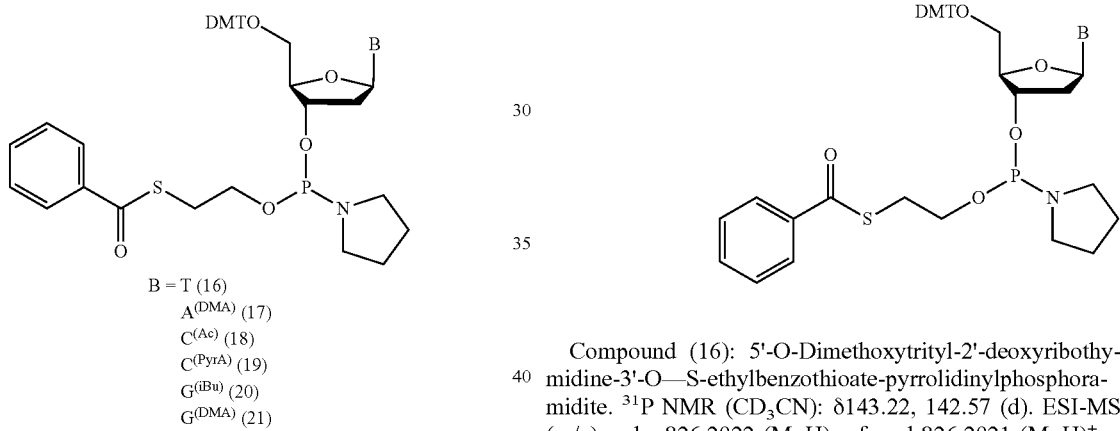

B = T (16)
A$^{(DMA)}$ (17)
C$^{(Ac)}$ (18)
C$^{(PyrA)}$ (19)
G$^{(iBu)}$ (20)
G$^{(DMA)}$ (21)

Bis(1-pyrrolidinyl)chlorophosphine (0.016 mols, 4 grams) was dissolved in anhydrous dichloromethane (20 mL) in a 250 mL round-bottom flask and Triethylamine (1 eq) was added to the solution and stirred under argon at room temperature. In the end 5'-O-dimethoxytrityl-2'-deoxyribonucleoside (0.016 mols, 1.0 equiv) was added to this solution. The mixture was allowed to stir under nitrogen at room temperature for thirty minutes when the 31P NMR spectrum indicated complete conversion of the starting material to product. At this point ethyl thiosalicylate (1.0 equiv) was added to the mixture and 1H-ethylthiotetrazole (0.25 M in anhydrous acetonitrile, Glen Research, VA, 0.5 equiv) was added immediately after dropwise via a syringe over a period of 15 min. The mixture was allowed to stir under nitrogen at room temperature until the $^{31}$P NMR spectrum indicated complete conversion of the phosphorodiamidite. The solvent was removed in vacuo, the crude product was isolated by Agilent preparative HPLC SD-1 system using a 0-60% gradient of acetonitrile in ethyl acetate containing 2% trimethylamine. The following scheme depicts the synthesis described above:

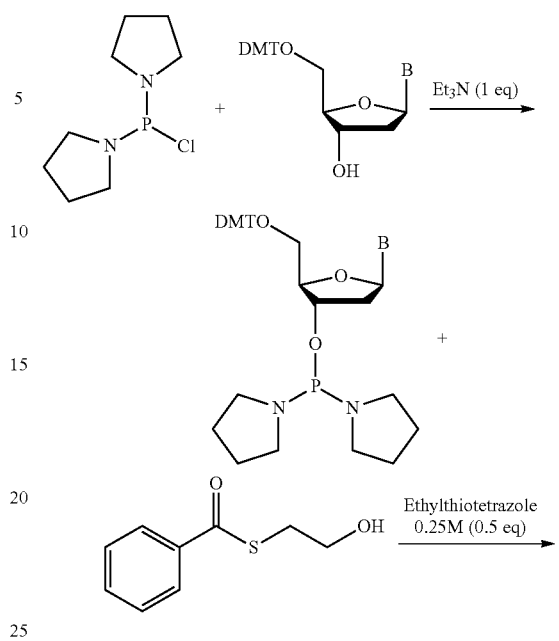

Compound (16): 5'-O-Dimethoxytrityl-2'-deoxyribothymidine-3'-O—S-ethylbenzothioate-pyrrolidinylphosphoramidite. $^{31}$P NMR (CD$_3$CN): δ143.22, 142.57 (d). ESI-MS (m/z): calc. 826.2922 (M+H)+, found 826.2921 (M+H)$^+$.

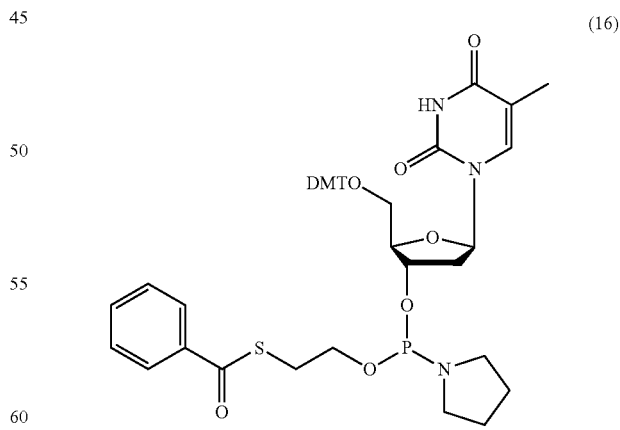

(16)

Compound (17): 5'-O-Dimethoxytrityl-N$^6$—(N,N-dimethylamidino)-2'-deoxyriboadenosine-3'-O—S-ethylbenzothioate-pyrrolidinylphosphoramidite. $^{31}$P NMR (CD$_3$CN): δ 142.92, 142.79 (d). ESI-MS (m/z): calc. 904.3616 (M+H)$^+$. found 904.3607 (M+H)$^+$.

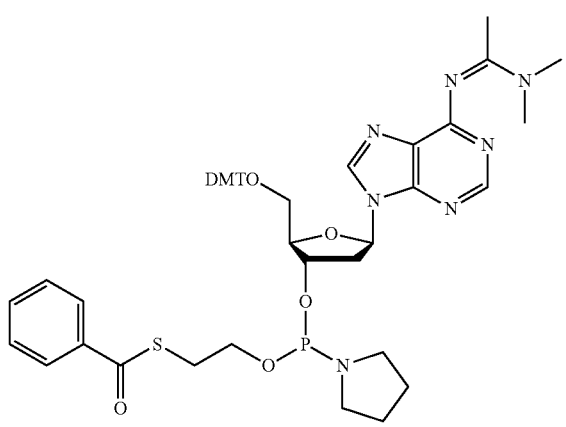

Compound (18): 5'-O-Dimethoxytrityl-N⁴-acetyl-2'-deoxyribocytidine-3'-O—S-ethylbenzothioate-pyrrolidinylphosphoramidite. ³¹P NMR (CD$_3$CN): δ 143.70, 143.17 (d). ESI-MS (m/z): calc. 853.3031 (M+H)+, found 853.3035 (M+H)⁺.

(18)

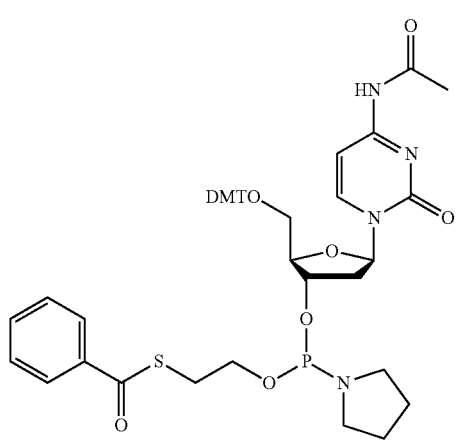

Compound (19): 5'-O-Dimethoxytrityl-N⁴-(N-methyl-2-pyrrolidinyldene)-2'-deoxyribocytidine-3'-O—S-ethylbenzothioate-pyrrolidinylphosphoramidite. ³¹P NMR (CD$_3$CN): δ143.41, 142.80 (d). ESI-MS (m/z): calc. 892.3504 (M+H)⁺. found 853.3506 (M+H)⁺.

(19)

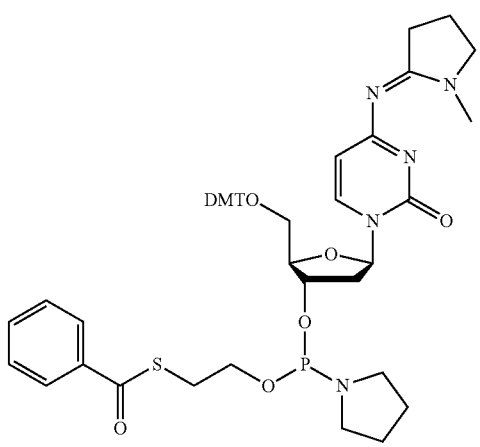

Compound (20): 5'-O-Dimethoxytrityl-N²-isobutyryl-2'-deoxyriboguanosine-3'-O—S-ethylbenzothioate-pyrrolidinylphosphoramidite. ³¹P NMR (CD$_3$CN): δ 143.17, 143.13 (d). ESI-MS (m/z): calc. 921.3406 (M+H)⁺. found 921.3385 (M+H)⁺.

(20)

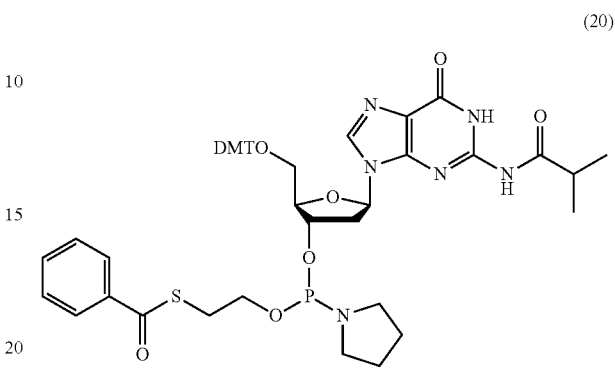

Compound (21): 5'-O-Dimethoxytrityl-N²—(N,N-dimethylamidino)-2'-deoxyriboguanosine-3'-O—S-ethylbenzothioate-pyrrolidinylphosphoramidite. ³¹P NMR (CD$_3$CN): δ 142.92, 142.79 (d). ESI-MS (m/z): calc. 920.3566 (M+H)⁺. found 920.3561 (M+H)⁺.

(21)

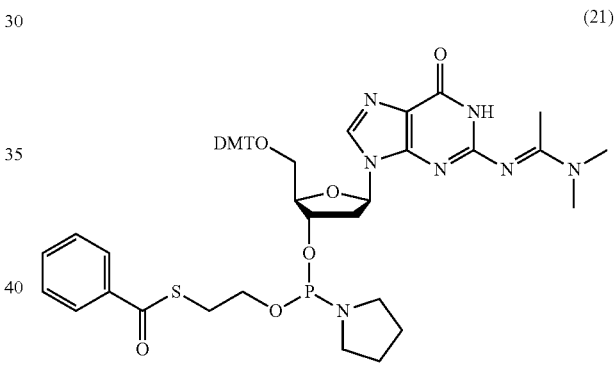

Synthesis of Arrays

Figure 25:
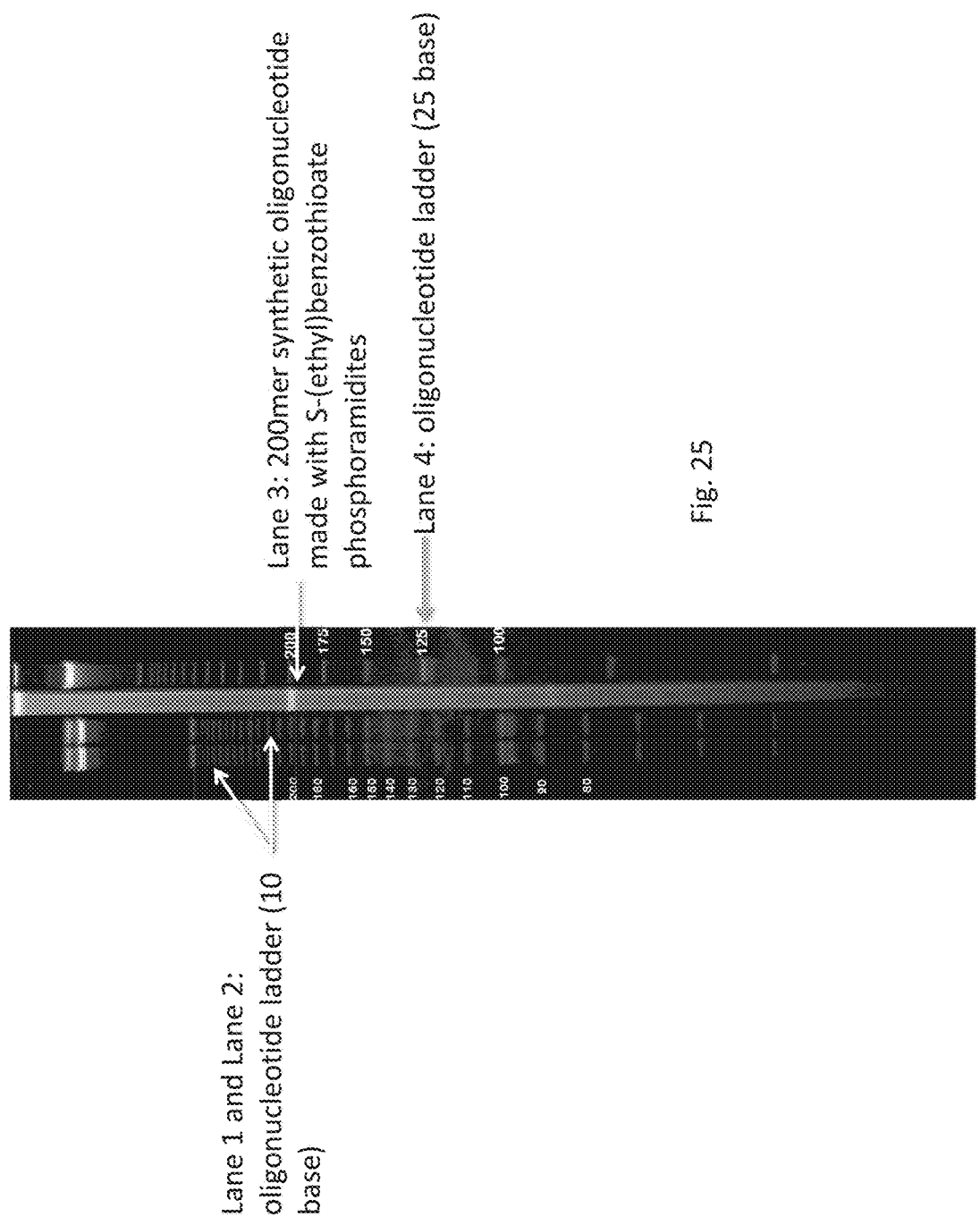
FIG. 25 depicts a denaturing polyacrylamide gel electrophoresis of a 200mer polynucleotide synthesized on an array using 3'-S-(ethyl)benzothioate phosphoramidites, and $N^6$—(N,N-dimethylamidino) dA (compounds 16, 17, 18, 20).

A DNA microarray was manufactured on an Agilent array writer according to Agilent manufacturing process described by Leproust et al. in Nucleic Acids Research (2010), Vol. 38(8), pp 2522-2540. A set of 5,528 unique oligonucleotide sequences containing A,G,C,T and ranging from 178 to 202 nucleotides long were synthesized with compounds: T(16), C(18), A(17) and G(20). The oligonucleotides were in situ synthesized on a cleavable linker on a silylated 6.625×6 in. wafer. At the end of the synthesis, the oligonucleotides were deprotected and cleaved from individual slide by an overnight ammonia gas treatment performed at room temperature. The sequences of the oligonucleotides included:

5' Adapter=29 nucleotides
Sequencing Primer=32 nucleotides
Barcode=16 bases
Query Sequence=76 or 100 bases
3' Adapter=25 nucleotides required to perform a sequencing analysis on an Illumina MiSeq system. The sequence analysis confirmed the integrity and the presence of the full length sequences. Additionally, a single 200-mer oligonucleotide sequence 5'-AATGATACGGCGACCACCGAGATCTACACCGACAGGTT CAGAGTTCTACAGTCCGACGATCGACGTTCCCAG GATACTTATAGGAGGGGCAAACCTCTTCTCTAGAG TCGCTG GTCCTATCCAGTAAACCACTTGGTTAATG-TAAGAGGCCCGCCTTTCGATCAGAAACG TCTGGAT CTCGTATGCCGTCTTCTGCTTGT-3' (SEQ ID NO: 1) was synthesized on an array using the same protocol and the same phosphoramidite compounds: T(16), A(17), C(18) and G(20). The deprotection and cleavage from the array was performed as described before. Denaturing polyacrylamide gel electrophoresis of the product confirmed the successful synthesis of the 200mer (FIG. 25).

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The examples described herein contain important additional information, exemplification and guidance that can be adapted to the practice of this invention in its various embodiments and equivalents thereof.

EMBODIMENTS

Aspects of the present disclosure include a compound having the structural formula (I):

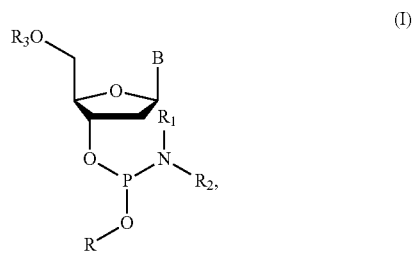

(I)

wherein B is a nucleobase or an analogue thereof; each of $R_1$ and $R_2$ is independently a linear, branched or cyclic, substituted or un-substituted alkyl, or $R_1$ and $R_2$ together form a 5-, 6-, 7- or 8-membered non-aromatic ring; $R_3$ is an acid-labile protecting group; and R is a group selected from the group consisting of benzyl alcohol derivatives, alpha-methyl aryl alcohol derivatives, naphthalene alcohol derivatives, bi-cyclic aliphatic alcohol derivatives, S-ethylthioate and amino acid derivatives, with the proviso that R is not o-methyl benzyl.

In some embodiments of the compound, B is a nucleobase or a protected nucleobase, wherein the nucleobase is selected from adenine, guanine, thymine, cytosine and uracil; and $R_3$ is a group selected from DMT, MMT, TMT, pixyl and pivaloyl. In some embodiments of the compound, each of $R_1$ and $R_2$ is independently is a linear, branched or cyclic, substituted or un-substituted $C_1$-$C_{18}$ alkyl. In some embodiments of the compound, each of $R_1$ and $R_2$ independently is a linear or branched un-substituted $C_1$-$C_6$ alkyl. In some embodiments, the compound has the structural formula ($I_a$):

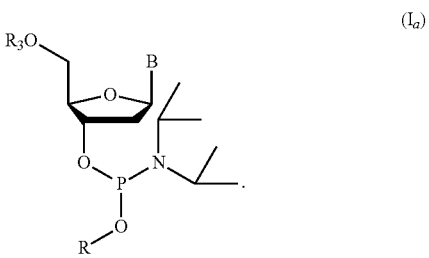

($I_a$)

In some embodiments of the compound, $R_1$ and $R_2$ together form a 5- or 6-membered non-aromatic ring, wherein the ring has 0 or 1 hetero-atom in the backbone. In some embodiments of the compound, $R_1$ and $R_2$ together form a 5-membered non-aromatic ring with 0 hetero-atoms in the backbone. In some embodiments, the compound has the structural formula ($I_b$):

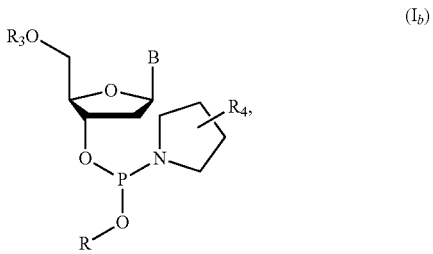

($I_b$)

wherein each $R_4$ is selected from hydrogen, halogen, $C_1$-$C_6$ alkyl and $C_1$-$C_6$ alkyloxy. In some embodiments, the compound has the structure of formula $I_c$

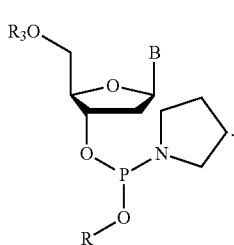

In some embodiments, the compound has the structural formula (I$_d$):

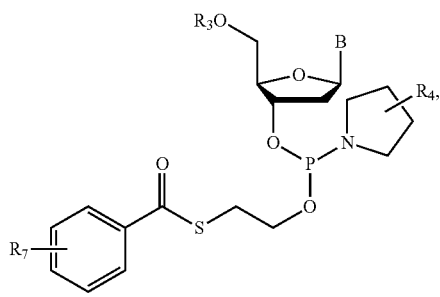

wherein each R$_7$ is independently hydrogen, halogen, C$_1$-C$_6$ alkyl or C$_1$-C$_6$ alkyloxy.

In some embodiments, the compound has the structural formula (I$_f$):

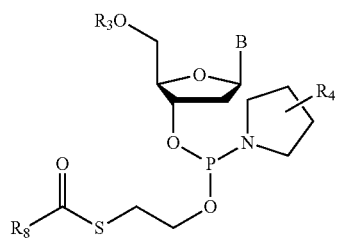

wherein R$_8$ is an aliphatic group.

In some embodiments of the compound, R is a derivative of benzyl alcohol having the structural formula (II):

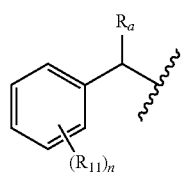

wherein: R$_a$ is hydrogen or alkyl; each R$_{11}$ is independently hydrogen, alkyl, alkoxy, alkyl-S—, cyano, methylcyano or halogen; and n is 1, 2 or 3.

In some embodiments of the compound, R is a derivative of benzyl alcohol selected from:

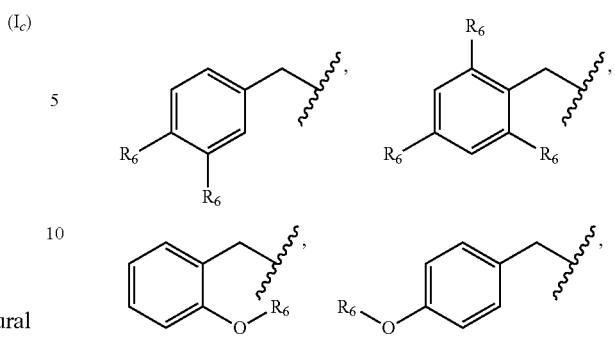

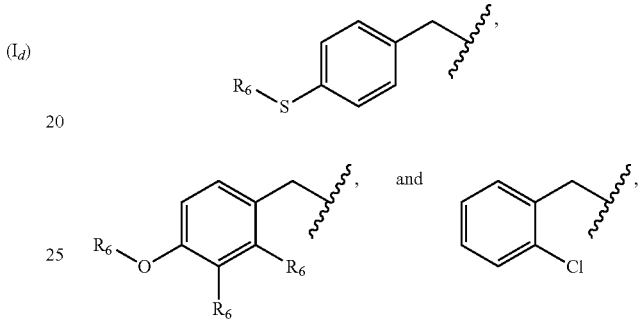

wherein each R$_6$ is independently selected from hydrogen, halogen, cyano, methylcyano and hydrocarbyl. In some embodiments of the compound, R is a derivative of benzyl alcohol having the structure:

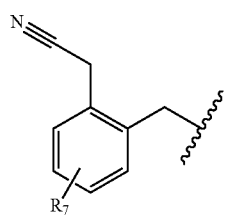

wherein R$_7$ is one or more substituents each independently selected from hydrogen, halogen, C$_1$-C$_6$ alkyl, C$_1$-C$_6$ alkyloxy and an electron withdrawing group.

In some embodiments of the compound, R is a derivative of an alpha-methyl aryl alcohol having the structural formula (III):

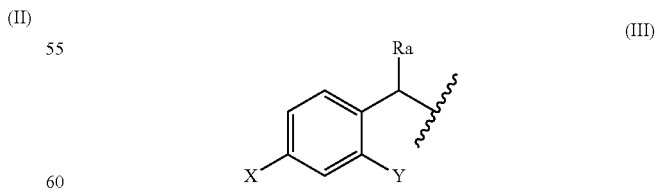

wherein X is hydrogen, halogen, cyano, methylcyano or trifluoromethyl; Y is hydrogen, alkyl, haloalkyl or alkoxyalkyl; and R$_a$ is hydrogen or alkyl.

In some embodiments of the compound, R is a derivative of an alpha-methyl aryl alcohol selected from:

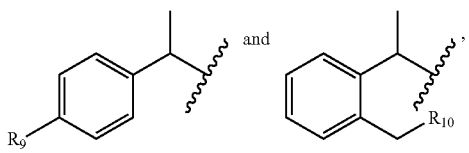

wherein $R_9$ is halogen, cyano or trifluoromethyl; and $R_{10}$ is selected from hydrogen, halogen, $C_1$-$C_6$ alkyl and $C_1$-$C_6$ alkyloxy.

In some embodiments of the compound, R is a derivative of a naphthalene alcohol having the structural formula (IV):

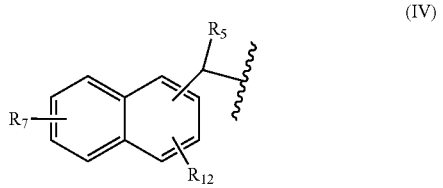

(IV)

wherein $R_7$ is selected from hydrogen, halogen, $C_1$-$C_6$ alkyl and $C_1$-$C_6$ alkyloxy; $R_5$ is selected from hydrogen and hydrocarbyl; and $R_{12}$ is selected from hydrogen and alkoxy.

In some embodiments of the compound, R is a derivative of a naphthalene alcohol selected from:

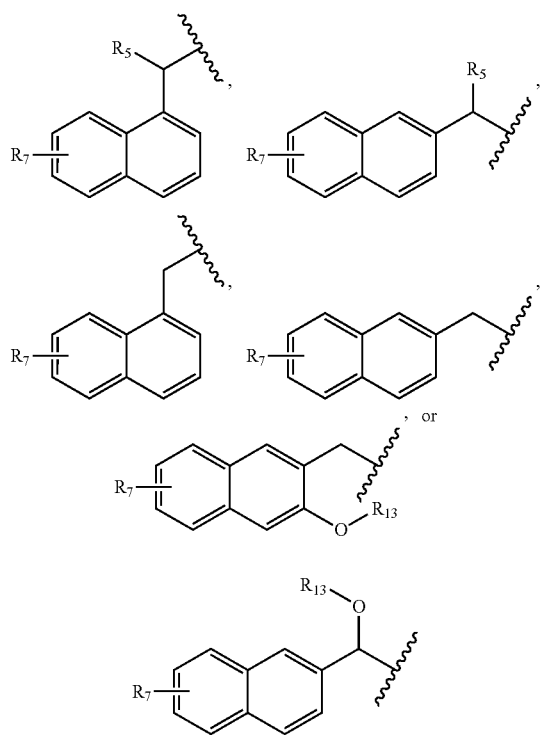

wherein $R_{13}$ is $C_1$-$C_6$ alkyl.

In some embodiments of the compound, R is a derivative of a bi-cyclic aliphatic alcohol having the structural formula (V) or (VI):

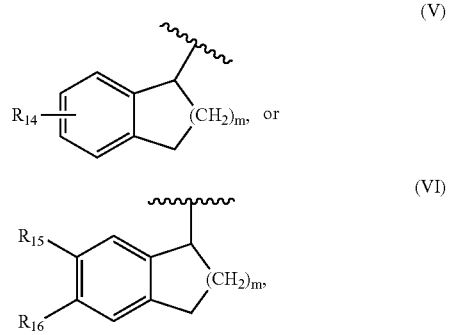

wherein $R_{14}$ is selected from hydrogen, halogen, $C_1$-$C_6$ alkyl and $C_1$-$C_6$ alkyloxy; $R_{15}$ and $R_{16}$ are each independently hydrogen, cyano, alkoxy, or halogen; and m is 1 or 2.

In some embodiments of the compound, R is a derivative of a bi-cyclic aliphatic alcohol selected from:

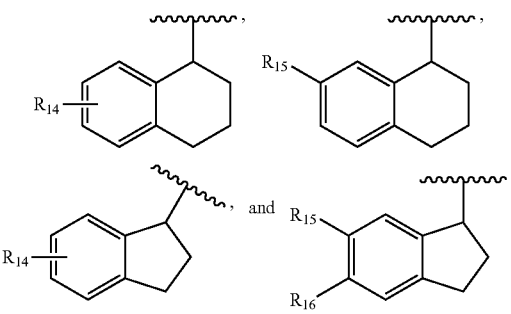

wherein $R_{14}$ is hydrogen, halogen, $C_1$-$C_6$ alkyl or $C_1$-$C_6$ alkyloxy; $R_{15}$ is hydrogen, halogen or $C_1$-$C_6$ alkoxy; and $R_{16}$ is hydrogen, cyano, or halogen.

In some embodiments of the compound, R is:

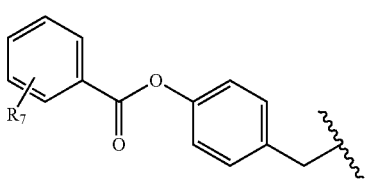

wherein $R_7$ is selected from hydrogen, halogen, hydrocarbyl and alkyloxy.

In some embodiments of the compound, R is selected from:

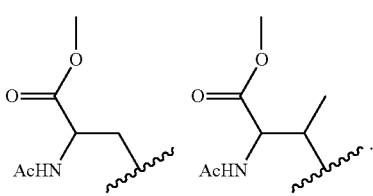 [SMILES: *CC(NC(C)=O)C(=O)OC ; *C(C)C(NC(C)=O)C(=O)OC ; "."]

In some embodiments of the compound, R is

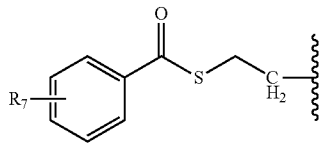

wherein $R_7$ is hydrogen, halogen, $C_1$-$C_6$ alkyl or $C_1$-$C_6$ alkyloxy.

In some embodiments of the compound, R is

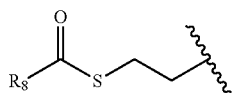

wherein $R_8$ is an aliphatic group.

In some embodiments of the compound, B comprises an amidine nucleobase protecting group. In some embodiments of the compound, the amidine nucleobase protecting group is an acetamidine protecting group. In some embodiments of the compound, the acetamidine protecting group is described by the following structure:

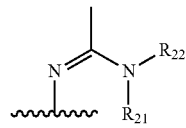

wherein $R_{21}$ and $R_{22}$ are each independently an alkyl, a substituted alkyl, or $R_{21}$ and $R_{22}$ are cyclically linked to form a 5 or 6 membered substituted or unsubstituted heterocycle. In some embodiments of the compound, $R_{21}$ and $R_{22}$ are methyl. In some embodiments of the compound, $R_{21}$ and $R_{22}$ are cyclically linked to form a 5 or 6 membered substituted or unsubstituted heterocycle, wherein the heterocycle is selected from the group consisting of morpholine, piperidine and pyrrolidine.

In some embodiments of the compound, acetamidine protecting group is described by the following structure:

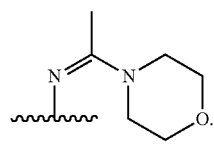 [SMILES: */N=C(/C)N1CCOCC1]

In some embodiments of the compound, B is described by one of the following structures:

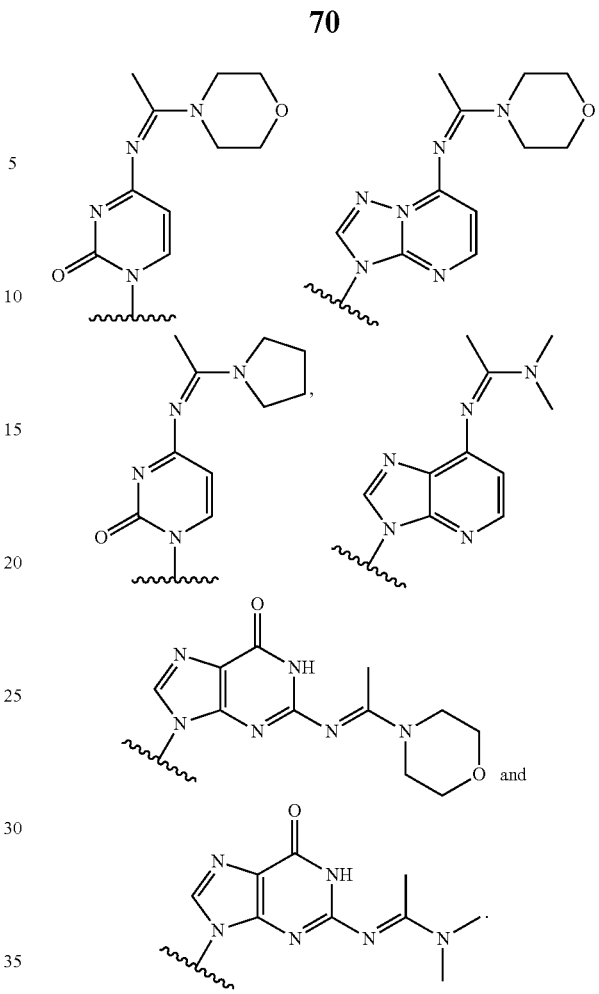

In some embodiments of the compound, R is

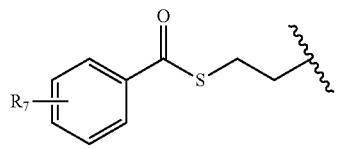

wherein $R_7$ is selected from hydrogen, halogen, hydrocarbyl and alkyloxy.

Also provided is a compound having the structural formula (VII)

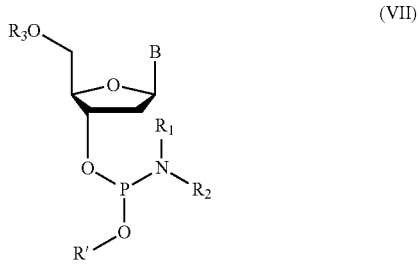

(VII)

wherein each of $R_1$ and $R_2$ is an isopropyl or $R_1$ and $R_2$ together form a pyrrolidine heterocyclic ring with N to which they are attached; $R_3$ is an acid-labile protecting group; R' is a group selected from a cyanoethyl group and a methyl group; and B is a protected nucleobase selected from:

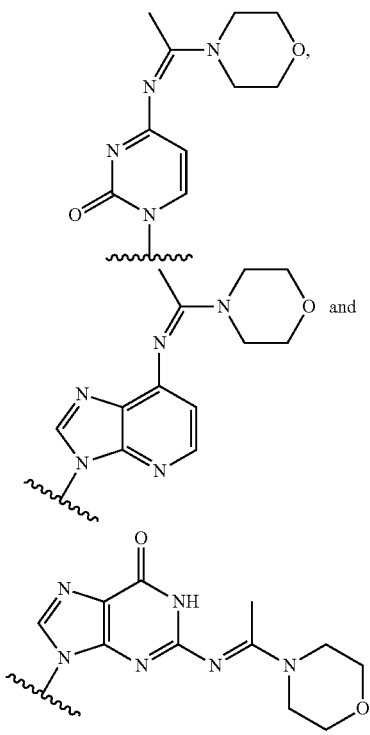

Also provided is a method of synthesizing a polynucleotide, the method comprising: (a) providing a nucleoside residue having an unprotected hydroxyl group; and (b) contacting the nucleoside residue with a nucleoside monomer (e.g., as described herein) to covalently bond the nucleoside monomer to the nucleoside residue and produce the polynucleotide. In some embodiments, the method further includes exposing the polynucleotide to an oxidizing agent. In some embodiments, the method further includes exposing the nucleic acid to a deprotection agent. In some embodiments, the method further comprises reiterating the contacting step at least once. In some embodiments of the method, the nucleoside residue is covalently bound to a solid support. In some embodiments, the method further comprises cleaving the nucleic acid from said solid support to produce a free nucleic acid. In some embodiments of the method, the nucleic acid is a DNA having a sequence of at least about 200 nucleotides. In some embodiments of the method, the nucleic acid is a DNA having a length of about 200 to about 1,000 nucleotides. In some embodiments of the method, the DNA has a length of about 300 to about 500 nucleotides. In some embodiments of the method, the DNA has less than 2 single nucleotide deletions per 100 nucleotides. In some embodiments of the method, the DNA has 1 or less single nucleotide deletions per 100 nucleotides. In some embodiments, the method further includes coupling a first free nucleic acid with a second free nucleic acid to produce an extended free nucleic acid having a length from about 300 to about 10,000 nucleotides. In some embodiments, the method further includes coupling one or more additional free nucleic acids to the extended free nucleic acid to produce a gene.

Also provided is a nucleic acid product produced by any one of the embodiments of the subject method described above. Also provided is an array of nucleic acids synthesized by the any one of the embodiments of the subject method described above. Also provided is a library, comprising a plurality of nucleic acids synthesized by any one of the embodiments of the subject method described above. Also provided is a library, comprising a plurality of nucleic acids having a length from about 300 to about 10,000 nucleotides, wherein each nucleic acid is composed of assembled nucleic acid fragments synthesized by any one of the embodiments of the subject method described above. In some embodiments of the library, the plurality of nucleic acids are assembled into a gene.

What is claimed is:

1. A compound having the structural formula (I):

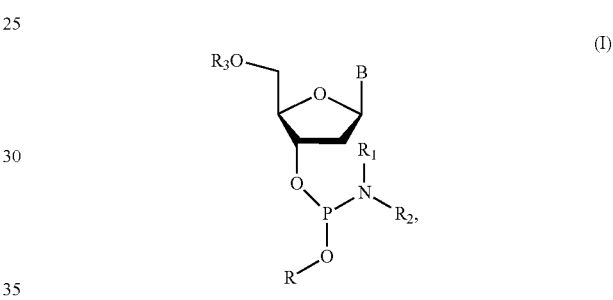

wherein

B is a nucleobase or an analogue thereof; wherein the B comprises an amidine nucleobase protecting group; and wherein the protecting group is described by the following structure:

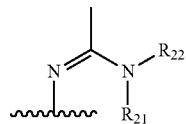

wherein $R_{21}$ and $R_{22}$ are each independently an alkyl, a substituted alkyl, or $R_{21}$ and $R_{22}$ are cyclically linked to form a 5- or 6-membered substituted or unsubstituted heterocycle;

each of $R_1$ and $R_2$ is independently a linear, branched or cyclic, substituted or un-substituted alkyl, or $R_1$ and $R_2$ together form a 5-, 6-, 7- or 8-membered non-aromatic ring;

$R_3$ is an acid-labile protecting group; and

R is a group selected from the group consisting of a benzyl, alpha-methyl aryl, naphthalene, bi-cyclic aliphatic, S-ethylthioate and an amino acid, with the proviso that R is not o-methyl benzyl.

2. The compound of claim 1, having the structural formula (I_b):

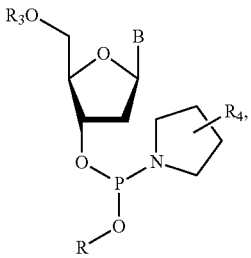

wherein
each R_4 is selected from hydrogen, halogen, $C_1$-$C_6$ alkyl and $C_1$-$C_6$ alkyloxy.

3. The compound of claim 2, having the structural formula (I_d):

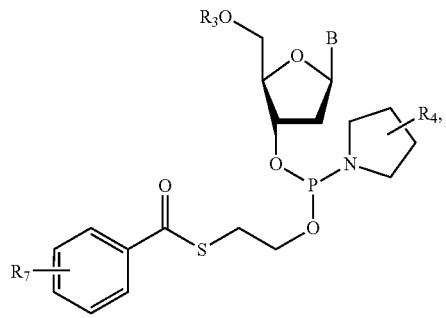

wherein each R_7 is independently hydrogen, halogen, $C_1$-$C_6$ alkyl or $C_1$-$C_6$ alkyloxy.

4. The compound of claim 2, having the structural formula (I_f):

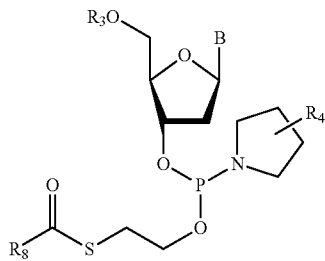

wherein R_8 is an aliphatic group.

5. The compound of claim 1, wherein R is a derivative of benzyl alcohol having the structural formula (II):

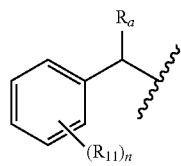

wherein:
R_a is hydrogen or alkyl;
each R_11 is independently hydrogen, alkyl, alkoxy, alkyl-S—, cyano, methylcyano or halogen; and
n is 1, 2 or 3.

6. The compound of claim 5, wherein R is a derivative of benzyl alcohol having the structure:

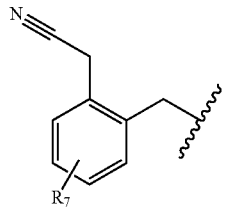

wherein R_7 is one or more substituents each independently selected from hydrogen, halogen, $C_1$-$C_6$ alkyl, $C_1$-$C_6$ alkyloxy and an electron withdrawing group.

7. The compound of claim 1, wherein R is a derivative of an alpha-methyl aryl alcohol having the structural formula (III):

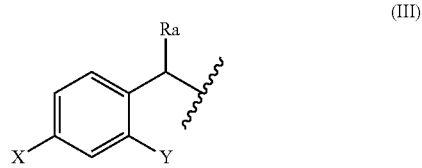

wherein X is hydrogen, halogen, cyano, methylcyano or trifluromethyl; Y is hydrogen, alkyl, haloalkyl or alkoxyalkyl; and R_a is hydrogen or alkyl.

8. The compound of claim 1, wherein R is a derivative of a naphthalene alcohol having the structural formula (IV):

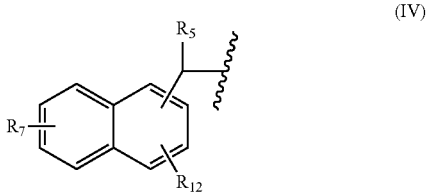

wherein R_7 is selected from hydrogen, halogen, $C_1$-$C_6$ alkyl and $C_1$-$C_6$ alkyloxy; R_5 is selected from hydrogen and hydrocarbyl; and R_12 is selected from hydrogen and alkoxy.

9. The compound of claim 1, wherein R is a derivative of a bi-cyclic aliphatic alcohol having the structural formula (V) or (VI):

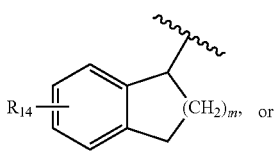

-continued

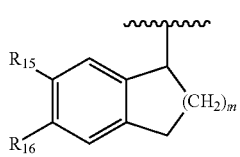
(VI)

wherein $R_{14}$ is selected from hydrogen, halogen, $C_1$-$C_6$ alkyl and $C_1$-$C_6$ alkyloxy; $R_{15}$ and $R_{16}$ are each independently hydrogen, cyano, alkoxy, or halogen; and m is 1 or 2.

10. The compound of claim 1, wherein R is:

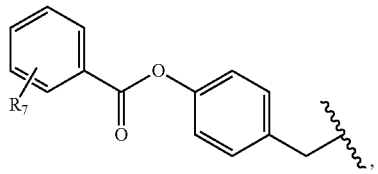

wherein $R_7$ is selected from hydrogen, halogen, hydrocarbyl and alkyloxy.

11. The compound of claim 1, wherein R is selected from:

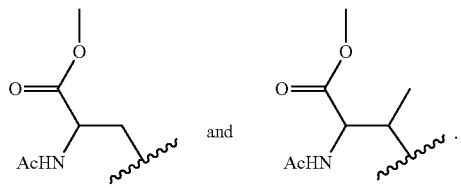 [SMILES: *CC(NC(C)=O)C(=O)OC ; *C(C)C(NC(C)=O)C(=O)OC]

12. The compound of claim 1, wherein R is

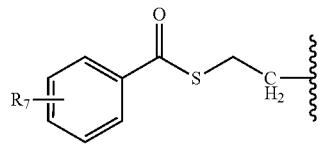

wherein $R_7$ is hydrogen, halogen, $C_1$-$C_6$ alkyl or $C_1$-$C_6$ alkyloxy.

13. The compound of claim 1, wherein R is

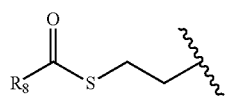

wherein $R_8$ is an aliphatic group.

14. The compound of claim 1, wherein the protecting group is described by the following structure:

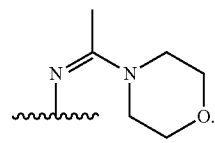 [SMILES: */N=C(/C)N1CCOCC1]

15. The compound of claim 1, wherein B is described by one of the following structures:

(structures shown)

, and

16. The compound of claim 15, wherein R is

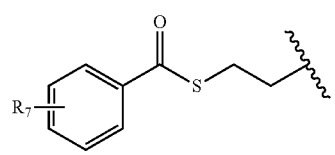

wherein $R_7$ is selected from hydrogen, halogen, hydrocarbyl and alkyloxy.

17. A method of synthesizing a polynucleotide, the method comprising:
   (a) providing a nucleoside residue having an unprotected hydroxyl group; and
   (b) contacting the nucleoside residue with a nucleoside monomer of claim 1 to covalently bond the nucleoside monomer to the nucleoside residue and produce the polynucleotide.

18. The method of claim 17, further comprising exposing the polynucleotide to an oxidizing agent.

19. The method of claim 17, wherein the nucleoside residue is covalently bound to a solid support.

20. The method of claim 19, wherein the polynucleotide is a DNA having a length of about 200 to about 1,000 nucleotides.

* * * * *

UNITED STATES PATENT AND TRADEMARK OFFICE
CERTIFICATE OF CORRECTION

PATENT NO. : 10,196,418 B2
APPLICATION NO. : 14/701288
DATED : February 5, 2019
INVENTOR(S) : Douglas J. Dellinger et al.

It is certified that error appears in the above-identified patent and that said Letters Patent is hereby corrected as shown below:

In the Drawings

On sheet 2 of 29, in Figure 2, Line 2, delete "naphtalenemethanol" and insert -- naphthalenemethanol --, therefor.

On sheet 3 of 29, in Figure 3, Line 1, delete "naphtalenemethanol" and insert -- naphthalenemethanol --, therefor.

On sheet 5 of 29, in Figure 4, Line 1, delete "naphtalenemethanol" and insert -- naphthalenemethanol --, therefor.

In the Specification

In Column 3, Lines 36-37, delete "naphtalenemethanol" and insert -- naphthalenemethanol --, therefor.

In Column 3, Lines 39-40, delete "naphtalenemethanol" and insert -- naphthalenemethanol --, therefor.

In Column 3, Lines 44-45, delete "naphtalenemethanol" and insert -- naphthalenemethanol --, therefor.

In Column 6, Line 29, delete "pyrrolodinoamidine," and insert -- pyrrolidinoamidine, --, therefor.

In Column 6, Lines 35-36, delete "N6-methyladenine, N6-isopentyladenine, 2-methylthio-N6-isopentyladenine," and insert -- $N^6$-methyladenine, $N^6$-isopentyladenine, 2-methylthio-$N^6$-isopentyladenine, --, therefor.

In Column 6, Line 49, delete "queosine," and insert -- queuosine, --, therefor.

In Column 14, Line 25, delete "phenoxyacteyl," and insert -- phenoxyacetyl, --, therefor.

In Column 14, Line 45, delete "queosine," and insert -- queuosine, --, therefor.

Signed and Sealed this
Seventeenth Day of September, 2019

Andrei Iancu
*Director of the United States Patent and Trademark Office*

In Column 16, Line 4, delete "(monomethoxytirtyl)," and insert -- (monomethoxytrityl), --, therefor.

In Column 19, Lines 51-57, after " 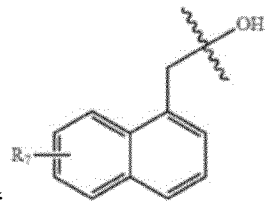 " insert -- , --.

In Column 21, Lines 25-30, delete " 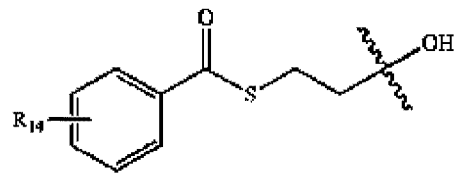 " and insert -- 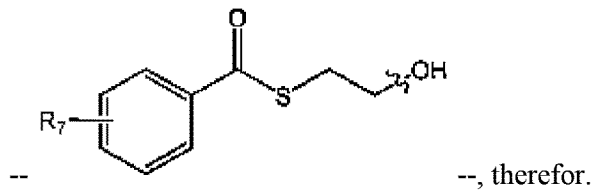 --, therefor.

In Column 23, Line 44, delete "queosine," and insert -- queuosine, --, therefor.

In Column 24, Line 43, delete "length, In" and insert -- length. In --, therefor.

In Column 28, Line 24, delete "Ethylio" and insert -- Ethylthio --, therefor.

In Column 28, Line 58, delete "Naphtalene" and insert -- Naphthalene --, therefor.

In Column 29, Line 38, delete "31P" and insert -- (31P --, therefor.

In Column 30, Line 24, delete "146,4," and insert -- 146.9, --, therefor.

In Column 34, Line 32, delete "147.6" and insert -- 147.6) --, therefor.

In Column 35, Line 27, after "(d)" insert -- . --.

In Columns 37-38, Line 55, delete "Sheat" and insert -- Sheath --, therefor.

In Columns 37-38, Line 56, delete "Sheat" and insert -- Sheath --, therefor.

In Column 39, Line 36, delete "methoxynaphtalenephosphoramidite" and insert -- methoxynaphthalenephosphoramidite --, therefor.

In Column 39, Line 66, delete "naphtalenemethanol" and insert -- naphthalenemethanol --, therefor.

CERTIFICATE OF CORRECTION (continued)

In Column 40, Line 2, delete "Naphtalenephosphoramidite" and insert
-- Naphthalenephosphoramidite --, therefor In Column 40, Line 29, delete "naphtalenemethanol" and insert -- naphthalenemethanol --, therefor.

In Column 40, Line 36, delete "naphtalenephosphoramidite" and insert
-- naphthalenephosphoramidite --, therefor.

In Column 40, Line 65, delete "naphtalenemethanol" and insert -- naphthalenemethanol --, therefor.

In Column 43, Line 64, delete "T-" and insert -- 2'- --, therefor.

In Column 45, Line 32, delete "cynoethyl)-" and insert -- cyanoethyl)- --, therefor.

In Column 47, Line 15, delete "0.1=" and insert -- J= --, therefor.

In Column 48, Line 18, after "Scheme 2" delete "I".

In Column 48, Lines 21-22, delete "2 h);" and insert -- (2 h); --, therefor.

In Column 51, Line 28, after "[MH]$^+$" insert -- . --.

In Column 51, Line 60, after "[MH]$^+$" insert -- . --.

In Column 57, Line 23, after "[MH]$^+$" insert -- . --.

In Column 57, Line 53, after "[MH]$^+$" insert -- . --.

In Column 58, Line 4, delete "triethylamineto" and insert -- triethylamine to --, therefor.

In Column 58, Line 7, after "(Diastereoisomers)" insert -- . --.

In Column 64, Line 67, delete "I$_c$" and insert -- (I$_c$): --, therefor.

In Column 70, Lines 1-10, after " 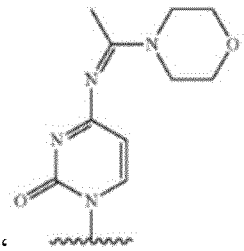 " insert -- , --.

CERTIFICATE OF CORRECTION (continued)
U.S. Pat. No. 10,196,418 B2

In Column 71, Lines 1-10, delete " 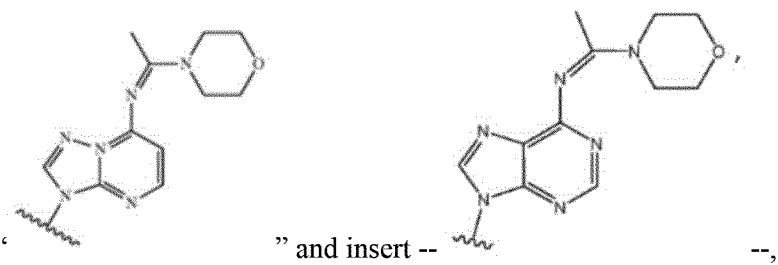 " and insert -- --, therefor.

In Column 70, Lines 11-20, delete " 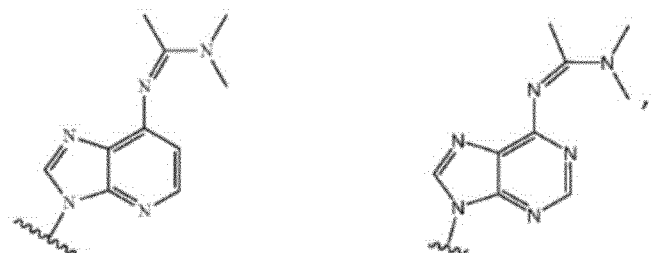 " and insert -- --, therefor.

In Column 71, Lines 15-24, delete " 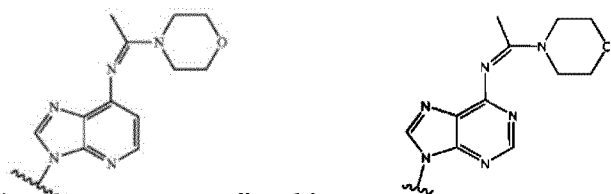 " and insert -- --, therefor.

In the Claims

In Column 74, Line 36, in Claim 7, delete "trifluromethyl;" and insert -- trifluoromethyl; --, therefor.

In Column 75, Lines 19-25, in Claim 10, delete " 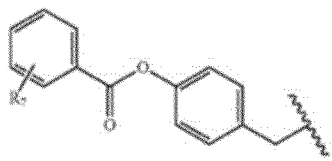 " and insert -- 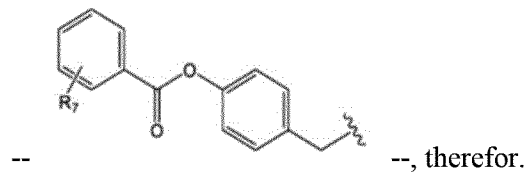 --, therefor.

CERTIFICATE OF CORRECTION (continued)
U.S. Pat. No. 10,196,418 B2

In Column 76, Lines 35-40, in Claim 15, after " 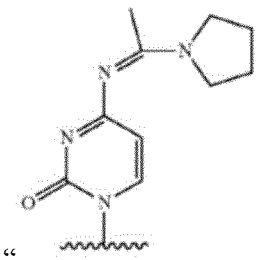 " insert -- , --.